(12) United States Patent
Kolczewski et al.

(10) Patent No.: US 7,825,253 B2
(45) Date of Patent: Nov. 2, 2010

(54) 2-AMINOQUINOLINE DERIVATIVES

(75) Inventors: Sabine Kolczewski, Loerrach (DE); Claus Riemer, Freiburg (DE); Lucinda Steward, Basel (CH); Juergen Wichmann, Steinen (DE); Thomas Woltering, Grenzach-Wyhlen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 629 days.

(21) Appl. No.: 11/859,045

(22) Filed: Sep. 21, 2007

(65) Prior Publication Data

US 2008/0081907 A1    Apr. 3, 2008

(30) Foreign Application Priority Data

Sep. 28, 2006   (EP)   .................................. 06121449

(51) Int. Cl.
*C07D 215/38*   (2006.01)
(52) U.S. Cl. ...................... 546/159; 546/160
(58) Field of Classification Search ................. 546/159, 546/160
See application file for complete search history.

(56) References Cited

FOREIGN PATENT DOCUMENTS

| WO | WO 03/037871 A1 | 5/2003 |
| WO | WO 03/037872 A1 | 5/2003 |
| WO | WO 2004/004726 A1 | 1/2004 |
| WO | WO 2004/096771 | 11/2004 |

OTHER PUBLICATIONS

Acheson, J Chem Soc, pp. 4440-4443, 1955.*
Hoyer et al., Pharmacol. Rev. vol. 46 (1994) pp. 157-204.
Rees et al., FEBS Letters, vol. 355 (1994) pp. 242-246.
Francken et al., Eur. J. Pharmacol. vol. 361 (1998) pp. 299-309.
Noda et al., J. Neurochem. vol. 84 (2003) pp. 222-232.
Thomas, D., The Pharmacology & Therapeutics, vol. 111 (2006) pp. 707-714.
Doly et al., The Journal of Comparative Neurology, vol. 476 (2004) pp. 316-329.
Dubertret et al., The Journal of Psychiatric Research vol. 38 (2004) pp. 371-376.

* cited by examiner

*Primary Examiner*—D. Margaret Seaman
(74) *Attorney, Agent, or Firm*—George W. Johnston; Patricia S. Rocha-Tramaloni; Kimberly J. Prior

(57) ABSTRACT

The present invention relates to compounds of the formula (I):

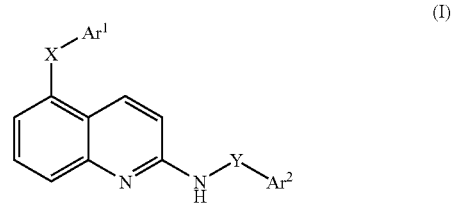

or pharmaceutically acceptable salts thereof,
wherein X, Y, $Ar^1$, and $Ar^2$ are as defined in the specification.

21 Claims, No Drawings

2-AMINOQUINOLINE DERIVATIVES

PRIORITY TO RELATED APPLICATION(S)

This application claims the benefit of European Patent Application No. 06121449.0, filed Sep. 28, 2006, which is hereby incorporated by reference in its entirety.

BACKGROUND OF THE INVENTION

The neurotransmitter 5-hydroxytryptamine (5-HT, serotonin) modulates a wide range of physiological and pathological processes in the central nervous system and periphery, including anxiety, sleep regulation, aggression, feeding and depression (Hoyer et al., *Pharmacol. Rev.* 46, 157-204, 1994). Both pharmacological characterization and molecular cloning of several 5-HT receptor genes has revealed that 5-HT mediates its diverse physiological actions through a multiplicity of receptor subtypes. These receptors belong to at least two different protein superfamilies: ligand-gated ion channel receptor (5-HT$_3$) and the G-protein-coupled 7-transmembrane receptors (thirteen distinct receptors cloned to date). In addition, within the G-protein-coupled receptors, serotonin exerts its actions through a multiplicity of signal transduction mechanisms.

The cloning and characterization of the human 5-HT$_{5A}$ serotonin receptor has been described in *FEBS Letters*, 355, 242-246 (1994). The sequence is not closely related to that of any previously known serotonin receptor, with the best homology being 35% to the human 5-HT$_{1B}$ receptor. It encodes a predicted 357 amino-acid protein, with seven putative transmembrane domains, consistent with that of a G-protein coupled receptor. The sequence is characterized by containing an intron between transmembrane domains V and VI. More recently coupling to Gi/o α mechanisms has been demonstrated with the inhibition of forskolin stimulated cAMP and also evidence for more complicated G-protein mediated coupling mechanisms have been proposed (Francken et al. *Eur. J. Pharmacol.* 361, 299-309, 1998; Noda et al., *J. Neurochem.* 84, 222-232, 2003). Furthermore, in WO 2004/096771 it is described the use of compounds, which are active on the 5-HT$_{5A}$ serotonin receptor for the treatment of depression, anxiety disorders, schizophrenia, panic disorders, agoraphobia, social phobia, obsessive compulsive disorders, post-traumatic stress disorders, pain, memory disorders, dementia, disorders of eating behaviors, sexual dysfunction, sleep disorders, withdrawal from abuse of drugs, motor disorders such as Parkinson's disease, psychiatric disorders or gastrointestinal disorders.

The *Pharmacology & Therapeutics*, 111, 707-714 (2006) describes potential therapeutic utility of 5-HT$_{5A}$ receptor ligands for the treatment of circadian rhythm, sleep disturbances, mood disorders, schizophrenia, cognitive disorders and autism. The *Journal of Comparative Neurology*, 476, 316-329 (2004) suggests based on the localisation pattern of the 5-HT$_{5A}$ receptor in the rat spinal cord that 5-HT$_{5A}$ receptors may play a role in central motor control, nociception and autonomic function such as stress induced urinary incontinence and overactive bladder. The *Journal of Psychiatric Research*, 38, 371-376 (2004) describes evidence for a potential significant role of the 5-HT$_{5A}$ gene in schizophrenia and more specifically in patients with later age at onset.

SUMMARY OF THE INVENTION

The present invention provides compounds of formula (I)

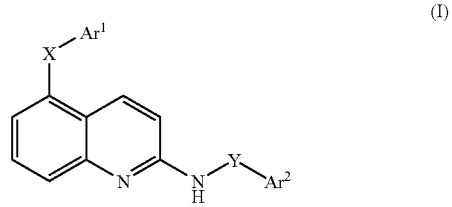

wherein
X is a bond, —CH$_2$CH$_2$—, —CH═CH—, —CH$_2$O—, —CH$_2$NR—, —CH$_2$S(O)—, —CH$_2$S(O)$_2$—, —O—, —OCH$_2$CH$_2$—, —S—, —SCH$_2$—, —OCH$_2$CH$_2$S(O)—, —OCH$_2$CH$_2$S(O)$_2$—, —CH$_2$NRCO—, —CH$_2$NRCH$_2$—,

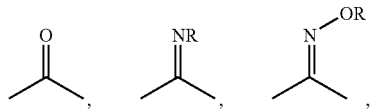

—NRS(O)$_2$NR—, —NHCHR—, —NR—, or —NRS(O)$_2$—; and wherein X can be inserted in both directions into formula (I);
Y is a bond, —CHR— or —OCH$_2$CH$_2$—;
R is hydrogen or lower alkyl;
Ar$^1$/Ar$^2$ are each independently aryl or 5 to 10 membered heteroaryl, optionally substituted by lower alkyl, lower alkoxy, lower haloalkoxy, halogen, —CF$_3$, —CH$_2$OH, —CH$_2$O-lower alkyl, 3 to 10 membered cycloalkyl, 5 to 10 membered heterocycloalkyl, —CH$_2$O(CH$_2$)$_2$O-lower alkyl, —S(O)$_2$-lower alkyl or —S(O)$_2$NHR;

or pharmaceutically acceptable acid addition salts thereof.

The compounds of formula I can contain asymmetric carbon atoms. Accordingly, the present invention includes all stereoisomeric forms of the compounds of formula I, including each of the individual enantiomers and mixtures thereof.

The invention also provides pharmaceutical compositions containing the compounds and methods for the manufacture of the compounds and compositions of the invention.

The compounds of formula I have a good activity on the 5-HT$_{5A}$ receptor. Therefore, the invention further provides methods for the treatment of depression (which term includes bipolar depression, unipolar depression, single or recurrent major depressive episodes with or without psychotic features, catatonic features, melancholic features, atypical features or postpartum onset, seasonal affective disorders and dysthymia, depressive disorders resulting from a general medical condition including, but not limited to, myocardial infarction, diabetes, miscarriage or abortion), anxiety disorders, (which includes generalized anxiety and social anxiety disorder, panic disorders, agoraphobia, social phobia, obsessive compulsive disorders, post-traumatic stress disorders, psychotic disorders (which includes schizophrenia, schizoaffective disorders, bipolar disease, mania, psychotic depression, and other psychoses involving paranoia and delusions), pain (particularly neuropathic pain), memory disorders (including dementia, amnesic disorders and age-associated memory impairment), disorders of eating behaviors (including nervosa and bulimia nervosa), sexual dysfunction, sleep disorders (including disturbances of circadian rhythm, dyssomnia, insomnia, sleep apnea and narcolepsy), withdrawal from abuse of drugs (such as of cocaine, ethanol, nicotine, benzodiazepines, alcohol, caffeine, phencyclidine and phencyclidine-like compounds, opiates such as cannabis, heroin, morphine, sedative hypnotic, amphetamine or amphetamine-related drugs), motor disorders such as Parkinson's disease, dementia in Parkinson's disease, neuroleptic-induced Parkinsonism and tardive dyskinesias, as well as other psychiatric disorders and gastrointestinal disorders such as irritable bowel syndrome (WO 2004/096771).

The preferred indications with regard to the present invention are the treatment of anxiety, depression, sleep disorders and schizophrenia.

DETAILED DESCRIPTION OF THE INVENTION

Unless otherwise stated, the following terms used in the present description have the definitions given in the following. It must be noted that, as used in the specification and the appended claims, the singular forms "a", "an," and "the" include plural forms unless the context clearly dictates otherwise.

As used herein, the term "lower alkyl" denotes a saturated straight- or branched-chain group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

The term "lower alkoxy" denotes a group wherein the alkyl residues are as defined above, and which is attached via an oxygen atom.

The term "lower haloalkoxy" denotes a $C_{1-6}$-alkoxy group as defined above which is substituted by one or more halogen. Examples of $C_{1-6}$-haloalkoxy include but are not limited to methoxy or ethoxy, substituted by one or more Cl, F, Br or I atom(s). Preferred $C_{1-6}$-haloalkoxy are difluoro- or trifluoromethoxy or ethoxy.

The term "3 to 10 membered cycloalkyl" denotes a monovalent saturated moiety, consisting of one, two or three carbon rings having 3 to 10 carbon atoms as ring members and includes but is not limited to cyclopropyl, cyclobutyl, cyclopentyl, cyclohexyl, cycloheptyl and polyspiro groups such as bicyclo[2.2.2]octanyl, bicyclo[2.2.1]heptanyl, bicyclo[3.2.1]octanyl or adamantanyl.

The term "5 to 10 membered heterocycloalkyl" means a monovalent saturated moiety, consisting of one, two or three rings, incorporating one, two, or three heteroatoms (chosen from nitrogen, oxygen or sulfur). An aryl group may be fused to one or more heterocyclic ring so long as the heterocyclic ring is a non-aromatic ring. Heterocycloalkyl can optionally be substituted with one, two, three or four substituents, wherein each substituent is independently hydroxy, alkyl, alkoxy, thioalkyl, halo, haloalkyl, hydroxyalkyl, alkoxycarbonyl, amino, alkylamino, dialkylamino, aminocarbonyl, or carbonylamino, unless otherwise specifically indicated. Examples of heterocyclic moieties include, but are not limited to, piperidinyl, piperazinyl, homopiperazinyl, azepinyl, pyrrolidinyl, pyrazolidinyl, imidazolinyl, imidazolidinyl, oxazolidinyl, isoxazolidinyl, morpholinyl, thiazolidinyl, isothiazolidinyl, quinuclidinyl, quinolinyl, isoquinolinyl, benzimidazolyl, chromanyl, thiadiazolylidinyl, benzothiazolidinyl, benzoazolylidinyl, dihydrofuryl, tetrahydrofuryl, dihydropyranyl, tetrahydropyranyl, thiomorpholinyl, dioxothiomorpholinyl thiomorpholinylsulfoxide, thiomorpholinylsulfone, dihydroquinolinyl, dihydroisoquinolinyl, tetrahydroquinolinyl, tetrahydroisoquinolinyl, 1-oxo-thiomorpholin, 1,1-dioxo-thiomorpholin, 1,4-diazepane, 1,4-oxazepane as well as those groups specifically illustrated by the examples herein below. Preferred 5 to 10 membered heterocycloalkyls are 5 or 6 membered heterocycloalkyls.

The terms "halo" and "halogen" denote chlorine, iodine, fluorine and bromine.

The term "aryl" denotes a monovalent cyclic aromatic hydrocarbon radical consisting of one or more fused rings in which at least one ring is aromatic in nature, for example phenyl or naphthyl. The phenyl group is preferred.

The term "5 to 10 membered heteroaryl" means a monocyclic, bicyclic or tricyclic radical of 5 to 10 ring atoms having at least one aromatic ring and furthermore containing one, two, or three ring heteroatoms selected from N, O, and S, the remaining ring atoms being C. Heteroaryl can optionally be substituted with one, two, three or four substituents, wherein each substituent is independently hydroxy, cyano, alkyl, alkoxy, thioalkyl, halo, haloalkyl, hydroxyalkyl, alkoxycarbonyl, amino, acetyl, —NHCOOC(CH$_3$)$_3$ or halogen substituted benzyl, or for the non aromatic part of cyclic ring also by oxo, unless otherwise specifically indicated. Examples of heteroaryl moieties include, but are not limited to, optionally substituted imidazolyl, optionally substituted thiophenyl, optionally substituted oxazolyl, optionally substituted isoxazolyl, optionally substituted thiazolyl, optionally substituted pyrazinyl, optionally substituted pyrrolyl, optionally substituted pyridinyl, optionally substituted pyrimidinyl, optionally substituted pyridazinyl, optionally substituted indolyl, optionally substituted isoindolyl, optionally substituted 2,3-dihydroindolyl, optionally substituted indazolyl, optionally substituted naphthyridinyl, optionally substituted isoquinolinyl, optionally substituted carbazol-9-yl, optionally substituted furanyl, optionally substituted benzofuranyl, optionally substituted quinolinyl, optionally substituted benzo[1,3]dioxolyl, optionally substituted benzo[1,2,3] thiadiazolyl, optionally substituted benzo[b]thiophenyl, optionally substituted 9H-thioxanthenyl, optionally substituted thieno[2,3-c]pyridinyl, optionally substituted 3H-imidazo[4,5,b]pyridinyl, optionally substituted phthalazinyl, optionally substituted 2,3-dihydrobenzo[1,4]dioxinyl, and the like or those which are specifically exemplified herein. Preferred 5 to 10 membered heteroaryls are 5 or 6 membered heteroaryls.

Even more preferred examples of "5 to 10 membered heteroaryl" include pyridyl, pyrazinyl, pyrimidinyl, pyridazinyl, triazinyl, thiazolyl, thienyl, furyl, pyrrolyl, imidazolyl, pyrazolyl, oxazolyl, isothiazolyl or isoxazolyl whereas special preference is given to furyl, pyrimidinyl, thienyl, pyridyl or imidazolyl.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluene-sulfonic acid and the like.

"Therapeutically effective amount" means an amount that is effective to prevent, alleviate or ameliorate symptoms of disease or prolong the survival of the subject being treated.

Preferred compounds of formula (I)

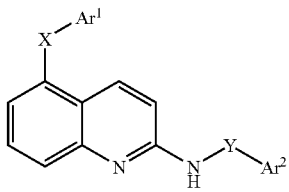

are those wherein
X is a bond, —CH$_2$CH$_2$—, —CH═CH—, —CH$_2$O—, —CH$_2$NR—, CH$_2$S(O)$_2$—, —O—, —OCH$_2$—, —OCH$_2$CH$_2$—, —S—, —SCH$_2$—, —NR—, NRCH$_2$— or —NRS(O)$_2$—;
Y is a bond, —CHR— or —OCH$_2$CH$_2$—;
R is hydrogen or lower alkyl;
Ar$^1$/Ar$^2$ are each independently (i) a monovalent cyclic aromatic hydrocarbon radical consisting of one or more fused rings in which at least one ring is aromatic in nature or (ii) a cyclic aromatic hydrocarbon radical, containing one, two or three heteroatoms, selected from the group consisting of oxygen, sulphur and nitrogen and wherein (i) and (ii) are optionally substituted by lower alkyl, lower alkoxy, halogen, —CF$_3$, —CH$_2$O H, —CH$_2$O— lower alkyl, —CH$_2$O(CH$_2$)$_2$O-lower alkyl, —S(O)$_2$-lower alkyl or —S(O)$_2$NHR;

or pharmaceutically acceptable acid addition salts thereof.

Even more preferred are compounds wherein (i) is selected from the group consisting of phenyl and naphthyl, and (ii) is selected from the group consisting of pyridyl, pyrazinyl, pyrimidinyl, pyridazinyl, triazinyl, thiazolyl, thienyl, furyl, pyrrolyl, imidazolyl, pyrazolyl, oxazolyl, isothiazolyl and isoxazolyl.

Preferred compounds of formula I are those, wherein X is —CH$_2$CH$_2$—, for example the following compounds:
(2-methoxy-benzyl)-(5-phenethyl-quinolin-2-yl)-amine,
2-methoxy-benzyl)-[5-(2-pyridin-3-yl-ethyl)-quinolin-2-yl]-amine,
(5-methyl-furan-2-ylmethyl)-(5-phenethyl-quinolin-2-yl)-amine,
(3-{2-[2-(2-methoxy-benzylamino)-quinolin-5-yl]-ethyl}-phenyl)-methanol,
{5-[2-(3-methoxymethyl-phenyl)-ethyl]-quinolin-2-yl}-(5-methyl-furan-2-ylmethyl)-amine,
3-(2-{2-[(5-methyl-furan-2-ylmethyl)-amino]-quinolin-5-yl}-ethyl)-benzenesulfonamide, and
(5-methyl-furan-2-ylmethyl)-[5-(2-pyridin-2-yl-ethyl)-quinolin-2-yl]-amine.

Preferred compounds of formula I are those, wherein X is —CH$_2$NR—, for example the following compound:
(5-methyl-furan-2-ylmethyl)-[5-(pyridin-3-ylaminomethyl)-quinolin-2-yl]-amine,
(5-methyl-furan-2-ylmethyl)-(5-phenylaminomethyl-quinolin-2-yl)-amine, and
(5-methyl-furan-2-ylmethyl)-[5-(pyridin-2-ylaminomethyl)-quinolin-2-yl]-amine.

Further preferred are compounds, wherein X is SCH$_2$, for example the following compound:
(5-benzylsulfanyl-quinolin-2-yl)-(5-methyl-furan-2-ylmethyl)-amine.

Further preferred are compounds, wherein X is —NR—, for example the following compounds:
N5-(4-fluoro-phenyl)-N2-(5-methyl-furan-2-ylmethyl)-quinoline-2,5-diamine,
N5-(4-chloro-phenyl)-N2-(5-methyl-furan-2-ylmethyl)-quinoline-2,5-diamine, and
N5-(6-chloro-pyridin-3-yl)-N2-(5-methyl-furan-2-ylmethyl)-quinoline-2,5-diamine.

Further preferred are compounds, wherein X is —NRCH$_2$—, for example the following compounds:
N2-(2-methoxy-benzyl)-N5-pyridin-3-ylmethyl-quinoline-2,5-diamine,
N5-(3-methoxy-benzyl)-N2-(2-methoxy-benzyl)-quinoline-2,5-diamine,
N2,N5-bis-(2-methoxy-benzyl)-quinoline-2,5-diamine,
N5-benzyl-N2-(2-methoxy-benzyl)-quinoline-2,5-diamine,
N2-(2-methoxy-benzyl)-N5-pyridin-4-ylmethyl-quinoline-2,5-diamine,
N5-(2-methoxy-benzyl)-N2-(5-methyl-furan-2-ylmethyl)-quinoline-2,5-diamine,
N2-(5-methyl-furan-2-ylmethyl)-N5-pyridin-3-ylmethyl-quinoline-2,5-diamine,
N5-(4-fluoro-benzyl)-N2-(5-methyl-furan-2-ylmethyl)-quinoline-2,5-diamine,
N2-(5-methyl-furan-2-ylmethyl)-N5-pyridin-2-ylmethyl-quinoline-2,5-diamine,
N5-(2-methoxy-pyridin-3-ylmethyl)-N2-(5-methyl-furan-2-ylmethyl)-quinoline-2,5-diamine,
N5-[3-(2-methoxy-ethoxy)-benzyl]-N2-(5-methyl-furan-2-ylmethyl)-quinoline-2,5-diamine,
N2-(5-methyl-furan-2-ylmethyl)-N5-(6-methyl-pyridin-2-ylmethyl)-quinoline-2,5-diamine, and
3-({2-[(5-methyl-furan-2-ylmethyl)-amino]-quinolin-5-ylamino}-methyl)-benzenesulfonamide.

Further preferred are compounds, wherein X is —NRS(O)$_2$—, for example the following compounds:
N-{2-[(5-methyl-furan-2-ylmethyl)-amino]-quinolin-5-yl}-benzenesulfonamide,
N-{2-[(5-methyl-furan-2-ylmethyl)-amino]-quinolin-5-yl}-4-fluoro-benzenesulfonamide,
5-chloro-thiophene-2-sulfonic acid {2-[(5-methyl-furan-2-ylmethyl)-amino]-quinolin-5-yl}-amide,
6-chloro-pyridine-3-sulfonic acid {2-[(5-methyl-furan-2-ylmethyl)-amino]-quinolin-5-yl}-amide,
3,5-difluoro-N-{2-[(5-methyl-furan-2-ylmethyl)-amino]-quinolin-5-yl}-benzenesulfonamide,
4-fluoro-N-[2-(2-methoxy-benzylamino)-quinolin-5-yl]-benzenesulfonamide,
3-fluoro-N-{2-[(5-methyl-furan-2-ylmethyl)-amino]-quinolin-5-yl}-benzenesulfonamide,
3,4-difluoro-N-{2-[(5-methyl-furan-2-ylmethyl)-amino]-quinolin-5-yl}-benzenesulfonamide, or
3,5-difluoro-N-[2-(2-phenoxy-ethylamino)-quinolin-5-yl]-benzenesulfonamide.

Also preferred are the following compounds:
4-Fluoro-N-[2-(2-methylsulfanyl-benzylamino)-quinolin-5-yl]-benzenesulfonamide,
[5-(2-Benzenesulfinyl-ethoxy)-quinolin-2-yl]-(2-methoxy-benzyl)-amine,
[5-(2-Benzenesulfonyl-ethoxy)-quinolin-2-yl]-(2-methoxy-benzyl)-amine,
3,5-Difluoro-N-{2-[(5-methyl-thiophen-2-ylmethyl)-amino]-quinolin-5-yl}-benzenesulfonamide,
3,5-Difluoro-N-{2-[1-(5-methyl-furan-2-yl)-ethylamino]-quinolin-5-yl}-benzenesulfonamide,
N5-(1H-Imidazol-4-ylmethyl)-N2-(5-methyl-furan-2-ylmethyl)-quinoline-2,5-diamine, N2-(5-Methyl-furan-2-ylmethyl)-N5-(1H-pyrazol-3-ylmethyl)-quinoline-2,5-diamine,
N5-(1H-Indol-4-ylmethyl)-N2-(5-methyl-furan-2-ylmethyl)-quinoline-2,5-diamine,
3,5-Difluoro-N-[2-(2-methyl-benzofuran-7-ylamino)-quinolin-5-yl]-benzenesulfonamide,
N2-(5-Methyl-furan-2-ylmethyl)-N5-(2-methyl-1H-imidazol-4-ylmethyl)-quinoline-2,5-diamine,
N2-(5-Methyl-furan-2-ylmethyl)-N5-(1-methyl-1H-pyrrol-2-ylmethyl)-quinoline-2,5-diamine,
N5-(1H-Indol-4-yl)-N2-(5-methyl-furan-2-ylmethyl)-quinoline-2,5-diamine,
N5-(1H-Indol-7-yl)-N2-(5-methyl-furan-2-ylmethyl)-quinoline-2,5-diamine,
N2-(5-Methyl-furan-2-ylmethyl)-N5-(5-methyl-1H-imidazol-4-ylmethyl)-quinoline-2,5-diamine,
N2-(2-Methoxy-benzyl)-N5-(1H-pyrazol-3-ylmethyl)-quinoline-2,5-diamine,
N2-(2-Methoxy-benzyl)-N5-(2-methyl-3H-imidazol-4-ylmethyl)-quinoline-2,5-diamine,
N2-(2-Methoxy-benzyl)-N5-(5-methyl-3H-imidazol-4-ylmethyl)-quinoline-2,5-diamine,
N5-(3H-Imidazol-4-ylmethyl)-N2-(2-methoxy-benzyl)-quinoline-2,5-diamine,
N2-(5-Methyl-furan-2-ylmethyl)-N5-thiazol-2-ylmethyl-quinoline-2,5-diamine,
N2-(2,6-Dimethoxy-benzyl)-N5-pyridin-3-ylmethyl-quinoline-2,5-diamine,
N5-(1H-Indol-4-ylmethyl)-N2-(2-methoxy-benzyl)-quinoline-2,5-diamine,
N5-Benzo[1,3]dioxol-4-ylmethyl-N2-(5-methyl-furan-2-ylmethyl)-quinoline-2,5-diamine,
N5-(4-Methyl-3,4-dihydro-2H-benzo[1,4]oxazin-7-ylmethyl)-N2-(5-methyl-furan-2-ylmethyl)-quinoline-2,5-diamine,
N2-(5-Methyl-furan-2-ylmethyl)-N5-[2-(4-methyl-piperazin-1-yl)-benzyl]-quinoline-2,5-diamine,
N2-(2-Methoxy-benzyl)-N5-(1H-[1,2,3]triazol-4-ylmethyl)-quinoline-2,5-diamine,
N5-(1H-Benzoimidazol-5-ylmethyl)-N2-(5-methyl-furan-2-ylmethyl)-quinoline-2,5-diamine,
4-Fluoro-N-[2-(2-trifluoromethoxy-benzylamino)-quinolin-5-yl]-benzenesulfonamide,
N2-(2,6-Dimethoxy-benzyl)-N5-(1H-indol-4-ylmethyl)-quinoline-2,5-diamine,
N2-(2-Methoxy-benzyl)-N5-thiazol-2-ylmethyl-quinoline-2,5-diamine,
N5-(1H-Indol-4-ylmethyl)-N2-(2-methyl-benzofuran-7-yl)-quinoline-2,5-diamine,
N2-(5-Methyl-furan-2-ylmethyl)-N5-(5-methyl-1H-pyrazol-3-yl)-quinoline-2,5-diamine,
N5-(1H-Indol-4-yl)-N2-(2-methyl-benzofuran-7-yl)-quinoline-2,5-diamine,
N5-(3H-Benzoimidazol-5-ylmethyl)-N2-(2-methoxy-benzyl)-quinoline-2,5-diamine,
N2-(5-Methyl-furan-2-ylmethyl)-N5-(3H-[1,2,3]triazol-4-ylmethyl)-quinoline-2,5-diamine,
N5-(1H-Indol-4-ylmethyl)-N2-(2-trifluoromethoxy-benzyl)-quinoline-2,5-diamine,
N5-(1H-Benzoimidazol-5-ylmethyl)-N2-(2-trifluoromethoxy-benzyl)-quinoline-2,5-diamine,
N2-(2,3-Dihydro-benzo[1,4]dioxin-5-ylmethyl)-N5-(1H-indol-4-ylmethyl)-quinoline-2,5-diamine,
N5-(7-Fluoro-1H-indol-4-yl)-N2-(5-methyl-furan-2-ylmethyl)-quinoline-2,5-diamine,
N5-(3,5-Difluoro-benzyl)-N2-(5-methyl-furan-2-ylmethyl)-quinoline-2,5-diamine,
N-[2-(2,3-Dihydro-benzo[1,4]dioxin-5-ylamino)-quinolin-5-yl]-3,5-difluoro-benzenesulfonamide,
3,5-Difluoro-N-[2-(naphthalen-1-ylamino)-quinolin-5-yl]-benzenesulfonamide,
3,5-Difluoro-N-[2-(indan-4-ylamino)-quinolin-5-yl]-benzenesulfonamide,
N5-(1H-Benzoimidazol-5-ylmethyl)-N2-(2-methyl-benzofuran-7-yl)-quinoline-2,5-diamine,
N2-(2-Methyl-benzofuran-7-yl)-N5-(5-methyl-3H-imidazol-4-ylmethyl)-quinoline-2,5-diamine,
4-Fluoro-N-{2-[(5-methyl-furan-2-ylmethyl)-amino]-quinolin-5-ylmethyl}-benzamide,
{5-[(4-Fluoro-benzylamino)-methyl]-quinolin-2-yl}-(5-methyl-furan-2-ylmethyl)-amine,
4-Fluoro-N-[2-(2-methyl-benzofuran-7-ylamino)-quinolin-5-yl]-benzenesulfonamide,
N2-(2-Methyl-benzofuran-7-yl)-N5-pyridin-3-ylmethyl-quinoline-2,5-diamine,
5-Chloro-thiophene-2-sulfonic acid [2-(2-methyl-benzofuran-7-ylamino)-quinolin-5-yl]-amide,
N5-(3H-Imidazol-4-ylmethyl)-N2-(2-methyl-benzofuran-7-yl)-quinoline-2,5-diamine,
N5-(3,5-Difluoro-benzyl)-N2-(2-methyl-benzofuran-7-yl)-quinoline-2,5-diamine,
N5-(4-Fluoro-phenyl)-N2-(2-methyl-benzofuran-7-yl)-quinoline-2,5-diamine,
rac-3,5-Difluoro-N-[2-(2-methyl-2,3-dihydro-benzofuran-7-ylamino)-quinolin-5-yl]-benzenesulfonamide,
rac-N2-(5-Methyl-furan-2-ylmethyl)-N5-thiochroman-4-yl-quinoline-2,5-diamine,
{5-[(4-Fluoro-phenyl)-imino-methyl]-quinolin-2-yl}-(2-methoxy-benzyl)-amine,
(4-Fluoro-phenyl)-[2-(2-methoxy-benzylamino)-quinolin-5-yl]-methanone,
N-[2-(2-tert-Butyl-benzofuran-7-ylamino)-quinolin-5-yl]-3,5-difluoro-benzenesulfonamide,
N-[2-(2,3-Dihydro-benzofuran-7-ylamino)-quinolin-5-yl]-3,5-difluoro-benzenesulfonamide,
N5-(1H-Indol-4-ylmethyl)-N2-(2-methyl-2,3-dihydro-benzofuran-7-yl)-quinoline-2,5-diamine,
N-[2-(2,2-Dimethyl-2,3-dihydro-benzofuran-7-ylamino)-quinolin-5-yl]-3,5-difluoro-benzenesulfonamide
rac-N5-Chroman-4-yl-N2-(5-methyl-furan-2-ylmethyl)-quinoline-2,5-diamine,
rac-5-(1,1-Dioxo-1l6-thiochroman-4-yl)-N2-(5-methyl-furan-2-ylmethyl)-quinoline-2,5-diamine,
rac-N2-(2,2-Dimethyl-2,3-dihydro-benzofuran-7-yl)-N5-(1,1-dioxo-1l6-thiochroman-4-yl)-quinoline-2,5-diamine,
N-(2-{[(5-methyl-2-furyl)methyl]amino}quinolin-5-yl)-N'-phenylsulfamide,
4-Fluoro-N-[2-(2-methoxy-benzylamino)-quinolin-5-ylmethyl]-benzamide,
N2-(2,2-Dimethyl-2,3-dihydro-benzofuran-7-yl)-N5-(1H-indol-4-ylmethyl)-quinoline-2,5-diamine,
N5-(1H-Benzoimidazol-5-ylmethyl)-N2-(2,2-dimethyl-2,3-dihydro-benzofuran-7-yl)-quinoline-2,5-diamine,
N2-(2,2-Dimethyl-2,3-dihydro-benzofuran-7-yl)-N5-(5-methyl-3H-imidazol-4-ylmethyl)-quinoline-2,5-diamine,
(2-Methoxy-benzyl)-[5-(5-methyl-[1,2,4]oxadiazol-3-yl)-quinolin-2-yl]-amine,
rac-N5-[1-(3,5-Difluoro-phenyl)-ethyl]-N2-(2,2-dimethyl-2,3-dihydro-benzofuran-7-yl)-quinoline-2,5-diamine,
(R)— or (S)—N5-((S)-1,1-Dioxo-1l6-thiochroman-4-yl)-N2-(5-methyl-furan-2-ylmethyl)-quinoline-2,5-diamine,
(R)— or (S)—N5-((S)-1,1-Dioxo-1l6-thiochroman-4-yl)-N2-(5-methyl-furan-2-ylmethyl)-quinoline-2,5-diamine, N-(2-{[(5-methyl-2-furyl)methyl]amino}quinolin-5-yl)-N'-(4-fluorophenyl)sulfamide,
3,5-Difluoro-N-[2-(3-methoxy-phenylamino)-quinolin-5-yl]-benzenesulfonamide,
N-{2-[(2,2-dimethyl-2,3-dihydro-1-benzofuran-7-yl)amino]quinolin-5-yl}-N'-(4-fluorophenyl)sulfamide,
3,5-Difluoro-N-(2-m-tolylamino-quinolin-5-yl)-benzenesulfonamide,
(+)-N5-[1-(3,5-Difluoro-phenyl)-ethyl]-N2-(2,2-dimethyl-2,3-dihydro-benzofuran-7-yl)-quinoline-2,5-diamine,
N-[2-(3-Cyclopropyl-phenylamino)-quinolin-5-yl]-3,5-difluoro-benzenesulfonamide,
rac-N2-(2,2-Dimethyl-2,3-dihydro-benzofuran-7-yl)-N5-(1-thiazol-2-yl-ethyl)-quinoline-2,5-diamine,
N-[2-(3-tert-Butyl-phenylamino)-quinolin-5-yl]-3,5-difluoro-benzenesulfonamide,
rac-N2-(2,2-Dimethyl-2,3-dihydro-benzofuran-7-yl)-N5-(1-pyridin-3-yl-ethyl)-quinoline-2,5-diamine,
N2-(2,2-Dimethyl-2,3-dihydro-benzofuran-7-yl)-N5-pyridin-3-ylmethyl-quinoline-2,5-diamine,
N2-(3-Cyclopropyl-phenyl)-N5-(1H-indol-4-ylmethyl)-quinoline-2,5-diamine,
N5-(1H-Benzoimidazol-5-ylmethyl)-N2-(3-cyclopropyl-phenyl)-quinoline-2,5-diamine,
N2-(3-Cyclopropyl-phenyl)-N5-(5-methyl-3H-imidazol-4-ylmethyl)-quinoline-2,5-diamine, and
(4-Fluoro-phenyl)-[2-(2-methoxy-benzylamino)-quinolin-5-yl]-methanone oxime.

Further, preferred compounds of general formula (I) are those of general formula (Ia)

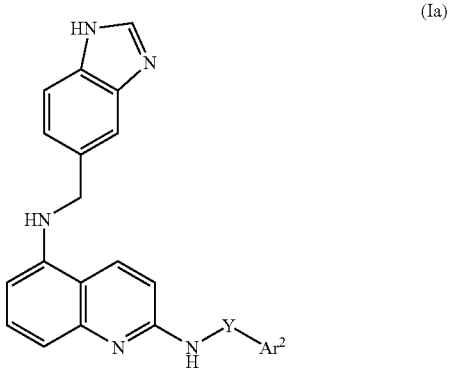

(Ia)

wherein
Y is a bond, —CHR— or —OCH$_2$CH$_2$—; and wherein X can be inserted in both directions into formula (I); and
Ar$^2$ is aryl or 5 to 10 membered heteroaryl, optionally substituted by lower alkyl, lower alkoxy, lower haloalkoxy, halogen, —CF$_3$, —CH$_2$OH, —CH$_2$O-lower alkyl, 3 to 10 membered cycloalkyl, 5 to 10 membered heterocycloalkyl, —CH$_2$O(CH$_2$)$_2$O-lower alkyl, —S(O)$_2$-lower alkyl or —S(O)$_2$NHR.

Special preference is given to the compounds of general formula (Ia) which are selected from the group consisting of:
N5-(1H-Benzoimidazol-5-ylmethyl)-N2-(5-methyl-furan-2-ylmethyl)-quinoline-2,5-diamine,
N5-(3H-Benzoimidazol-5-ylmethyl)-N2-(2-methoxy-benzyl)-quinoline-2,5-diamine,
N5-(1H-Benzoimidazol-5-ylmethyl)-N2-(2-trifluoromethoxy-benzyl)-quinoline-2,5-diamine,
N5-(1H-Benzoimidazol-5-ylmethyl)-N2-(2-methyl-benzofuran-7-yl)-quinoline-2,5-diamine,
N5-(1H-Benzoimidazol-5-ylmethyl)-N2-(2,2-dimethyl-2,3-dihydro-benzofuran-7-yl)-quinoline-2,5-diamine, and
N5-(1H-Benzoimidazol-5-ylmethyl)-N2-(3-cyclopropyl-phenyl)-quinoline-2,5-diamine.

Further, preferred compounds of general formula (I) are those of general formula (Ib)

(Ib)

wherein
Y is a bond, —CHR— or —OCH$_2$CH$_2$—; and wherein X can be inserted in both directions into formula (I); and
Ar$^2$ is aryl or 5 to 10 membered heteroaryl, optionally substituted by lower alkyl, lower alkoxy, lower haloalkoxy, halogen, —CF$_3$, —CH$_2$OH, —CH$_2$O-lower alkyl, 3 to 10 membered cycloalkyl, 5 to 10 membered heterocycloalkyl, —CH$_2$O(CH$_2$)$_2$O-lower alkyl, —S(O)$_2$-lower alkyl or —S(O)$_2$NHR.

Special preference is given to the compounds of general formula (Ia) which are selected from the group consisting of:
N5-(1H-Indol-4-ylmethyl)-N2-(5-methyl-furan-2-ylmethyl)-quinoline-2,5-diamine,
N5-(1H-Indol-4-ylmethyl)-N2-(2-methoxy-benzyl)-quinoline-2,5-diamine,
N2-(2,6-Dimethoxy-benzyl)-N5-(1H-indol-4-ylmethyl)-quinoline-2,5-diamine,
N5-(1H-Indol-4-ylmethyl)-N2-(2-methyl-benzofuran-7-yl)-quinoline-2,5-diamine,
N5-(1H-Indol-4-ylmethyl)-N2-(2-trifluoromethoxy-benzyl)-quinoline-2,5-diamine,
N2-(2,3-Dihydro-benzo[1,4]dioxin-5-ylmethyl)-N5-(1H-indol-4-ylmethyl)-quinoline-2,5-diamine,
N5-(1H-Indol-4-ylmethyl)-N2-(2-methyl-2,3-dihydro-benzofuran-7-yl)-quinoline-2,5-diamine,
N2-(2,2-Dimethyl-2,3-dihydro-benzofuran-7-yl)-N5-(1H-indol-4-ylmethyl)-quinoline-2,5-diamine, and
N2-(3-Cyclopropyl-phenyl)-N5-(1H-indol-4-ylmethyl)-quinoline-2,5-diamine.

The present compounds of formula I and their pharmaceutically acceptable salts can be prepared by methods known in the art, for example by a process described below, which process comprises a) reacting a compound of formula

3 with an amine of formula

 4 to obtain a compound of formula

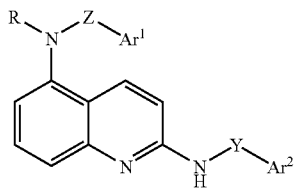 I-1 wherein R is hydrogen or lower alkyl, Z is a bond, $CH_2$ or $S(O)_2$ and the other definitions are as described above, or b) reacting a compound of formula

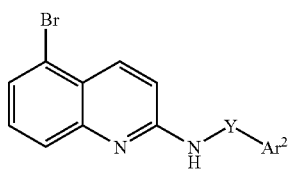 3 with a compound of formula

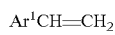 5 to obtain a compound of formula

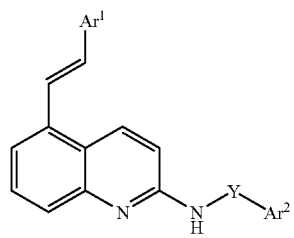 I-2 wherein the definitions are as described above, or c) reacting a compound of formula

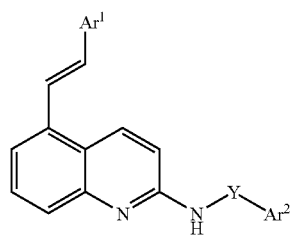 I-2 with hydrogen
to obtain a compound of formula

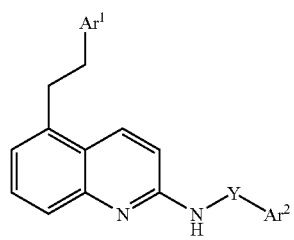 I-3 wherein the definitions are as described above, or d) reacting a compound of formula

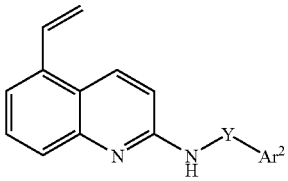 7 with a compound of formula $Ar^1hal$ 8 to obtain a compound of formula

I-2 wherein hal is bromine or iodine and the other definitions are as described above, or e) reacting a compound of formula

9 with a compound of formula $Ar^1NHR$ 10 to obtain a compound of formula

I-4 wherein R is hydrogen or lower alkyl and the other definitions are as described above, or f) reacting a compound of formula

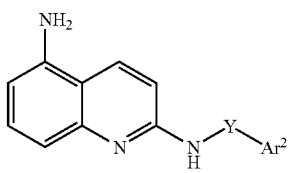

with a compound of formula Ar¹CHO to obtain a compound of formula

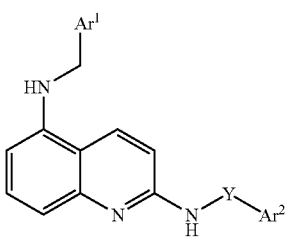

wherein the definitions are as described above, or g) reacting a compound of formula

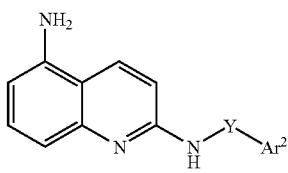

with a compound of formula Ar¹ halogen to obtain a compound of formula

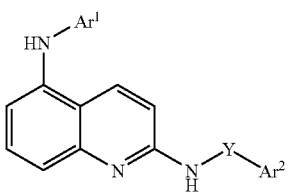

wherein the definitions are as described above, or h) reacting a compound of formula

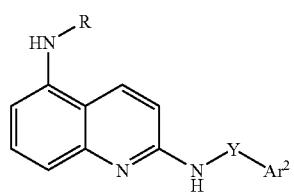

with a compound of formula Ar¹SO₂Cl to obtain a compound of formula

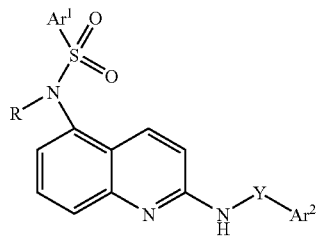

wherein R is hydrogen or lower alkyl and the other definitions are as described above, or i) reacting a compound of formula

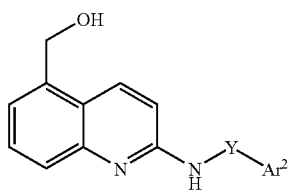

with a compound of formula Ar¹OH to obtain a compound of formula

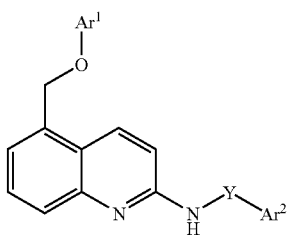

wherein the definitions are as described above, or j) reacting a compound of formula

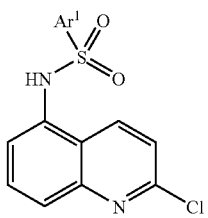

with a compound of formula Ar²YNH₂ to obtain a compound of formula

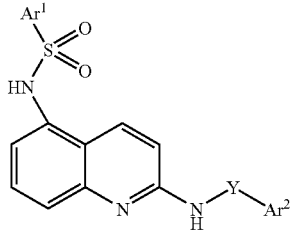

wherein the definitions are as described above, or k) reacting a compound of formula

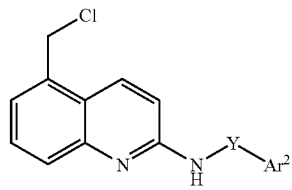

with a compound of formula Ar¹SO₂Na to obtain a compound of formula

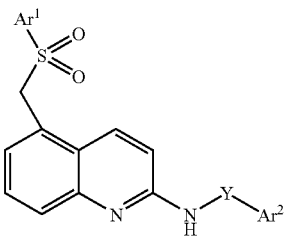

wherein the definitions are as described above, or l) reacting a compound of formula

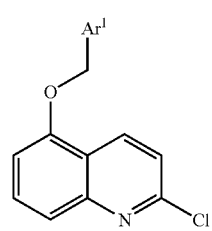

with a compound of formula Ar²YNH₂ to obtain a compound of formula

I-9

I-11

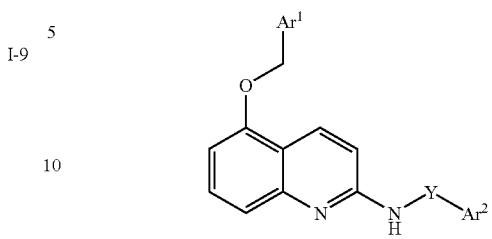

wherein the definitions are as described above, and m) reacting a compound of formula

3

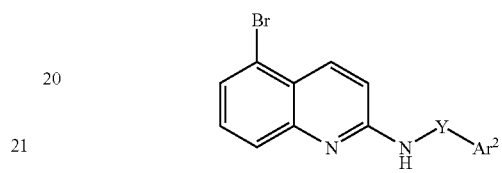

with a compound of formula Ar¹B(OH)₂ 28 to obtain a compound of formula

I-13

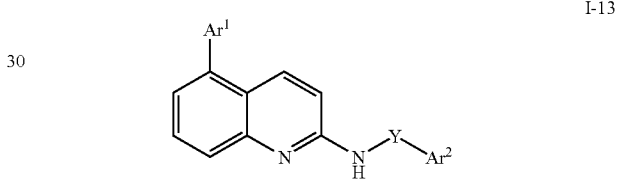

wherein the definitions are as described above, n) reacting a compound of formula

I-10

30

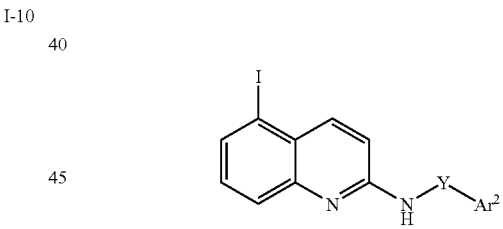

with a compound of formula Ar¹ZSH 31 to obtain a compound of formula

I-14

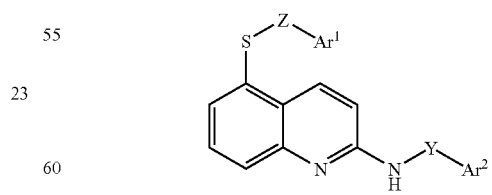

23 wherein Z is a bond or CH₂ and the other definitions are as described above, if desired, converting the compounds obtained into pharmaceutically acceptable acid addition salts.

In examples 1-81 and in the following schemes 1 to 17 the preparation of compounds of formula I are described in more detail. The starting materials are known compounds or may be prepared according to methods known in the art.

Compounds of formula I may be prepared in accordance with the following routes:

Route 1 according to scheme 1 is described in examples 1, 5-10, 13, 15, 20, 24, 25, 27-30, 35, 40, 42, 45, 49, 51, 52, 57, 59, 60, 62, 69, 70, 72, 77 and 78 for X being —NR—, NRCH$_2$— or —NRS(O)$_2$—;

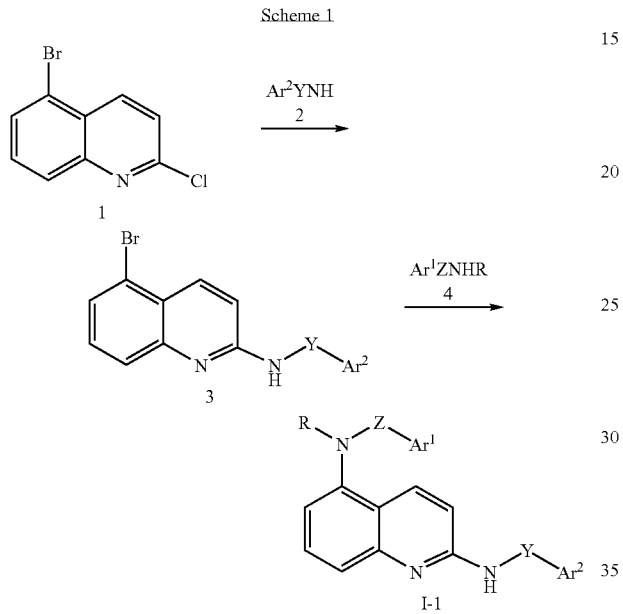

wherein R is lower alkyl or hydrogen, Z is a bond, CH$_2$, or S(O)$_2$ and the remaining definitions are as described above; 5-Bromo-2-chloroquinoline (1) is reacted with 2 equivalents of an amine of formula Ar$^2$YNH$_2$ (2) without a solvent. Intermediate 3 is reacted with an amine Ar$^1$ZNHR (4) in a palladium catalyzed substitution reaction to a compound of formula I-1.

Route 2 according to scheme 2 is described in examples 2, 14, 43 and 44 for X being —CH═CH— and the other definitions are as described above.

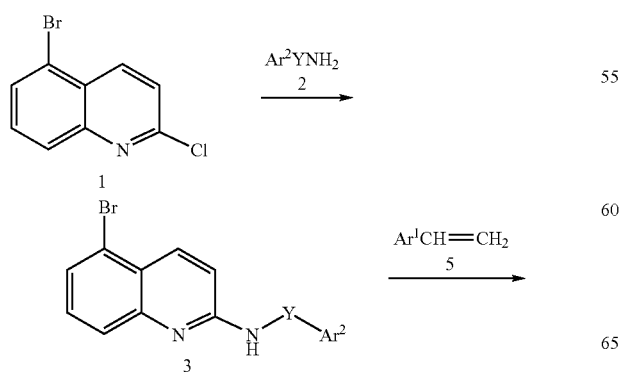

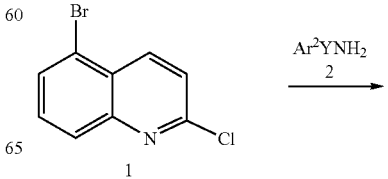

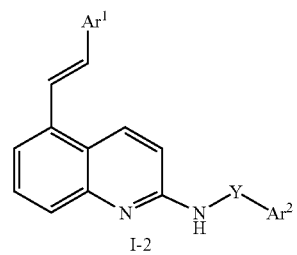

5-Bromo-2-chloroquinoline (1) is reacted with 2 equivalents of an amine Ar$^2$YNH$_2$ (2) without a solvent. Intermediate 3 is reacted with an alkene of formula Ar$^1$CHCH$_2$ (5) in a palladium catalyzed substitution reaction to a compound of formula I-2.

Route 3 according to scheme 3 is described in examples 4, 16, 17, 18, 23, 33, 34, 54 and 55 for X being —CH$_2$CH$_2$— and the other definitions are as described above.

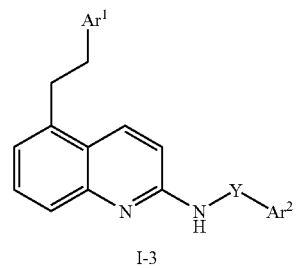

Compounds of formula I-2 are reacted with hydrogen in presence of a palladium catalyst to a compound of formula I-3.

Route 4 describes compounds according to scheme 4 as described in examples 11, 12, 19, 31 and 32 for X being —CH═CH— and the other definitions are as described above.

-continued

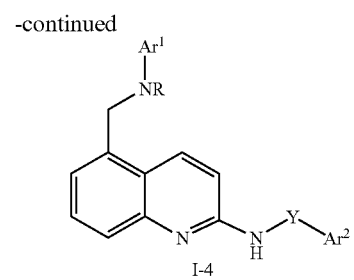

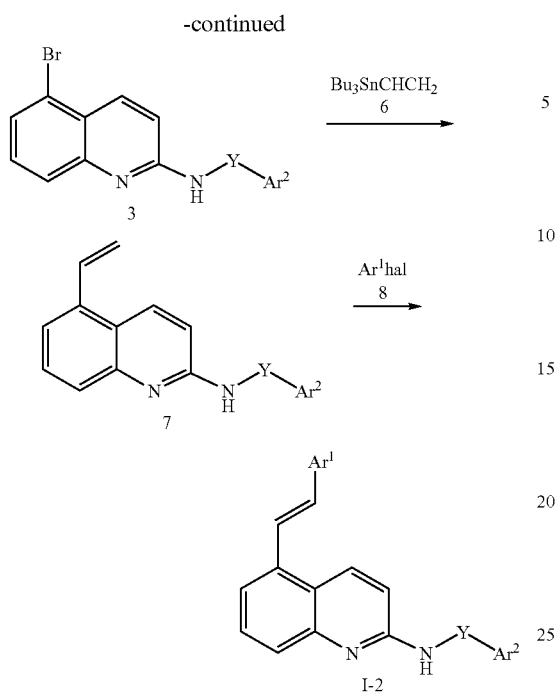

5-Bromo-2-chloroquinoline (1) is reacted with 2 equivalents of an amine of formula $Ar^2YNH_2$ (2) without a solvent. Intermediate (3) is reacted with an vinyltributyltin (6) in a palladium catalyzed substitution reaction. Intermediate (7) is reacted with an arylbromide or aryliodide $Ar^1hal$ (8) in a palladium catalyzed substitution reaction.

Route 5 describes compounds according to scheme 5 as described in example 21, 22, 36 and 37 for X being —$CH_2NR$— and the other definitions are as described above.

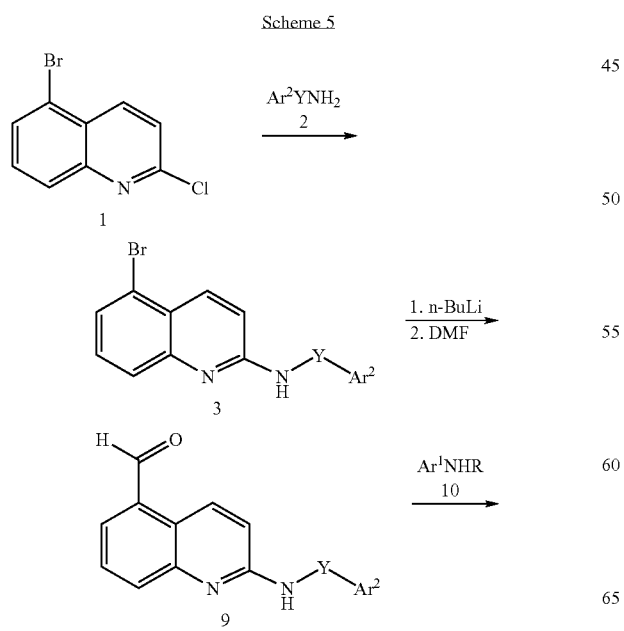

5-Bromo-2-chloroquinoline (1) is reacted with 2 equivalents of an amine of formula $Ar^2YNH_2$ (2) without a solvent. Intermediate 3 is reacted with n-butyllithium and quenched with dimethylformamide to produce an aldehyde of formula (9). Aldehyde (9) is reacted with an amine $Ar^1NH_2$ (10) in a reductive amination to obtain a compound of formula I-4.

Route 6 describes intermediates according to scheme 6 used in example 25 for X being —$NH_2CH_2$— and the other definitions are as described above.

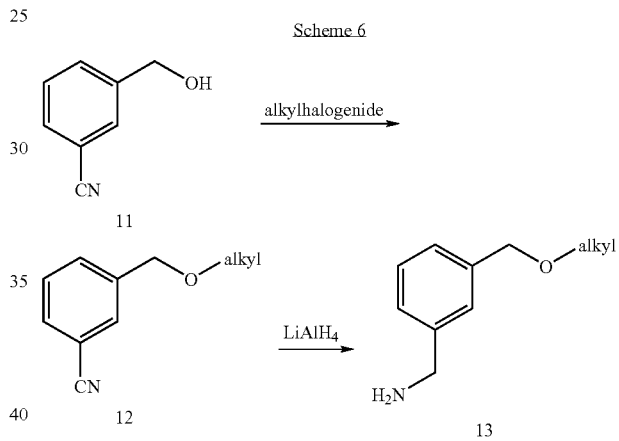

An alcohol (11) is alkylated with an alkylbromide or alkylchloride. The intermediate (12) is reduced with lithium aluminum hydride to the amine (13).

Route 7 describes compounds according to scheme 7 as described in example 26 for X being —$NH_2CH_2$— and the other definitions are as described above.

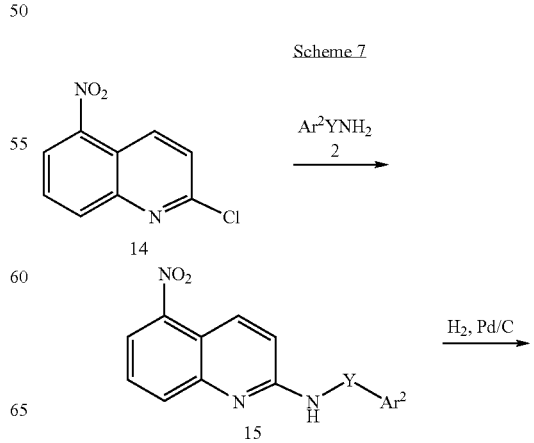

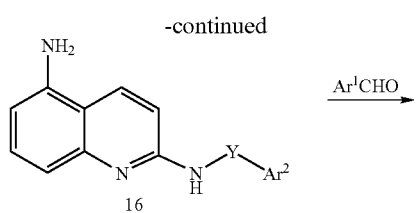

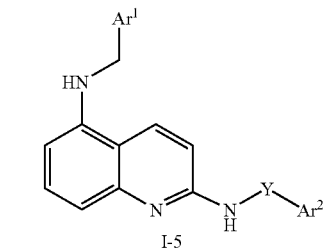

5-Nitro-2-chloroquinoline (14) is reacted with 2 equivalents of an amine of formula Ar²YNH₂ (2) without a solvent. The nitro group in the intermediate 15 is reduced with hydrogen to the amine of formula (16). The amine (16) is reductively aminated with an aldehyde Ar¹CHO to a compound of formula I-5.

Route 8 describes compounds according to scheme 8 as described in example 38 for X being —NH— and the other definitions are as described above.

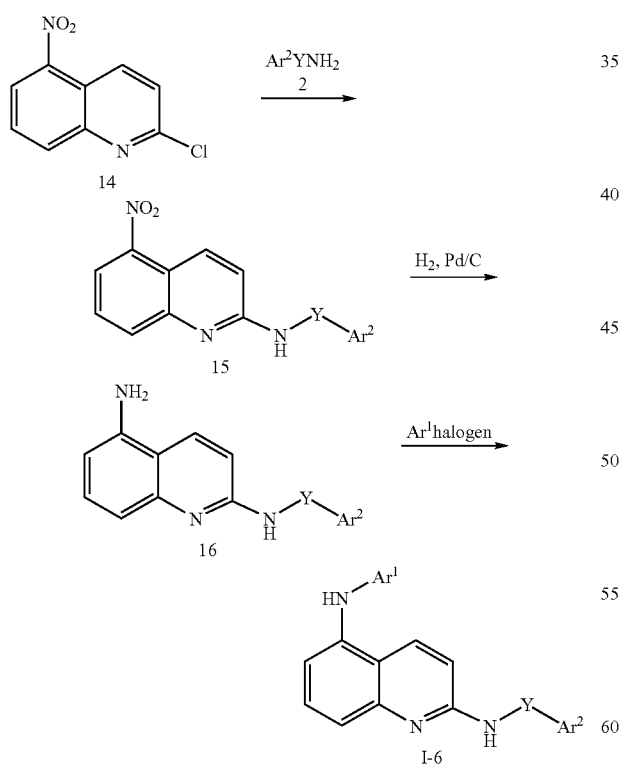

5-Nitro-2-chloroquinoline (14) is reacted with 2 equivalents of an amine of formula Ar²YNH₂ (2) without a solvent. The nitro group in compound (15) is reduced with hydrogen to the amine of formula (16). Amine 16 is reacted with an aromatic bromide or iodide (Ar¹ halogen) in a palladium catalyzed substitution reaction to obtain a compound of formula I-6.

Route 9 describes compounds according to scheme 9 as described in examples 39, 50, 58, 73 and 74 for X being —NHS(O)₂ and the other definitions are as described above.

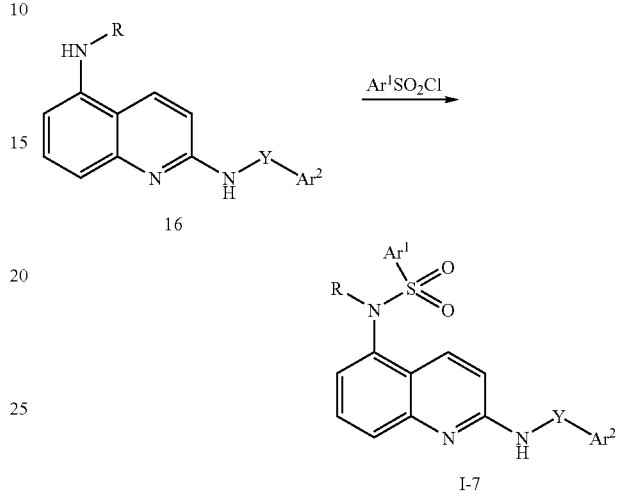

Intermediate of formula (16) is reacted with an aromatic sulfonylchloride in dimethylformamide to obtain a compound of formula I-7.

Route 10 describes compounds according to scheme 10 as described in example 41 for X being —CH₂O— and the other definitions are as described above.

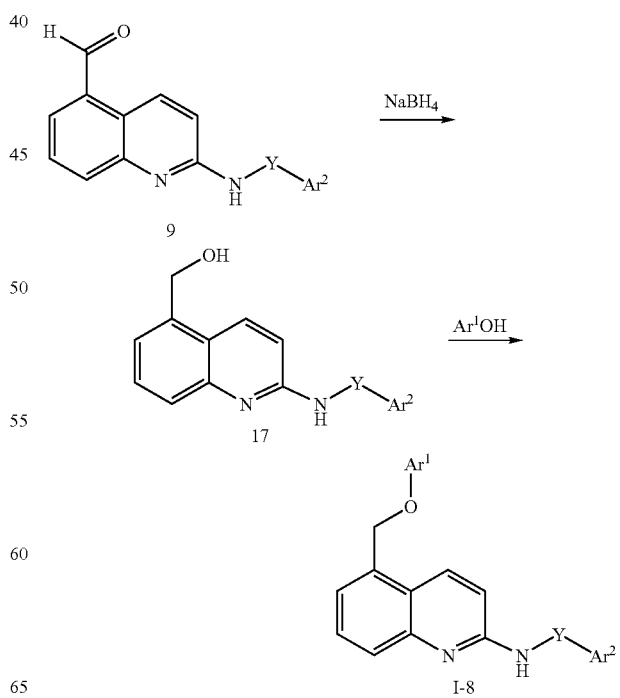

Aldehyde of formula (9) is reduced with sodium borohydride to the an alcohol of formula (17). Alcohol (17) is then reacted in a Mitsunobu reaction with a phenol derivative Ar$^1$OH to give a compound of formula I-8.

Route 11 describes compounds according to scheme 11 as described in example 50 for X being —N(Me)S(O)$_2$ and the other definitions are as described above.

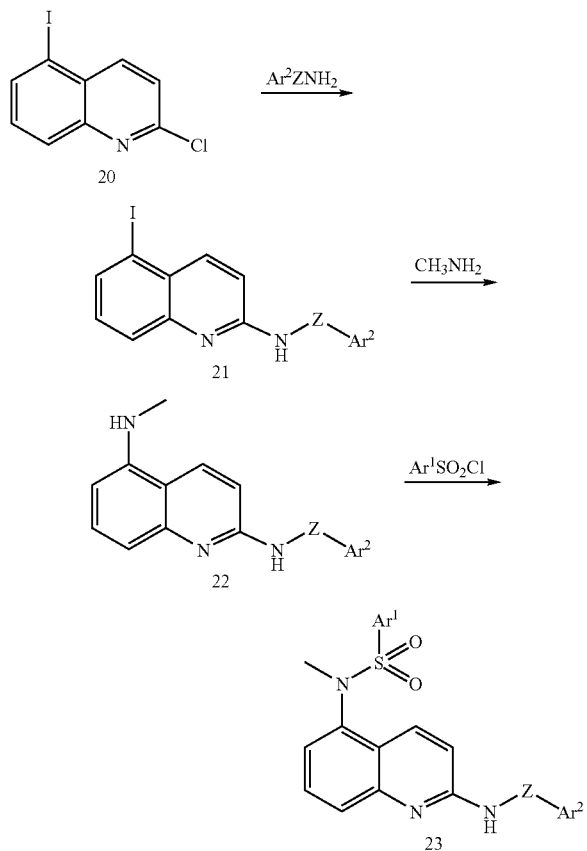

5-Iodo-2-chloroquinoline (20) is reacted with 2 equivalents of an amine (Ar$^2$ZNH$_2$) without solvent. Intermediate 21 is reacted with an amine (CH$_3$NH$_2$) in a palladium catalyzed substitution reaction. Intermediate 22 is reacted with a sulfonylchloride (Ar$^1$SO$_2$Cl) to give a compound 23.

Route 12 describes compounds according to scheme 12 as described in example 58 for X being —NHS(O)$_2$ and the other definitions are as described above.

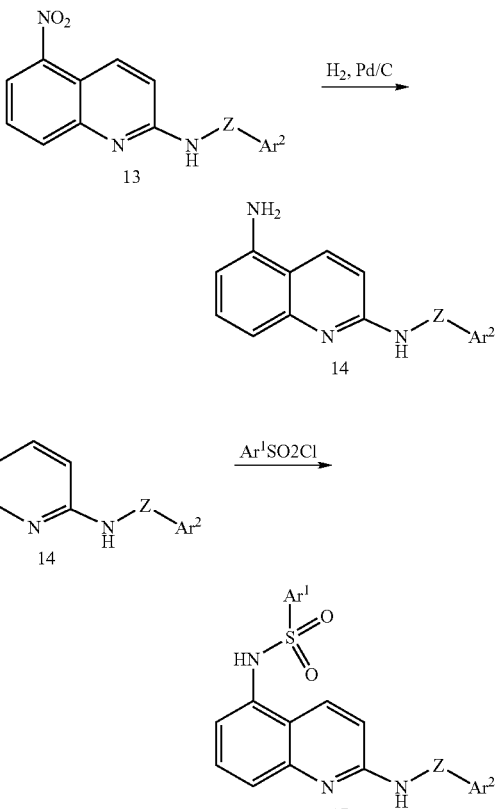

5-Nitro-2-chloroquinoline (12) is reacted with 2 equivalents of an amine (Ar$^2$ZNH$_2$) without solvent. The nitro group in 13 is reduced with hydrogen to the amine 14. Amine 14 is reacted with a sulfonylchloride (Ar$^1$SO$_2$Cl) in pyridine to give a compound 17.

Route 13 describes compounds according to scheme 13 as described in example 61, 80 and 81 for X being —NHS(O)$_2$ and the other definitions are as described above.

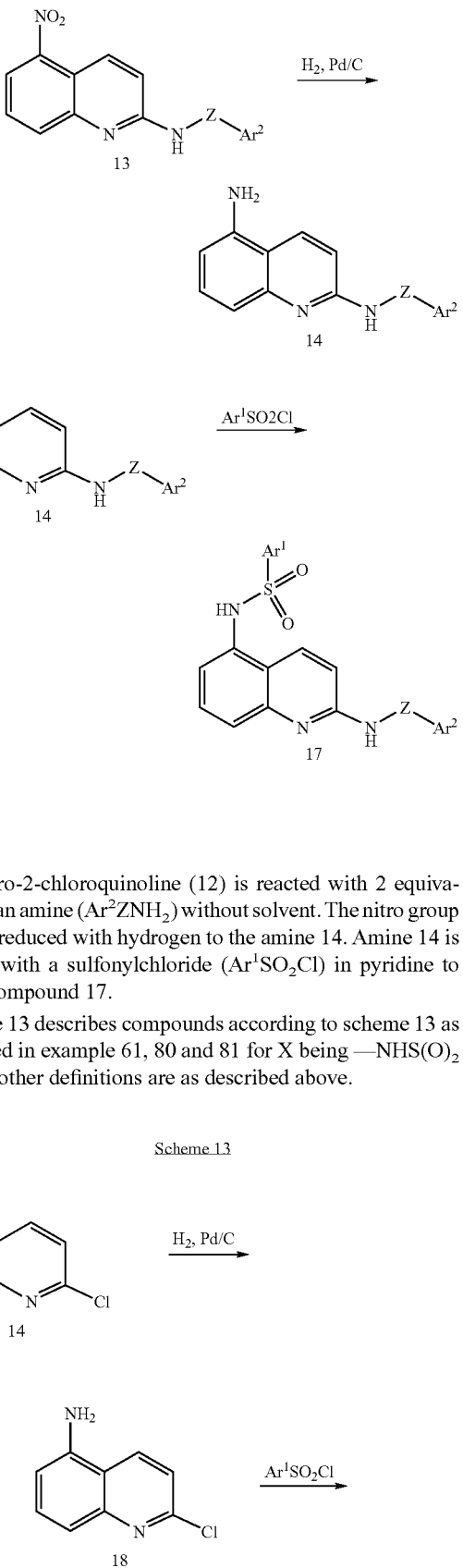
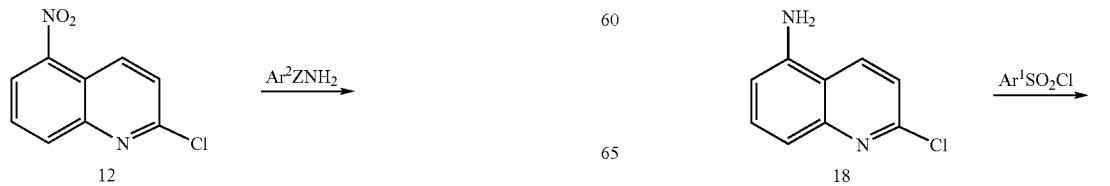

-continued

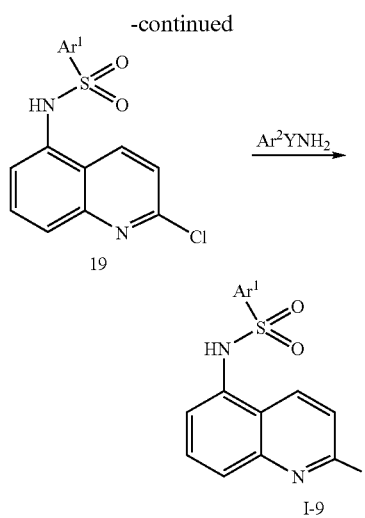

19

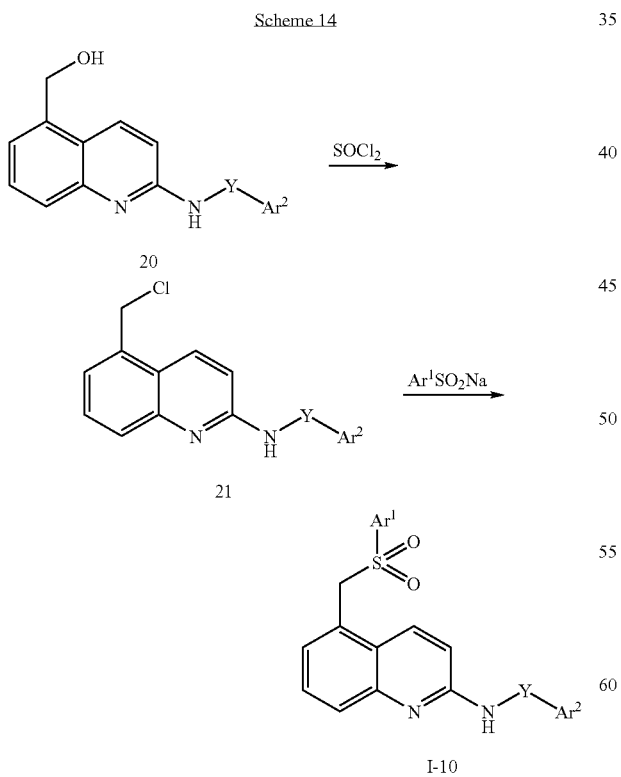

5-Nitro-2-chloroquinoline (14) is reduced with hydrogen and a palladium catalyst to the amine of formula (18). Amine (18) is reacted with a sulfonylchloride of formula Ar¹SO₂Cl in pyridine. Intermediate (19) is reacted with 2 equivalents of an amine of formula Ar²YNH₂ without a solvent to give a compound of formula I-9.

Route 14 describes compounds according to scheme 14 as described in example 76 for X being —CH₂S(O)₂— and the other definitions are as described above.

reacted with a sulfinic acid sodium salt of formula Ar¹SO₂Na to the sulfone of formula I-10.

Route 15 describes compounds according to scheme 15 as described in example 63, 64, 65, 66, 67, 68, 71 or 79 for X being —OCH₂— or —OCH₂CH₂— and the other definitions are as described above.

Scheme 15

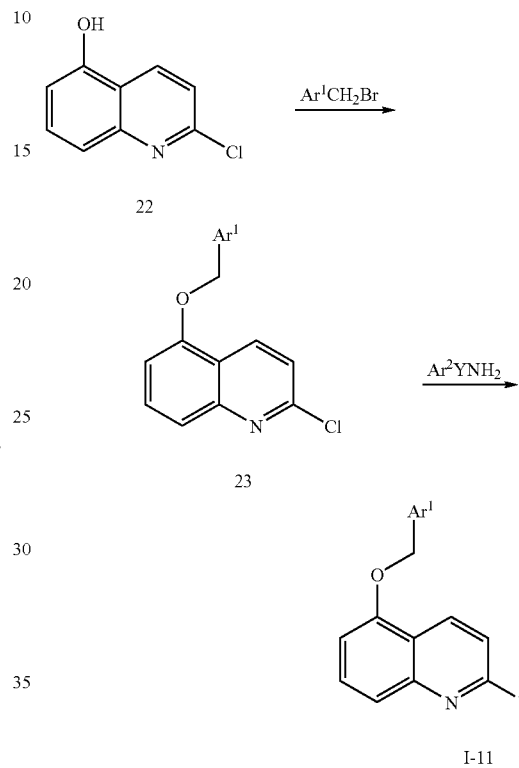

5-Hydroxy-quinoline (22) is benzylated and subsequently reacted with an amine of formula NH₂YAr² to obtain a compound of formula I-11.

Route 16 describes compounds according to scheme 16 as described in example 47 and 48 for X being —OCH₂— and the other definitions are as described above.

Scheme 16

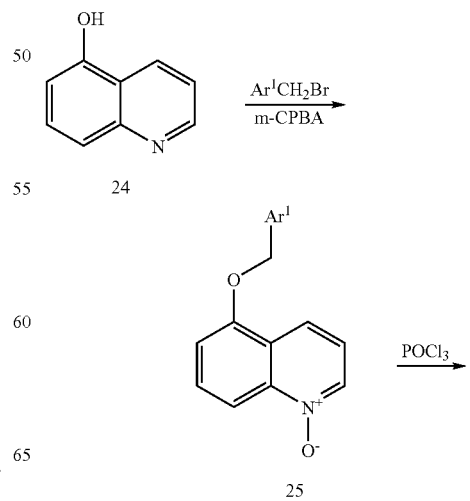

An alcohol of formula (20) is converted to the chloride of formula (21) by treatment with thionylchloride which is

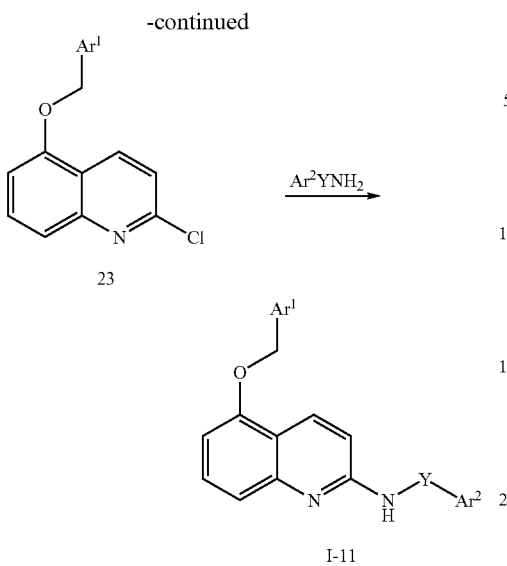

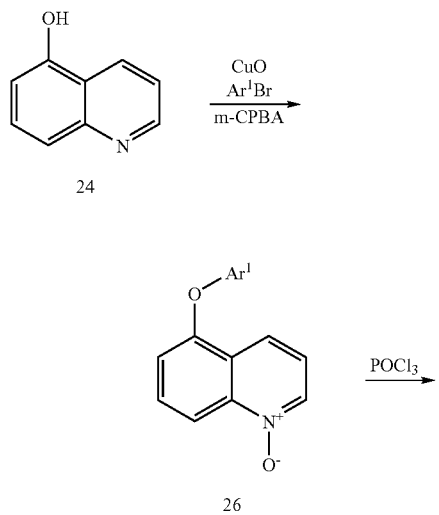

5-Hydroxy quinoline (24) is benzylated with benzyl bromide and subsequently oxidized with m-CPBA to the N-oxide of formula (25). Upon treatment with phosphorous oxychloride (neat) the 2 chloro derivative (23) is generated which was transferred to the 2-amino product of formula I-11.

Route 17 describes compounds according to scheme 17 as described in example 75 for X being —O— and the other definitions are as described above.

5-Hydroxy quinoline (24) is alkylated with Ar¹Br/CuO and subsequently oxidized with m-CPBA to N-oxide (266). Upon treatment with phosphorous oxychloride (neat) the 2 chloro derivative (27) is generated which is transferred to the 2-amino product of formula I-12.

Route 18 describes compounds according to scheme 18 as described in example 3 for X being a bond and the other definitions are as described above.

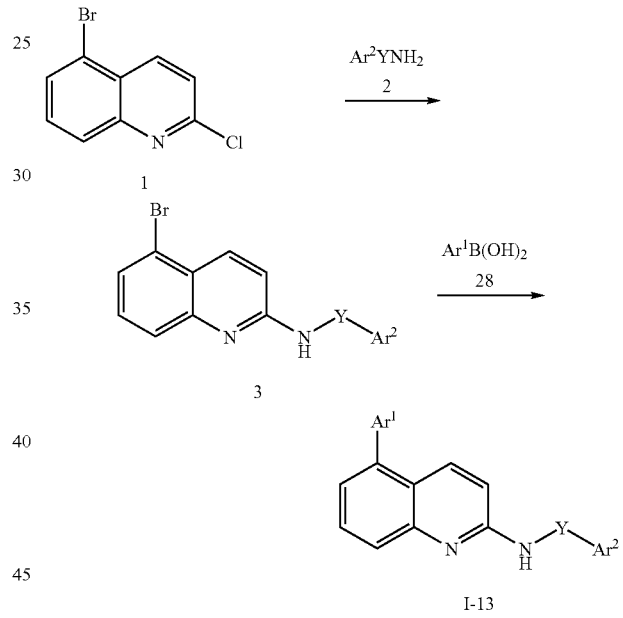

5-Bromo-2-chloroquinoline (1) is reacted with 2 equivalents of an amine Ar²YNH₂ (2) without a solvent. Intermediate 3 is reacted with a boronic acid of formula Ar¹B(OH)₂ (28) in a palladium catalyzed substitution reaction to a compound of formula I-13.

Route 19 according to scheme 17 is described in examples 46, 53 and 56 for Z being a bond or CH₂ and the remaining definitions are as described above;

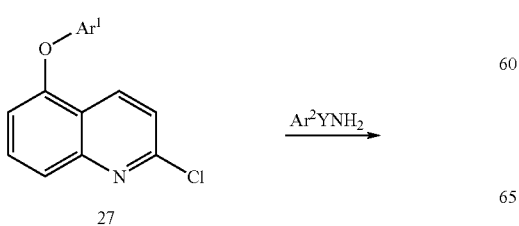

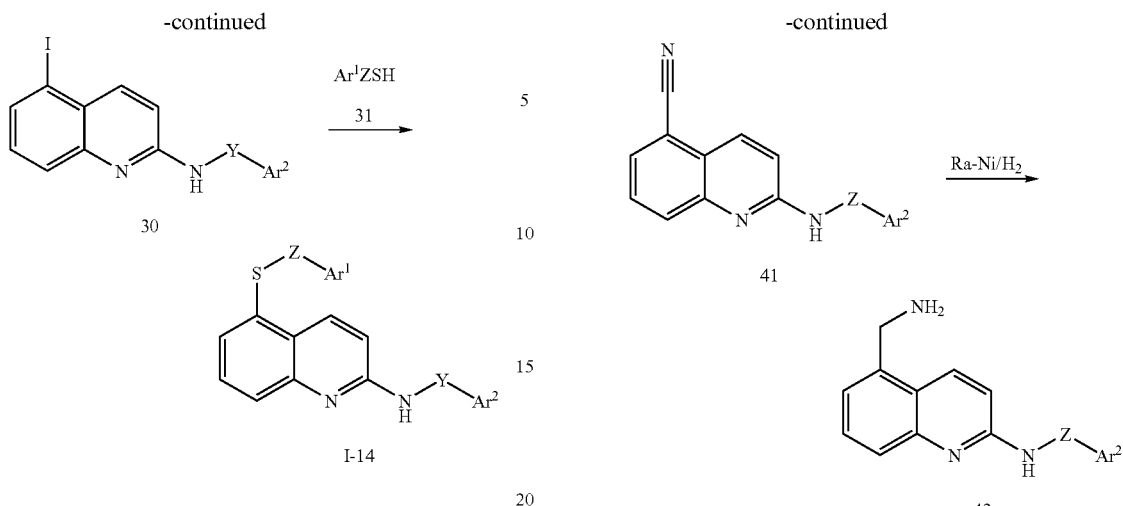

5-Iodo-2-chloroquinoline (29) is reacted with 2 equivalents of an amine of formula $Ar^2YNH_2$ (2) without a solvent. Intermediate 30 is reacted with a sulfide $Ar^1ZSH$ (31) in a palladium catalyzed substitution reaction to a compound of formula I-14.

Route 20 according to scheme 20 is described in example 82 for Z being —$CH_2$— and the remaining definitions are as described above;

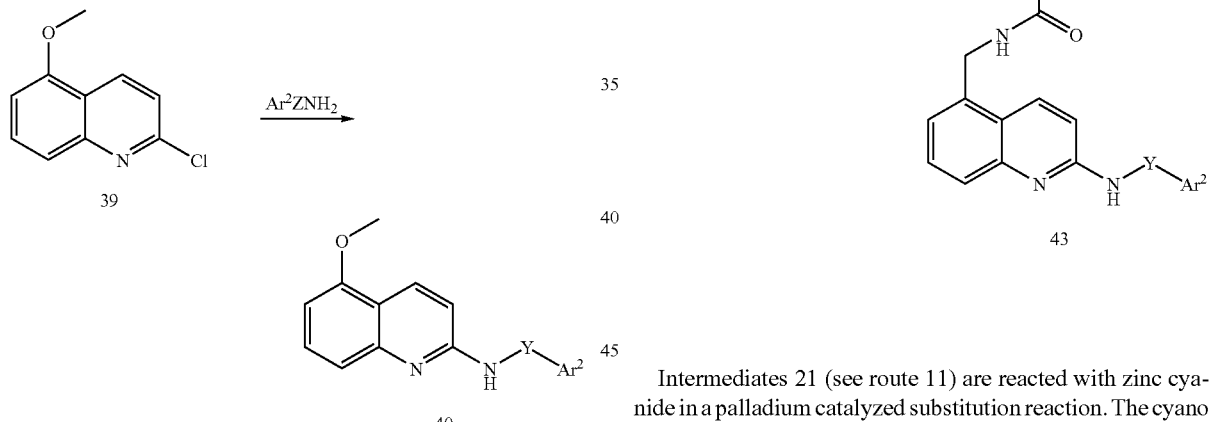

2-Chloro-6-methoxy quinolin 39 was reacted with an amine ($NH_2ZAr^2$) to give a compound 40.

Route 21 according to scheme 21 is described in example 126 for Z being —$CH_2$— and the remaining definitions are as described above;

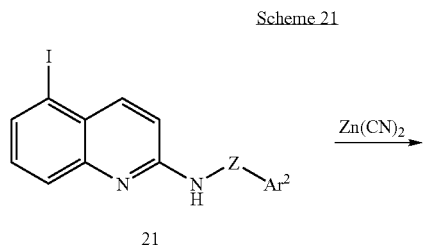

Intermediates 21 (see route 11) are reacted with zinc cyanide in a palladium catalyzed substitution reaction. The cyano group in 41 is reduced with hydrogen to the amine 42. Amines 42 are reacted with a benzoyl chlorides ($Ar^1COCl$) to give a compound 43.

Route 22 according to scheme 22 is described in example 127 for Z being —$CH_2$— and the remaining definitions are as described above;

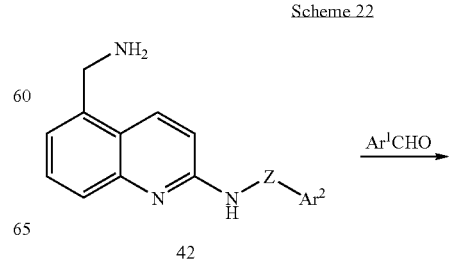

-continued

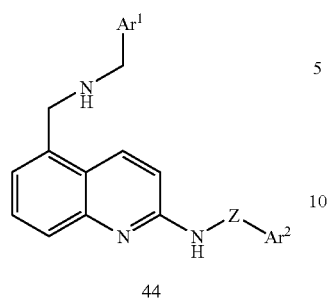

44

Reductive amination of benzaldehydes (Ar¹CHO) with amines 42 to give a compound of 44.

Route 23 according to scheme 23 is described in example 136 for Z being —CH$_2$— and the remaining definitions are as described above;

Scheme 23

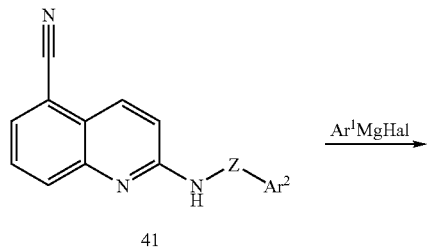

Reaction of cyano derivatives 41 with aryl Grignard reagents (Ar¹MgHal) to give a compound 45.

Route 24 according to scheme 24 is described in example 137 for Z being —CH$_2$— and the remaining definitions are as described above;

Scheme 24

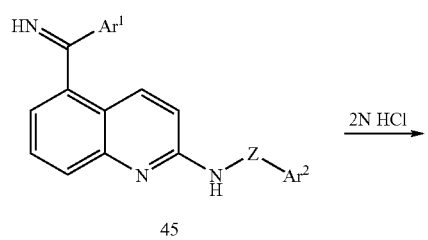

-continued

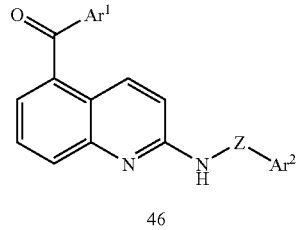

46

Transformation of imines 45 to ketones 46 to give a compound 46.

Route 25 according to scheme 25 is described in example 150 for Z being —CH$_2$— and the remaining definitions are as described above;

Scheme 25

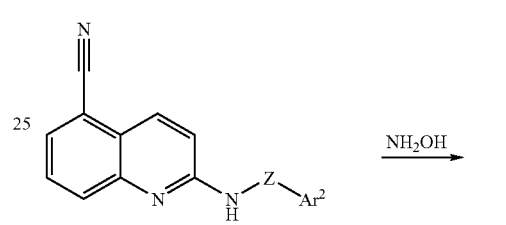

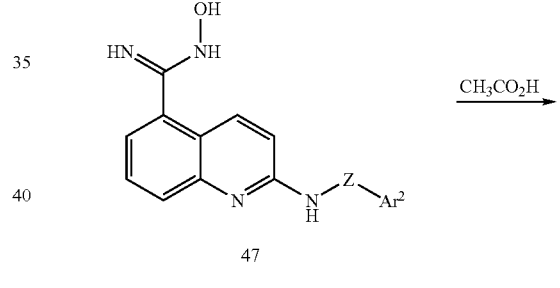

Reaction of cyano derivatives 41 with hydroxylamine to the corresponding amidoximes 47. Formation of the methyloxadiazole derivatives 48 with acetic acid to give a compound 48.

Route 26 according to scheme 26 is described in example 89 for Z being a bond and the remaining definitions are as described above;

Scheme 26

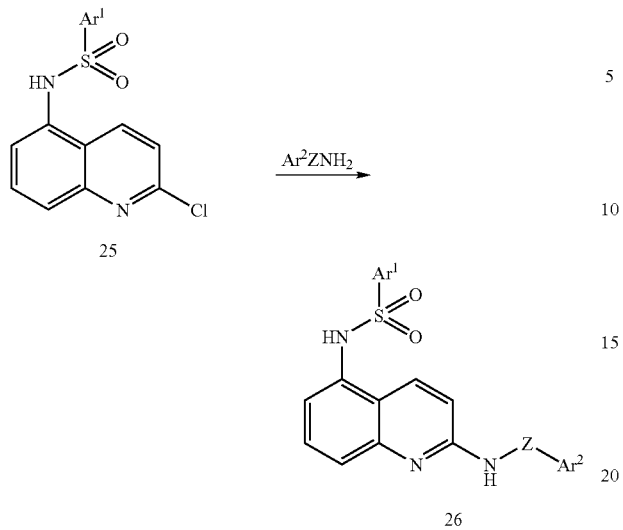

Intermediate 25 is reacted with an amine (Ar²XNH₂) in a palladium catalyzed substitution reaction to give a compound 26.

Route 27 according to scheme 27 is described in examples 83 and 84 for Z being —CH₂— and the remaining definitions are as described above;

Scheme 27

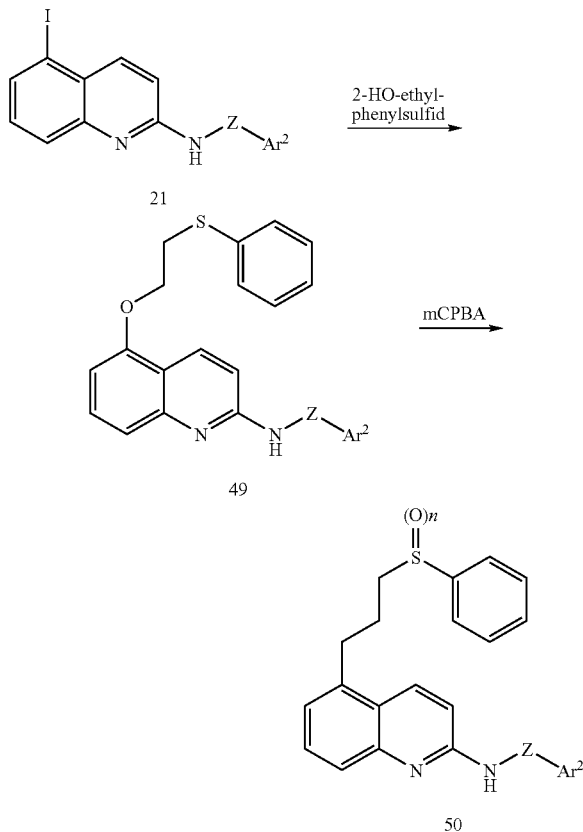

Intermediate 21 is reacted with 2-hydroxy-phenylsulfide in a CuI catalyzed substitution reaction and subsequently the sulfide group oxidized by mCPBA to the respective sulfoxide 50 (n=1) and sulfon 50 (n=2) concomitantly to give a compound 50.

Route 28 according to scheme 28 is described in example 167 with the definitions are as described above;

Scheme 28

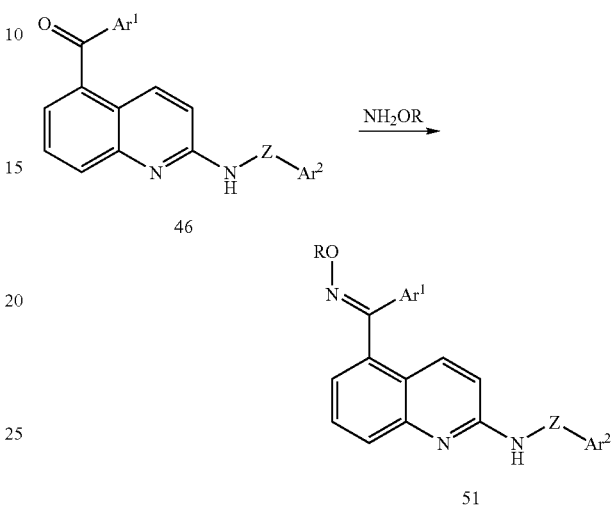

Ketone 46 is reacted with an hydroxylamine to give the corresponding oxime 51.

The following abbreviations have been used:

m-CPBA=meta-chloroperbenzoic acid

DMF=N,N-dimethylformamide.

As mentioned earlier, the compounds of formula I and their pharmaceutically usable addition salts possess valuable pharmaceutical properties. It has been found that the compounds of the present invention are active on the 5-HT$_{5A}$ receptor and therefore suitable for the treatment of depression, anxiety disorders, schizophrenia, panic disorders, agoraphobia, social phobia, obsessive compulsive disorders, post-traumatic stress disorders, pain, memory disorders, dementia, disorders of eating behaviors, sexual dysfunction, sleep disorders, withdrawal from abuse of drugs, motor disorders such as Parkinson's disease, psychiatric disorders or gastrointestinal disorders.

Test Description

A [³H]LSD radioligand binding assay was used to determine the affinity of the compounds for the recombinant human 5-HT$_{5A}$ receptor, in membranes from transiently (cDNA) expressed 5-HT$_{5A}$ receptors in Human Embryonic Kidney-EBNA (HEK-EBNA) cells. Assay buffer consisted of Tris (50 mM) buffer containing 1 mM EGTA, 10 mM MgCl₂ (pH 7.4) and 10 µM pargyline. The binding assay was carried out in 96-well-plates in the presence of [³H]LSD (approximately 1 nM), approximately 2 µg/well of membrane protein, and 0.5 mg of Ysi-poly-l-lysine SPA beads in a final volume of 200 µl of buffer. Non-specific binding was defined using methiothepin 2 µM. Compounds were tested at 10 concentrations. All assays were conducted in duplicate and repeated at least two times. Assay plates were incubated for 120 min at room temperature before centrifugation. Bound ligand was determined using a Packard Topcount scintillation counter. $IC_{50}$ values were calculated using a non-linear curve fitting program and Ki values calculated using the Cheng-Prussoff equation.

The activity of representative compounds (≦0.05 μM) is described in the tables below:

| Example | Ki (μM) |
|---|---|
| 1 | 0.00865 |
| 4 | 0.00951 |
| 5 | 0.0097 |
| 6 | 0.01016 |
| 7 | 0.00757 |
| 9 | 0.03445 |
| 13 | 0.01533 |
| 15 | 0.01109 |
| 16 | 0.03263 |
| 17 | 0.02131 |
| 20 | 0.0254 |
| 21 | 0.03583 |
| 22 | 0.02345 |
| 23 | 0.01841 |
| 26 | 0.02102 |
| 27 | 0.04296 |
| 28 | 0.04937 |
| 29 | 0.01754 |
| 33 | 0.03929 |
| 34 | 0.01236 |
| 35 | 0.01702 |
| 37 | 0.04955 |
| 39 | 0.02866 |
| 42 | 0.01249 |
| 45 | 0.01321 |
| 46 | 0.03409 |
| 51 | 0.00909 |
| 54 | 0.0447 |
| 57 | 0.03143 |
| 58 | 0.00761 |
| 59 | 0.01985 |
| 60 | 0.02173 |
| 61 | 0.01917 |
| 73 | 0.02141 |
| 74 | 0.01288 |
| 77 | 0.01909 |
| 82 | 0.03385 |
| 83 | 0.09558 |
| 84 | 0.08827 |
| 85 | 0.01674 |
| 87 | 0.01571 |
| 88 | 0.0329 |
| 89 | 0.05055 |
| 90 | 0.05287 |
| 91 | 0.00525 |
| 92 | 0.01437 |
| 93 | 0.02817 |
| 94 | 0.01068 |
| 96 | 0.01942 |
| 97 | 0.03103 |
| 98 | 0.03327 |
| 99 | 0.08461 |
| 100 | 0.02272 |
| 101 | 0.01451 |
| 102 | 0.00641 |
| 103 | 0.00657 |
| 105 | 0.02415 |
| 106 | 0.03039 |
| 107 | 0.00392 |
| 108 | 0.04962 |
| 109 | 0.09728 |
| 110 | 0.01678 |
| 111 | 0.01013 |
| 113 | 0.0206 |
| 114 | 0.00333 |
| 115 | 0.03527 |
| 116 | 0.03289 |
| 117 | 0.03244 |
| 118 | 0.00566 |
| 119 | 0.00845 |

-continued

| Example | Ki (μM) |
|---|---|
| 120 | 0.00845 |
| 124 | 0.00629 |
| 125 | 0.00233 |
| 128 | 0.07969 |
| 129 | 0.01596 |
| 130 | 0.0474 |
| 131 | 0.01738 |
| 132 | 0.01498 |
| 134 | 0.02165 |
| 135 | 0.01715 |
| 136 | 0.03563 |
| 137 | 0.05086 |
| 139 | 0.03555 |
| 140 | 0.01193 |
| 141 | 0.02197 |
| 142 | 0.03706 |
| 143 | 0.01824 |
| 144 | 0.01537 |
| 145 | 0.05132 |
| 146 | 0.08603 |
| 147 | 0.00431 |
| 148 | 0.00308 |
| 149 | 0.00397 |
| 151 | 0.00474 |
| 152 | 0.01469 |
| 154 | 0.0255 |
| 156 | 0.0451 |
| 158 | 0.0031 |
| 159 | 0.0283 |
| 160 | 0.01582 |
| 161 | 0.03553 |
| 162 | 0.00715 |
| 163 | 0.00992 |
| 164 | 0.01659 |
| 165 | 0.00643 |
| 166 | 0.03423 |
| 167 | 0.00719 |

The present invention also provides pharmaceutical compositions containing compounds of the invention, for example compound of formula I or their pharmaceutically usable acid addition salts, and a pharmaceutically acceptable carrier. Such pharmaceutical compositions can be in the form of tablets, coated tablets, dragées, hard and soft gelatine capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic and organic carriers. Lactose, corn starch or derivatives thereof, talc, stearic acid or its salts etc can be used as such excipients e.g. for tablets, dragées and hard gelatine capsules. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are however usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The invention also provides a method for preparing compositions of the invention which comprises bringing one or more compounds of formula I and/or pharmaceutically acceptable acid addition salts and, if desired, one or more other therapeutically valuable substances into a galenical administration form together with one or more therapeutically inert carriers.

The most preferred indications in accordance with the present invention are those, which include disorders of the central nervous system, for example the treatment of anxiety, depression, sleep disorders and schizophrenia. Thus, the present invention provides a method for treating anxiety, which comprises administering to an individual a therapeutically effective amount of a compound of the invention. The invention also provides a method for the treatment of depression, which comprises administering to an individual a therapeutically effective amount of a compound of the invention. The invention further provides a method for treating schizophrenia, which comprises administering to an individual a therapeutically effective amount of a compound of the invention. The invention provides a method for treating sleep disorders, which comprises administering to an individual a therapeutically effective amount of a compound of the invention.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

| | | Tablet Formulation (Wet Granulation) mg/tablet | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

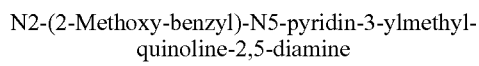

| | | Capsule Formulation mg/capsule | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |

-continued

| | | Capsule Formulation mg/capsule | | | |
|---|---|---|---|---|---|
| Item | Ingredients | 5 mg | 25 mg | 100 mg | 500 mg |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

Compounds of formula I may be prepared as shown in the following description:

Example 1

N2-(2-Methoxy-benzyl)-N5-pyridin-3-ylmethyl-quinoline-2,5-diamine

Step A

5-Bromo-2-chloroquinoline (CAS 99455-13-7, 2.4 g, 10 mmol) and 2-methoxybenzylamine (2.7 g, 20 mmol) were stirred in a sealed tube at 120° C. for 3 days. The reaction mixture was purified by flash chromatography on silica gel (cyclohexane/ethyl acetate 100:0->80:20 gradient). (5-Bromo-quinolin-2-yl)-(2-methoxy-benzyl)-amine was obtained as a light yellow solid (2.3 g, 67%), MS: m/e=343.1, 345.0 (M+H$^+$).

Step B (5-Bromo-quinolin-2-yl)-(2-methoxy-benzyl)-amine (200 mg, 0.583 mmol) was dissolved in 3 mL dioxane. Argon was bubbled through the solution for 2 minutes to remove oxygen. 3-Picolylamine (127 mg, 1.18 mmol), sodium tert.-butylate (144 mg, 1.50 mmol), 1,1'-bis(diphenylphosphin)ferrocen (50 mg, 0.09 mmol) and 1,1'-bis(diphenylphosphin)ferrocen-palladium(II)chloride (24 mg, 0.03 mmol) were added. The reaction mixture was stirred in a sealed tube at 100° C. for 2.5 h. The solvent was evaporated and the residue purified by flash chromatography on silica gel (dichloromethane/methanol 100:0->90:10 gradient). The title compound was obtained as a light brown solid (183 mg, 85%), MS: m/e=371.1 (M+H$^+$).

Example 2

(2-Methoxy-benzyl)-[5-((E)-styryl)-quinolin-2-yl]-amine

Step A (5-Bromo-quinolin-2-yl)-(2-methoxy-benzyl)-amine was prepared as described in example 1 step A.

Step B (5-Bromo-quinolin-2-yl)-(2-methoxy-benzyl)-amine (200 mg, 0.583 mmol) was dissolved in 3 mL dimethylformamide. Styrene (79 mg, 0.760 mmol), triethylamine (77 mg, 0.760 mmol), tri-o-tolylphosphine (14 mg, 0.046 mmol) and palladium(II)acetate (5 mg, 0.022 mmol) were added. The reaction mixture was stirred in a sealed tube at 100° C. for 2 h. The reaction mixture was poured into 30 mL water and extracted

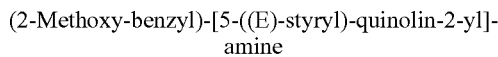

three times with ethyl acetate (30 mL each). The combined organic extracts were dried with sodium sulfate, filtered and evaporated. The residue purified by flash chromatography on silica gel (cyclohexane/ethyl acetate 100:0->80:20 gradient). The title compound was obtained as a light yellow solid (142 mg, 67%), MS: m/e=367.1 (M+H$^+$).

Example 3

(2-Methoxy-benzyl)-(5-phenyl-quinolin-2-yl)-amine

Step A (5-Bromo-quinolin-2-yl)-(2-methoxy-benzyl)-amine was prepared as described in example 1 step A.

Step B (5-Bromo-quinolin-2-yl)-(2-methoxy-benzyl)-amine (200 mg, 0.583 mmol) was dissolved in 8 mL 1,2-dimethoxy-ethane and 4 mL 1M sodium carbonate solution. The reaction mixture was evacuated and backfilled with argon for three times to remove oxygen. Phenylboronic acid (88 mg, 0.699 mmol), palladium(II)acetate (7 mg, 0.029 mmol) and triphenylphosphine (16 mg, 0.058 mmol) were added. The reaction mixture was refluxed overnight. The reaction mixture was poured into 100 mL water and extracted three times with ethyl acetate (100 mL each). The combined organic extracts were dried with sodium sulfate, filtered and evaporated. The residue purified by flash chromatography on silica gel (cyclohexane/ethyl acetate 100:0->80:20 gradient). The title compound was obtained as a white solid (191 mg, 96%), MS: m/e=341.3 (M+H$^+$).

Example 4

(2-Methoxy-benzyl)-(5-phenethyl-quinolin-2-yl)-amine (2-Methoxy-benzyl)-[5-((E)-styryl)-quinolin-2-yl]-amine (example 2, 102 mg, 0.279 mmol) was dissolved in 20 mL ethanol. Palladium on charcoal (10%, 30 mg, 0.028 mmol) was added and the reaction mixture war hydrogenated with a hydrogen balloon overnight. The palladium was filtered off and the solvent was evaporated. The title compound was obtained as a light brown oil (97 mg, 95%), MS: m/e=369.0 (M+H$^+$).

Example 5

N5-(3-Methoxy-benzyl)-N2-(2-methoxy-benzyl)-quinoline-2,5-diamine

The title compound, MS: m/e=400.3 (M+H$^+$), was prepared in accordance with the general method of example 1 from 5-bromo-2-chloroquinoline, 2-methoxybenzylamine and 3-methoxybenzylamine.

Example 6

N2,N5-Bis-(2-methoxy-benzyl)-quinoline-2,5-diamine

The title compound, MS: m/e=400.3 (M+H$^+$), was prepared in accordance with the general method of example 1 from 5-bromo-2-chloroquinoline and 2-methoxybenzylamine in step A and step B.

Example 7

N5-Benzyl-N2-(2-methoxy-benzyl)-quinoline-2,5-diamine

The title compound, MS: m/e=370.0 (M+H$^+$), was prepared in accordance with the general method of example 1 from 5-bromo-2-chloroquinoline, 2-methoxybenzylamine and benzylamine.

Example 8

N2-(2-Methoxy-benzyl)-N5-methyl-N5-pyridin-3-ylmethyl-quinoline-2,5-diamine

The title compound, MS: m/e=385.0 (M+H$^+$), was prepared in accordance with the general method of example 1 from 5-bromo-2-chloroquinoline, 2-methoxybenzylamine and N-methyl-3-picolylamine.

Example 9

N2-(2-Methoxy-benzyl)-N5-pyridin-4-ylmethyl-quinoline-2,5-diamine

The title compound, MS: m/e=371.4 (M+H$^+$), was prepared in accordance with the general method of example 1 from 5-bromo-2-chloroquinoline, 2-methoxybenzylamine and 4-picolylamine.

Example 10

N2-(2-Methoxy-benzyl)-N5-(3-methyl-3H-imidazol-4-ylmethyl)-quinoline-2,5-diamine The title compound, MS: m/e=374.4 (M+H$^+$), was prepared in accordance with the general method of example 1 from 5-bromo-2-chloroquinoline, 2-methoxybenzylamine and (1-methyl-1H-imidazol-5-yl)methylamine.

Example 11

(2-Methoxy-benzyl)-[5-((E)-2-pyridin-3-yl-vinyl)-quinolin-2-yl]-amine

Step A (5-Bromo-quinolin-2-yl)-(2-methoxy-benzyl)-amine was prepared as described in example 1 step A.

Step B (5-Bromo-quinolin-2-yl)-(2-methoxy-benzyl)-amine (1000 mg, 2.92 mmol) was dissolved in 30 mL toluene. The reaction mixture was evacuated and backfilled with argon for three times to remove oxygen. Vinyltributyltin (952 mg, 3.00 mmol) and tetrakis(triphenylphosphine)palladium(0) (67 mg, 0.058 mmol) were added. The reaction mixture was refluxed overnight and evaporated. The residue was poured into 50 mL acetonitrile and extracted three times with heptane (50 mL each) to remove the tin products. The acetonitrile phase was dried with sodium sulfate, filtered and evaporated. The residue was purified by flash chromatography on silica gel (cyclohexane/ethyl acetate 100:0->80:20 gradient). (2-Methoxy-benzyl)-(5-vinyl-quinolin-2-yl)-amine was obtained as a light yellow gum (544 mg, 64%), MS: m/e=291.3 (M+H$^+$).

Step C (2-Methoxy-benzyl)-(5-vinyl-quinolin-2-yl)-amine (150 mg, 0.517 mmol) was reacted with 3-bromopyridine (108 mg, 0.688 mmol) as described in example 2 step B. The title compound was obtained as a light brown solid (93 mg, 49%), MS: m/e=368.1 (M+H$^+$).

Example 12

(2-Methoxy-benzyl)-[5-((E)-2-pyrimidin-5-yl-vinyl)-quinolin-2-yl]-amine

The title compound, MS: m/e=369.1 (M+H$^+$), was prepared in accordance with the general method of example 11 from 5-bromo-2-chloroquinoline, 2-methoxybenzylamine and 5-bromopyrimidine.

Example 13

N5-(2-Methoxy-benzyl)-N2-(5-methyl-furan-2-ylmethyl)-quinoline-2,5-diamine

The title compound, MS: m/e=374.3 (M+H$^+$), was prepared in accordance with the general method of example 1 from 5-bromo-2-chloroquinoline, 5-methyl-2-furanmethanamine and 2-methoxybenzylamine.

Example 14

(5-Methyl-furan-2-ylmethyl)-[5-((E)-styryl)-quinolin-2-yl]-amine

The title compound, MS: m/e=341.3 (M+H$^+$), was prepared in accordance with the general method of example 2 from 5-bromo-2-chloroquinoline, 5-methyl-2-furanmethanamine and styrene.

Example 15

N2-(5-Methyl-furan-2-ylmethyl)-N5-pyridin-3-ylmethyl-quinoline-2,5-diamine

The title compound, MS: m/e=345.0 (M+H$^+$), was prepared in accordance with the general method of example 1 from 5-bromo-2-chloroquinoline, 5-methyl-2-furanmethanamine and 3-picolylamine.

Example 16

(2-Methoxy-benzyl)-[5-(2-pyridin-3-yl-ethyl)-quinolin-2-yl]-amine

The title compound, MS: m/e=370.0 (M+H$^+$), was prepared in accordance with the general method of example 4 from (2-methoxy-benzyl)-[5-((E)-2-pyridin-3-yl-vinyl)-quinolin-2-yl]-amine (example 11).

Example 17

(5-Methyl-furan-2-ylmethyl)-(5-phenethyl-quinolin-2-yl)-amine

The title compound, MS: m/e=343.3 (M+H$^+$), was prepared in accordance with the general method of example 4 from (5-methyl-furan-2-ylmethyl)-[5-((E)-styryl)-quinolin-2-yl]-amine (example 14).

Example 18

(2-Methoxy-benzyl)-[5-(2-pyrimidin-5-yl-ethyl)-quinolin-2-yl]-amine

The title compound, MS: m/e=371.1 (M+H$^+$), was prepared in accordance with the general method of example 4 from (2-methoxy-benzyl)-[5-((E)-2-pyrimidin-5-yl-vinyl)-quinolin-2-yl]-amine (example 12).

Example 19

(3-{(E)-2-[2-(2-Methoxy-benzylamino)-quinolin-5-yl]-vinyl}-phenyl)-methanol

The title compound, MS: m/e=397.3 (M+H$^+$), was prepared in accordance with the general method of example 11 from 5-bromo-2-chloroquinoline, 2-methoxybenzylamine and 3-bromobenzylalcohol.

Example 20

N5-(4-Fluoro-benzyl)-N2-(5-methyl-furan-2-ylmethyl)-quinoline-2,5-diamine

The title compound, MS: m/e=362.4 (M+H$^+$), was prepared in accordance with the general method of example 1 from 5-bromo-2-chloroquinoline, 5-methyl-2-furanmethanamine and 4-fluorobenzylamine.

Example 21

(5-Methyl-furan-2-ylmethyl)-[5-(pyridin-3-ylaminomethyl)-quinolin-2-yl]-amine

Step A (5-Bromo-quinolin-2-yl)-(5-methyl-furan-2-ylmethyl)-amine was prepared from 5-bromo-2-chloroquinoline and 5-methyl-2-furanmethanamine as described in example 1 step A.

Step B (5-Bromo-quinolin-2-yl)-(5-methyl-furan-2-ylmethyl)-amine (700 mg, 2.11 mmol) was dissolved in 30 mL tetrahydrofurane. n-Butyllithium solution (1.6 M in hexane, 3.45 mL, 2.16 mmol) was slowly added at −78° C. The reaction mixture was allowed to warm to −10° C. and stirred at this temperature for 45 min. The reaction mixture was then cooled again to −78° C. and dimethylformamide (404 mg, 5.53 mmol) was added. The mixture was then slowly warmed up and quenched with 100 mL water at 5° C. The mixture was extracted three times with ethyl acetate (100 mL each). The organic phases ware pooled, dried with sodium sulfate, filtered and evaporated. The residue was purified by flash chromatography on silica gel (cyclohexane/ethyl acetate 100:0->50:50 gradient). 2-[(5-Methyl-furan-2-ylmethyl)-amino]-quinoline-5-carbaldehyde was obtained as a brown oil (242 mg, 41%), MS: m/e=185.1 (M-methylfuran$^+$).

Step C

2-[(5-Methyl-furan-2-ylmethyl)-amino]-quinoline-5-carbaldehyde (100 mg, 0.376 mmol) was dissolved in 5 mL ethylendichloride. 3-Aminopyridine (50 mg, 0.532 mmol) and acetic acid (90 mg, 1.50 mmol) were added. The reaction mixture was stirred at room temperature for 1 h. Sodium triacetoxy borohydride (172 mg, 0.811 mmol) was added and stirring was continued overnight. The reaction mixture was quenched by addition of 50 mL water. The mixture was extracted three times with dichloromethane (50 mL each). The organic phases ware pooled, dried with sodium sulfate, filtered and evaporated. The crude product was recrystallized from dichloromethane. The title compound was obtained as a white solid (50 mg, 39%), MS: m/e=345.0 (M+H$^+$).

Example 22

(5-Methyl-furan-2-ylmethyl)-(5-phenylaminomethyl-quinolin-2-yl)-amine

The title compound, MS: m/e=344.1 (M+H$^+$), was prepared in accordance with the general method of example 21 from 5-bromo-2-chloroquinoline, 5-methyl-2-furanmethanamine and aniline.

Example 23

(3-{2-[2-(2-Methoxy-benzylamino)-quinolin-5-yl]-ethyl}-phenyl)-methanol

The title compound, MS: m/e=399.3 (M+H$^+$), was prepared in accordance with the general method of example 4 from (3-{(E)-2-[2-(2-methoxy-benzylamino)-quinolin-5-yl]-vinyl}-phenyl)-methanol (example 19).

Example 24

N5-(3-Methoxymethyl-benzyl)-N2-(5-methyl-furan-2-ylmethyl)-quinoline-2,5-diamine The title compound, MS: m/e=388.4 (M+H$^+$), was prepared in accordance with the general method of example 1 from 5-bromo-2-chloroquinoline, 5-methyl-2-furanmethanamine and 3-methoxymethyl-benzylamine (CAS 148278-90-4).

Example 25

N5-[3-(2-Methoxy-ethoxymethyl)-benzyl]-N2-(5-methyl-furan-2-ylmethyl)-quinoline-2,5-diamine The title compound, MS: m/e=432.3 (M+H$^+$), was prepared in accordance with the general method of example 1 from 5-bromo-2-chloroquinoline, 5-methyl-2-furanmethanamine and 3-(2-methoxy-ethoxymethyl)-benzylamine.

Synthesis of 3-(2-methoxy-ethoxymethyl)-benzylamine

Step 1

Sodium hydride (55% in mineral oil, 1.76 g, 40.5 mmol) was suspended in 100 mL tetrahydrofurane. 3-(Hydroxymethyl)benzonitrile (5.0 g, 36.5 mmol), dissolved in 200 mL tetrahydrofuran was added dropwise. The reaction mixture was stirred at room temperature for 1 h. 2-Bromoethylmethylether (7.0 mL, 76 mmol) was added and the reaction mixture was refluxed overnight. The reaction mixture was quenched with 3 mL 2N sodium carbonate solution and the solvent was evaporated. The residue was taken up in 100 mL water and extracted three times with ethyl acetate (100 mL each). The organic phases ware pooled, dried with sodium sulfate, filtered and evaporated. The residue was purified by flash chromatography on silica gel (cyclohexane/ethyl acetate 100:0->50:50 gradient). 3-(2-Methoxy-ethoxymethyl)-benzonitrile was obtained as a yellow liquid (2.63 g, 38%).

3-(2-Methoxy-ethoxymethyl)-benzonitrile (2.58 g, 13.5 mmol) was dissolved in 50 mL tetrahydrofuran. Lithiumaluminium hydride (660 mg, 17.5 mmol) was added portionwise at 0° C. The reaction mixture was stirred at room temperature overnight and quenched by sequential addition of 0.66 mL water, 0.66 mL 15% sodium hydroxide solution and 1.98 mL water. The solid was filtered off and the filtrate was evaporated. The title compound was obtained as a yellow liquid (2.63 g, 97%), MS: m/e=196.3 (M+H$^+$).

Example 26

N2-(5-Methyl-furan-2-ylmethyl)-N5-pyridin-2-ylmethyl-quinoline-2,5-diamine

Step A (5-Methyl-furan-2-ylmethyl)-(5-nitro-quinolin-2-yl)-amine, MS: m/e=284.3 (M+H$^+$), was prepared from 5-nitro-2-chloroquinoline (CAS 13067-94-2) and 5-methyl-2-furanmethanamine as described in example 1 step A.

Step B

N$^2$-(5-Methyl-furan-2-ylmethyl)-quinoline-2,5-diamine, MS: m/e=254.4 ((M+H$^+$), was prepared from (5-methyl-furan-2-ylmethyl)-(5-nitro-quinolin-2-yl)-amine as described in example 4.

Step C

The title compound, MS: m/e=345.3 (M+H$^+$), was prepared from N$^2$-(5-methyl-furan-2-ylmethyl)-quinoline-2,5-diamine and 2-pyridinecarboxaldehyde as described in example 21 step C.

Example 27

N5-(2-Methoxy-pyridin-3-ylmethyl)-N2-(5-methyl-furan-2-ylmethyl)-quinoline-2,5-diamine The title compound, MS: m/e=375.1 (M+H$^+$), was prepared from 5-nitro-2-chloroquinoline, 5-methyl-2-furanmethanamine and 2-methoxy-3-pyridinecarboxaldehyde as described in example 26.

Example 28

N5-[3-(2-Methoxy-ethoxy)-benzyl]-N2-(5-methyl-furan-2-ylmethyl)-quinoline-2,5-diamine The title compound, MS: m/e=418.4 (M+H$^+$), was prepared in accordance with the general method of example 1 from 5-bromo-2-chloroquinoline, 5-methyl-2-furanmethanamine and 3-(2-methoxy-ethoxy)-benzylamine.

3-(2-Methoxy-ethoxy)-benzylamine, MS: m/e=182.1 (M+H$^+$), was prepared in accordance with the general method of example 25 step 2 from 3-(2-methoxy-ethoxy)-benzonitrile (CAS 80407-67-6).

Example 29

N2-(5-Methyl-furan-2-ylmethyl)-N5-(6-methyl-pyridin-2-ylmethyl)-quinoline-2,5-diamine The title compound, MS: m/e=359.1 (M+H$^+$), was prepared from 5-nitro-2-chloroquinoline, 5-methyl-2-furanmethanamine and 6-methyl-2-pyridinecarboxaldehyde as described in example 26.

Example 30

N2-(5-Methyl-furan-2-ylmethyl)-N5-phenyl-quinoline-2,5-diamine

The title compound, MS: m/e=330.4 (M+H$^+$), was prepared from 5-nitro-2-chloroquinoline, 5-methyl-2-furanmethanamine and aniline as described in example 26.

Example 31

3-((E)-2-{2-[(5-Methyl-furan-2-ylmethyl)-amino]-quinolin-5-yl}-vinyl)-benzenesulfonamide The title compound, MS: m/e=420.0 (M+H$^+$), was prepared in accordance with the general method of example 11 from 5-bromo-2-chloroquinoline, 5-methyl-2-furanmethanamine and 3-bromobenzene-1-sulfonamide.

Example 32

{5-[(E)-2-(3-Methoxymethyl-phenyl)-vinyl]-quinolin-2-yl}-(5-methyl-furan-2-ylmethyl)-amine The title compound, MS: m/e=385.3 (M+H$^+$), was prepared in accordance with the general method of example 11 from 5-bromo-2-chloroquinoline, 5-methyl-2-furanmethanamine and 3-bromobenzyl methyl ether (CAS1515-89-5).

Example 33

{5-[2-(3-Methoxymethyl-phenyl)-ethyl]-quinolin-2-yl}-(5-methyl-furan-2-ylmethyl)-amine The title compound, MS: m/e=387.3 (M+H$^+$), was prepared in accordance with the general method of example 4 from {5-[(E)-2-(3-methoxymethyl-phenyl)-vinyl]-quinolin-2-yl}-(5-methyl-furan-2-ylmethyl)-amine (example 32):

Example 34

3-(2-{2-[(5-Methyl-furan-2-ylmethyl)-amino]-quinolin-5-yl}-ethyl)-benzenesulfonamide The title compound, MS: m/e=422.1 (M+H$^+$), was prepared in accordance with the general method of example 4 from 3-((E)-2-{2-[(5-methyl-furan-2-ylmethyl)-amino]-quinolin-5-yl}-vinyl)-benzenesulfonamide (example 31):

Example 35

3-({2-[(5-Methyl-furan-2-ylmethyl)-amino]-quinolin-5-ylamino}-methyl)-benzenesulfonamide The title compound, MS: m/e=423.1 (M+H$^+$), was prepared from 5-nitro-2-chloroquinoline, 5-methyl-2-furanmethanamine and 3-formylbenzenesulfonamide (CAS 1778-37-6) as described in example 26.

Example 36

(5-Methyl-furan-2-ylmethyl)-[5-(pyrimidin-2-ylaminomethyl)-quinolin-2-yl]-amine

The title compound, MS: m/e=346.3 (M+H$^+$), was prepared in accordance with the general method of example 21 from 5-bromo-2-chloroquinoline, 5-methyl-2-furanmethanamine and 2-aminopyrimidine.

Example 37

(5-Methyl-furan-2-ylmethyl)-[5-(pyridin-2-ylaminomethyl)-quinolin-2-yl]-amine

The title compound, MS: m/e=345.3 (M+H$^+$), was prepared in accordance with the general method of example 21 from 5-bromo-2-chloroquinoline, 5-methyl-2-furanmethanamine and 2-aminopyridine.

Example 38

N2-(5-Methyl-furan-2-ylmethyl)-N5-pyridin-3-yl-quinoline-2,5-diamine

Step A
(5-Methyl-furan-2-ylmethyl)-(5-nitro-quinolin-2-yl)-amine, MS: m/e=284.3 (M+H$^+$), was prepared from 5-nitro-2-chloroquinoline (CAS 13067-94-2) and 5-methyl-2-furanmethanamine as described in example 1 step A.

Step B
N$^2$-(5-Methyl-furan-2-ylmethyl)-quinoline-2,5-diamine, MS: m/e=254.4 (M+H$^+$), was prepared from (5-methyl-furan-2-ylmethyl)-(5-nitro-quinolin-2-yl)-amine as described in example 4.

Step C
The title compound, MS: m/e=331.3 (M+H$^+$), was prepared from N$^2$-(5-methyl-furan-2-ylmethyl)-quinoline-2,5-diamine and 3-bromopyridine as described in example 1 step B.

Example 39

N-{2-[(5-Methyl-furan-2-ylmethyl)-amino]-quinolin-5-yl}-benzenesulfonamide

N$^2$-(5-Methyl-furan-2-ylmethyl)-quinoline-2,5-diamine (example 26, step A+B, 200 mg, 0.791 mmol) was dissolved in 2 mL N,N-dimethylformamide. N,N-Diisopropyl ethyl amine (104 mg; 0.806 mmol) and benzenesulfonyl chloride (155 mg, 0.876 mmol) were added and the reaction mixture was stirred at room temperature overnight. The reaction mixture was poured into 50 mL water and extracted three times with ethyl acetate (50 mL each). The combined organic extracts were dried with sodium sulfate, filtered and evaporated. The residue purified by flash chromatography on silica gel (cyclohexane/ethyl acetate/methanol 100:0:0->0:90:10 gradient). The title compound was obtained as a yellow solid (130 mg, 42%), MS: m/e=394.1 (M+H$^+$).

Example 40

N2-(5-Methyl-furan-2-ylmethyl)-N5-pyridin-2-yl-quinoline-2,5-diamine

The title compound, MS: m/e=331.4 (M+H$^+$), was prepared in accordance with the general method of example 38 from 5-nitro-2-chloroquinoline, 5-methyl-2-furanmethanamine and 2-bromopyridine.

Example 41

(5-Methyl-furan-2-ylmethyl)-(5-phenoxymethyl-quinolin-2-yl)-amine

Step A
2-[(5-Methyl-furan-2-ylmethyl)-amino]-quinoline-5-carbaldehyde (example 21, step A+B, 150 mg, 0.564 mmol) was dissolved in 5 mL ethylendichloride and acetic acid (136 mg, 2.27 mmol) was added. The reaction mixture was stirred at room temperature for 1 h. Sodium triacetoxy borohydride (258 mg, 1.22 mmol) was added and stirring was continued overnight. The reaction mixture was quenched by addition of 50 mL water. The mixture was extracted three times with dichloromethane (50 mL each). The organic phases ware pooled, dried with sodium sulfate, filtered and evaporated. The residue was purified by flash chromatography on silica gel (cyclohexane/ethyl acetate 100:0->50:50 gradient). {2-[(5-Methyl-furan-2-ylmethyl)-amino]-quinolin-5-yl}-methanol was obtained as a light brown solid (105 mg, 69%), MS: m/e=269.5 (M+H$^+$).

Step B

{2-[(5-Methyl-furan-2-ylmethyl)-amino]-quinolin-5-yl}-methanol (180 mg, 672 mmol) was dissolved in 12 mL tetrahydrofurane. Phenol (70 mg, 0.745 mmol) and triphenylphosphine (200 mg, 0.763 mmol) were added at room temperature. Diisopropyl azodicarboxylate (159 mg, 0.787 mmol) was slowly added at 0° C. The reaction mixture was stirred at room temperature overnight. The reaction mixture was quenched by addition of 50 mL 2N sodium carbonate. The mixture was extracted three times with dichloromethane (50 mL each). The organic phases ware pooled, dried with sodium sulfate, filtered and evaporated. The residue was purified by flash chromatography on silica gel (cyclohexane/ethyl acetate 100:0->50:50 gradient). The title compound was obtained as a light brown oil (90 mg, 39%), MS: m/e=345.4 (M+H$^+$).

Example 42

N-{2-[(5-Methyl-furan-2-ylmethyl)-amino]-quinolin-5-yl}-4-fluorobenzenesulfonamide The title compound, MS: m/e=412.4 (M+H$^+$), was prepared in accordance with the general method of example 39 from N$^2$-(5-methyl-furan-2-ylmethyl)-quinoline-2,5-diamine and 4-fluorobenzenesulfonylchloride.

Example 43

(5-Methyl-furan-2-ylmethyl)-[5-((E)-2-pyridin-2-yl-vinyl)-quinolin-2-yl]-amine

The title compound, MS: m/e=342.1 (M+H$^+$), was prepared in accordance with the general method of example 2 from 5-bromo-2-chloroquinoline, 5-methyl-2-furanmethanamine and 2-vinylpyridine.

Example 44

{5-[(E)-2-(4-Fluoro-phenyl)-vinyl]-quinolin-2-yl}-(5-methyl-furan-2-ylmethyl)-amine The title compound, MS: m/e=359.0 (M+H$^+$), was prepared in accordance with the general method of example 2 from 5-bromo-2-chloroquinoline, 5-methyl-2-furanmethanamine and 4-fluorostyrene.

Example 45

N5-(4-Fluoro-phenyl)-N2-(5-methyl-furan-2-ylmethyl)-quinoline-2,5-diamine

The title compound, MS: m/e=348.3 (M+H$^+$), was prepared in accordance with the general method of example 1 from 5-iodo-2-chloroquinoline (CAS 455955-26-7), 5-methyl-2-furanmethanamine and 4-fluoroaniline.

Example 46

(5-Benzylsulfanyl-quinolin-2-yl)-(5-methyl-furan-2-ylmethyl)-amine

The title compound, MS: m/e=361.4 (M+H$^+$), was prepared in accordance with the general method of example 1 from 5-iodo-2-chloroquinoline (CAS 455955-26-7), 5-methyl-2-furanmethanamine and benzylmercaptane.

Example 47

(5-Benzyloxy-quinolin-2-yl)-(5-fluoro-2-methoxy-benzyl)-amine

Step A

5-Quinolinol (5 g, 34.4 mmol) and K$_2$CO$_3$ (5.3 g, 37.8 mmol) were dissolved in acetone (100 mL) under nitrogen and treated with benzylbromid (3.7 mL, 37.8 mmol) at ambient temperature for 18 h. After evaporation the crude reaction mixture was dissolved in water and extracted with ethyl acetate (3×). The combined organic phases were dried over sodium sulfate and concentrated. The residue was subjected to chromatography (heptane:ethyl acetate 4:1/1:1) to yield after drying a yellow oil (2.8 g, 35%).

MS: m/e=236.1 ((M+H$^+$)

Step B

5-Benzyloxy-quinoline (2.8 g, 11.9 mmol) were dissolved in dichloro methane (100 mL) under nitrogen and treated with m-CPBA (70%; 3.2 g, 113.1 mmol) at ambient temperature for 18 h (MS-monitoring). Then water (100 mL) was added and the aqueous phase was adjusted to pH 9 upon addition of sodium carbonate. The aqueous phase was extracted with dichloro methane (3×), the combined organic phases were dried (sodium sulfate addition), filtered and concentrated.

2.6 g (87%) N-oxide were obtained as yellow crystals.

MS: m/e=252.1 ((M+H$^+$)

Step C

Phosphorous oxychloride (5 mL) was heated to 50° C. and 5-benzyloxy-quinoline-1-oxide (2.6 g, 10.3 mmol) were added portion wise. The reaction mixture was stirred for another 30 min at 50° C. and after cooling to ambient temperature poured into a stirred mixture of ice in water. The aqueous phase was extracted with ethyl acetate (3×). The combined organic phases were dried on sodium sulfate, filtered and concentrated. The residue was subjected to column chromatography (SiO$_2$, heptane/ethyl acetate 9:1/4:1/1:1) to yield white crystals (0.39 g, 14%).

MS: m/e=270.4 ((M+H$^+$)

Step D

5-Benzyloxy-2-chloroquinoline (155 mg, 0.56 mmol) and 5-Fluoro-2-methoxybenzylamine (CAS 1978-39-8) (268 mg, 1.68 mmol) were stirred in a sealed tube at 90° C. for 16 hours. The reaction mixture was purified by flash chromatography on silica gel (heptane/ethyl acetate 100:0->50:50 gradient). (5-Benzyloxy-quinolin-2-yl)-(5-fluoro-2-methoxy-benzyl)-amine was obtained as a colorless oil (40 mg, 18%), MS: m/e=389.3 (M+H$^+$).

Example 48

(5-Benzyloxy-quinolin-2-yl)-(2-methoxy-benzyl)-amine

The title compound, MS: m/e=371.4 (M+H$^+$), was prepared in accordance with the general method of example 47 from 5-quinolinol (CAS 578-67-6), benzyl bromide and 2-methoxybenzylamine.

Example 49

N2-(5-Methyl-furan-2-ylmethyl)-N5-pyridin-4-yl-quinoline-2,5-diamine

The title compound, MS: m/e=331.4 (M+H$^+$), was prepared in accordance with the general method of example 1 from 5-iodo-2-chloroquinoline (CAS 455955-26-7), 5-methyl-2-furanmethanamine and 4-aminopyridine.

Example 50

4-Fluoro-N-methyl-N-{2-[(5-methyl-furan-2-ylmethyl)-amino]-quinolin-5-yl}-benzenesulfonamide Step A (5-Iodo-quinolin-2-yl)-(5-methyl-furan-2-ylmethyl)-amine, MS: m/e=365.0 (M+H$^+$), was prepared from 5-iodo-2-chloroquinoline (CAS 455955-26-7) and 5-methyl-2-furanmethanamine as described in example 1 step A.

Step B

N$^5$-Methyl-N$^2$-(5-methyl-furan-2-ylmethyl)-quinoline-2,5-diamine, MS: m/e=268.4 (M+H$^+$), was prepared from (5-iodo-quinolin-2-yl)-(5-methyl-furan-2-ylmethyl)-amine and methylamine (solution in methanol) as described in example 1 step B.

Step C

The title compound, MS: m/e=426.1 (M+H$^+$), was prepared from N$^5$-methyl-N$^2$-(5-methyl-furan-2-ylmethyl)-quinoline-2,5-diamine and 4-fluorobenzene sulphonylchloride as described in example 39.

Example 51

N5-(4-Chloro-phenyl)-N2-(5-methyl-furan-2-ylmethyl)-quinoline-2,5-diamine

The title compound, MS: m/e=364.3 (M+H$^+$), was prepared in accordance with the general method of example 1 from 5-iodo-2-chloroquinoline (CAS 455955-26-7), 5-methyl-2-furanmethanamine and 4-chloroaniline.

Example 52

N5-(3,5-Difluoro-phenyl)-N2-(5-methyl-furan-2-ylmethyl)-quinoline-2,5-diamine

The title compound, MS: m/e=366.1 (M+H$^+$), was prepared in accordance with the general method of example 1 from 5-iodo-2-chloroquinoline (CAS 455955-26-7), 5-methyl-2-furanmethanamine and 3,5-difluoroaniline.

Example 53

[5-(4-Fluoro-benzylsulfanyl)-quinolin-2-yl]-(5-methyl-furan-2-ylmethyl)-amine

The title compound, MS: m/e=379.0 (M+H$^+$), was prepared in accordance with the general method of example 1 from 5-iodo-2-chloroquinoline (CAS 455955-26-7), 5-methyl-2-furanmethanamine and 4-fluorobenzylmercaptane.

Example 54

(5-Methyl-furan-2-ylmethyl)-[5-(2-pyridin-2-yl-ethyl)-quinolin-2-yl]-amine

The title compound, MS: m/e=344.1 (M+H$^+$), was prepared in accordance with the general method of example 4 from (5-methyl-furan-2-ylmethyl)-[5-((E)-2-pyridin-2-yl-vinyl)-quinolin-2-yl]-amine (example 43).

Example 55

{5-[2-(4-Fluoro-phenyl)-ethyl]-quinolin-2-yl}-(5-methyl-furan-2-ylmethyl)-amine

The title compound, MS: m/e=361.4 (M+H$^+$), was prepared in accordance with the general method of example 4 from {5-[(E)-2-(4-fluoro-phenyl)-vinyl]-quinolin-2-yl}-(5-methyl-furan-2-ylmethyl)-amine (example 44).

Example 56

[5-(4-Fluoro-phenylsulfanyl)-quinolin-2-yl]-(5-methyl-furan-2-ylmethyl)-amine

The title compound, MS: m/e=365.0 (M+H$^+$), was prepared in accordance with the general method of example 1 from 5-iodo-2-chloroquinoline (CAS 455955-26-7), 5-methyl-2-furanmethanamine and 4-fluorothiophenol.

Example 57

N5-(6-Chloro-pyridin-3-yl)-N2-(5-methyl-furan-2-ylmethyl)-quinoline-2,5-diamine

The title compound, MS: m/e=365.0 (M+H$^+$), was prepared in accordance with the general method of example 1 from 5-iodo-2-chloroquinoline (CAS 455955-26-7), 5-methyl-2-furanmethanamine and 5-amino-2-chloropyridine.

Example 58

5-Chloro-thiophene-2-sulfonic acid {2-[(5-methyl-furan-2-ylmethyl)-amino]-quinolin-5-yl}-amide Step A (5-Methyl-furan-2-ylmethyl)-(5-nitro-quinolin-2-yl)-amine, MS: m/e=284.3 (M+H$^+$), was prepared from 5-nitro-2-chloroquinoline (CAS 13067-94-2) and 5-methyl-2-furanmethanamine as described in example 1 step A.

Step B

N$^2$-(5-Methyl-furan-2-ylmethyl)-quinoline-2,5-diamine, MS: m/e=254.4 ((M+H$^+$), was prepared from (5-methyl-furan-2-ylmethyl)-(5-nitro-quinolin-2-yl)-amine as described in example 4.

Step C

N²-(5-Methyl-furan-2-ylmethyl)-quinoline-2,5-diamine (200 mg, 0.791 mmol) was dissolved in 2 mL pyridine and 5-chlorothiophene-2-sulfonylchloride (175 mg, 0.806 mmol) was added. The reaction mixture was stirred at room temperature overnight. The reaction mixture was quenched by addition of 50 mL water and 1.2 mL acetic acid. The mixture was extracted three times with ethyl acetate (50 mL each). The organic phases ware pooled, dried with sodium sulfate, filtered and evaporated. The residue was purified by flash chromatography on silica gel (cyclohexane/ethyl acetate 100:0->50:50 gradient). The title compound was obtained as a brown solid (192 mg, 56%), MS: m/e=434.3 (M+H⁺).

Example 59

6-Chloro-pyridine-3-sulfonic acid {2-[(5-methyl-furan-2-ylmethyl)-amino]-quinolin-5-yl}-amide The title compound, MS: m/e=429.1 (M+H⁺), was prepared in accordance with the general method of example 58 from 5-nitro-2-chloroquinoline, 5-methyl-2-furanmethanamine and 6-chloro-pyridine-3-sulfonylchloride.

Example 60

3,5-Difluoro-N-{2-[(5-methyl-furan-2-ylmethyl)-amino]-quinolin-5-yl}-benzenesulfonamide The title compound, MS: m/e=430.5 (M+H⁺), was prepared in accordance with the general method of example 58 from 5-nitro-2-chloroquinoline, 5-methyl-2-furanmethanamine and 3,5-difluorobenzenesulfonylchloride.

Example 61

4-Fluoro-N-[2-(2-methoxy-benzylamino)-quinolin-5-yl]-benzenesulfonamide

Step A

5-Nitro-2-chloroquinoline (CAS 13067-94-2, 5.0 g, 24 mmol) was dissolved in 500 mL ethanol and platinumoxid hydrate (176 mg, 0.718 mmol) was added. He reaction mixture was hydrogenated with a hydrogen balloon at room temperature overnight and filtered. The filtrate was evaporated off. The crude 5-amino-2-chloroquinoline (4.58 g) was used without further purification for the next step.

Step B

5-Amino-2-chloroquinoline (1.0 g, 5.6 mmol) was dissolved in 10 mL pyridine and 4-fluorobenzenesulphonylchloride (1.1 g, 5.7 mmol) was added. The reaction mixture was stirred at room temperature overnight and quenched by addition of 100 mL water and 6.8 mL acetic acid. The mixture was extracted three times with ethyl acetate (100 mL each). The organic phases ware pooled, dried with sodium sulfate, filtered and evaporated. The residue was purified by flash chromatography on silica gel (cyclohexane/ethyl acetate 100:0->50:50 gradient). N-(2-Chloro-quinolin-5-yl)-4-fluoro-benzenesulfonamide was obtained as a brown solid (762 mg, 40%), MS: m/e=337.1 (M+H⁺).

Step C

N-(2-Chloro-quinolin-5-yl)-4-fluoro-benzenesulfonamide (200 mg, 0.593 mmol) and 2-methoxybenzylamine (171 mg, 1.25 mmol) were stirred in a sealed tube at 120° C. overnight. The reaction mixture was purified by flash chromatography on silica gel (cyclohexane/ethyl acetate 100:0->50:50 gradient). The title compound was obtained as a yellow solid (87 mg, 33%), MS: m/e=438.1 ((M+H⁺).

Example 62

4-Fluoro-N-[2-(4-fluoro-benzylamino)-quinolin-5-yl]-benzenesulfonamide

The title compound, MS: m/e=426.0 (M+H⁺), was prepared in accordance with the general method of example 61 from 5-nitro-2-chloroquinoline, 4-fluorobenzenesulphonylchloride and 4-fluorobenzylamine.

Example 63

[5-(4-Fluoro-benzyloxy)-quinolin-2-yl]-(2-methoxy-benzyl)-amine

Step A

2-Chloro-quinolin-5-ol (CAS 124467-35-2) (0.6 g, 3.3 mmol) were dissolved in acetone (15 mL) and potassium carbonate (0.55 g, 4 mmol) were added. After addition of 4-fluoro benzylbromid (0.5 ml, 4 mmol) the reaction mixture was stirred for 18 h at ambient temperature. Then water was added and the mixture was extracted with ethyl acetate (3×). The combined organic phases were dried, filtered and concentrated. The residue was subjected to column chromatography (silica gel, heptane/ethyl acetate 9:1/1:1) to yield white crystals (0.42 g, 44%). MS: m/e=307.3 ((M+H⁺)

Step B

2-Chloro-5-(4-fluoro-benzyloxy)-quinoline (100 mg, 0.35 mmol) and 2-methoxybenzylamine (144 mg, 1.05 mmol) were stirred in a sealed tube at 150° C. for 16 hours. The reaction mixture was purified by flash chromatography on silica gel (heptane/ethyl acetate 100:0->80:20 gradient). 5-(4-Fluorobenzyloxy)-quinolin-2-yl-(2-methoxy-benzyl)-amine was obtained as a yellow oil (57 mg, 42%), MS: m/e=389.3 (M+H⁺).

Example 64

[5-(4-Fluoro-benzyloxy)-quinolin-2-yl]-(5-methyl-furan-2-ylmethyl)-amine

The title compound, MS: m/e=363.3 (M+H⁺), was prepared in accordance with the general method of example 63 from 5-hydroxy-2-chloroquinoline (CAS 124467-35-2), 5-methyl-2-furanmethanamine and 4-fluoro-benzyl bromide.

Example 65

(2-Methoxy-benzyl)-[5-(3-methoxy-benzyloxy)-quinolin-2-yl]-amine

The title compound, MS: m/e=401.3 (M+H⁺), was prepared in accordance with the general method of example 63 from 5-hydroxy-2-chloroquinoline (CAS 124467-35-2), 2-methoxy benzyl amine and 3-methoxy benzyl bromide.

Example 66

[5-(3-Methoxy-benzyloxy)-quinolin-2-yl]-(5-methyl-furan-2-ylmethyl)-amine

The title compound, MS: m/e=375.4 (M+H⁺), was prepared in accordance with the general method of example 63 from 5-hydroxy-2-chloroquinoline (CAS 124467-35-2), 2-methoxy benzyl amine and 5-methyl-2-furanmethanamine.

Example 67

(2-Methoxy-benzyl)-[5-(pyridin-3-ylmethoxy)-quinolin-2-yl]-amine

The title compound, MS: m/e=372.1 (M+H$^+$), was prepared in accordance with the general method of example 63 from 5-hydroxy-2-chloroquinoline (CAS 124467-35-2), 3-pyridyl benzyl bromide and 3-methoxy benzyl amine.

Example 68

(5-Methyl-furan-2-ylmethyl)-[5-(pyridin-3-yl-methoxy)-quinolin-2-yl]-amine

The title compound, MS: m/e=346.3 (M+H$^+$), was prepared in accordance with the general method of example 63 from 5-hydroxy-2-chloroquinoline (CAS 124467-35-2), 3-pyridyl benzyl bromide and 5-methyl-2-furanmethanamine.

Example 69

N5-(4-Methanesulfonyl-phenyl)-N2-(5-methyl-furan-2-ylmethyl)-quinoline-2,5-diamine The title compound, MS: m/e=408.3 (M+H$^+$), was prepared in accordance with the general method of example 1 from 5-iodo-2-chloroquinoline (CAS 455955-26-7), 5-methyl-2-furanmethanamine and 4-methylsulfonylaniline.

Example 70

N5-(3-Methanesulfonyl-phenyl)-N2-(5-methyl-furan-2-ylmethyl)-quinoline-2,5-diamine The title compound, MS: m/e=408.4 (M+H$^+$), was prepared in accordance with the general method of example 1 from 5-iodo-2-chloroquinoline (CAS 455955-26-7), 5-methyl-2-furanmethanamine and 3-methylsulfonylaniline.

Example 71

{5-[2-(4-Fluoro-phenyl)-ethoxyl]-quinolin-2-yl}-(2-methoxy-benzyl)-amine

The title compound, MS: m/e=403.5 (M+H$^+$), was prepared in accordance with the general method of example 63 from 5-hydroxy-2-chloroquinoline (CAS 124467-35-2), 4-fluoro phenethyl bromide and 3-methoxy benzyl amine.

Example 72 rac-5-Chloro-thiophene-2-sulfonic acid {2-[1-(2-methoxy-phenyl)-ethylamino]-quinolin-5-yl}-amide The title compound, MS: m/e=474.1 (M+H$^+$), was prepared in accordance with the general method of example 61 from 5-nitro-2-chloroquinoline, 5-chlorothiophene-2-sulfonylchloride and rac-1-(2-methoxy-phenyl)-ethylamine.

Example 73

3-Fluoro-N-{2-[(5-methyl-furan-2-ylmethyl)-amino]-quinolin-5-yl}-benzenesulfonamide The title compound, MS: m/e=412.1 (M+H$^+$), was prepared in accordance with the general method of example 58 from 5-nitro-2-chloroquinoline, 5-methyl-2-furanmethanamine and 3-fluorobenzenesulfonylchloride.

Example 74

3,4-Difluoro-N-{2-[(5-methyl-furan-2-ylmethyl)-amino]-quinolin-5-yl}-benzenesulfonamide The title compound, MS: m/e=420.3 (M+H$^+$), was prepared in accordance with the general method of example 58 from 5-nitro-2-chloroquinoline, 5-methyl-2-furanmethanamine and 3,4-difluorobenzenesulfonylchloride.

Example 75

[5-(4-Fluoro-phenoxy)-quinolin-2-yl]-(2-methoxy-benzyl)-amine

Step A

Quinolin-5-ol (CAS 124467-35-2) (1.0 g, 6.9 mmol) were dissolved in pyridine (15 mL) and potassium carbonate (0.55 g, 4 mmol), CuO (0.22 mg, 2.8 mmol) and 1-bromo-4-fluorobenzene (1.5 mL, 13.8 mmol) were added. The reaction mixture was stirred for 18 h at 130° C. and then evaporated. The residue was dissolved in dichloro methane, filtered and concentrated. The residue was subjected to column chromatography (silica gel, heptane/ethyl acetate 9:1/4:1/1:1) to yield a yellow oil (0.66 g, 40%).
MS: m/e=240.3 ((M+H$^+$)

Step B 5-(4-Fluoro-phenoxy)-quinoline (0.6 g, 2.5 mmol) were dissolved in dichloro methane (15 mL) under nitrogen and treated with m-CPBA (70%; 0.7 g, 2.8 mmol) at ambient temperature for 18 h (MS-monitoring). Then water (100 mL) was added and the aqueous phase was adjusted to pH 9 upon addition of sodium carbonate. The aqueous phase was extracted with dichloro methane (3×), the combined organic phases were dried (sodium sulfate addition), filtered and concentrated.
0.75 g (117%) N-oxide were obtained as yellow crystals.
MS: m/e=256.4 ((M+H$^+$)

Step C

Phosphorous oxychloride (0.75 mL) was heated to 50° C. and 5-(4-fluoro-phenoxy)quinoline-1-oxide (0.7 g, 2.7 mmol) were added portion wise. The reaction mixture was stirred for another 60 min at 50° C. and after cooling to ambient temperature poured into a stirred mixture of ice in water. The aqueous phase was extracted with ethyl acetate (3×). The combined organic phases were dried on sodium sulfate, filtered and concentrated. The residue was subjected to column chromatography (SiO$_2$, heptane/ethyl acetate 9:1/4:1/1:1) to yield white crystals (0.18 g, 24%).
MS: m/e=274.0 ((M+H$^+$)

Step D

2-Chloro-5-(4-fluoro-phenoxy)-quinoline (60 mg, 0.22 mmol) and 2-methoxybenzylamine (90 mg, 0.66 mmol) were stirred in a sealed tube at 150° C. for 16 hours. The reaction mixture was purified by flash chromatography on silica gel (heptane/ethyl acetate 100:0->75:25 gradient). (5-(4-Fluoro-phenoxy)-quinolin-2-yl)-(2-methoxy-benzyl)-amine was obtained as a yellow oil (56 mg, 68%), MS: m/e=375.4 (M+H$^+$).

Example 76

[5-(4-Chloro-benzenesulfonylmethyl)-quinolin-2-yl]-(5-methyl-furan-2-ylmethyl)-amine Step A {2-[(5-Methyl-furan-2-ylmethyl)-amino]-quinolin-5-yl}-methanol (example 41, step A, 70 mg, 0.261 mmol) was dissolved in 2 mL tetrahydrofurane and methanesulfonyl chloride (34 mg, 0.297 mmol) and N,N-diisopropyl ethyl amine (41 mg, 0.318 mmol) were added. The reaction mixture was stirred at room temperature overnight and the solvent was evaporated off. The residue was purified by flash chromatography on silica gel (cyclohexane/ethyl acetate 100:0->50:50 gradient). (5-Chloromethyl-quinolin-2-yl)-(5-methyl-furan-2-ylmethyl)-amine was obtained as a brown solid (59 mg, 79%), MS: m/e=287.0 (M+H$^+$).

Step B (5-Chloromethyl-quinolin-2-yl)-(5-methyl-furan-2-ylmethyl)-amine (55 mg, 0.192 mmol) were dissolved in 1 mL dimethylformamide and 4-chlorobenzenesulphinic acid sodium salt (47 mg, 0.237 mmol) was added. The reaction mixture was stirred at 60° C. for 3 h. Water was added until a suspension was formed and the mixture was stirred for 15 min. The solid was filtered off and dried. The title compound was obtained as a brown solid (53 mg, 65%), MS: m/e=427.4 (M+H$^+$).

Example 77

3,5-Difluoro-N-[2-(2-phenoxy-ethylamino)-quinolin-5-yl]-benzenesulfonamide

The title compound, MS: m/e=456.4 (M+H$^+$), was prepared in accordance with the general method of example 61 from 5-nitro-2-chloroquinoline, 3,5-difluorophenyl-sulfonylchloride and 2-phenoxyethylamine.

Example 78

3,5-Difluoro-N-[2-(3-trifluoromethyl-phenylamino)-quinolin-5-yl]-benzenesulfonamide The title compound, MS: m/e=480.4 (M+H$^+$), was prepared in accordance with the general method of example 61 from 5-nitro-2-chloroquinoline, 3,5-difluorophenyl-sulfonylchloride and 3-aminobenzotrifluoride.

Example 79

(2-Methoxy-benzyl)-{5-[2-(3-methoxy-phenyl)-ethoxyl]-quinolin-2-yl}-amine

The title compound, MS: m/e=415.5 (M+H$^+$), was prepared in accordance with the general method of example 63 from 5-hydroxy-2-chloroquinoline (CAS 124467-35-2), 3-methoxy phenethyl bromide and 3-methoxy benzyl amine.

Example 80

3,4,5-Trifluoro-N-{2-[(R)-1-(2-methoxy-phenyl)-ethylamino]-quinolin-5-yl}-benzenesulfonamide The title compound, MS: m/e=488.3 (M+H$^+$), was prepared in accordance with the general method of example 61 from 5-nitro-2-chloroquinoline, 3,4,5-trifluorobenzenesulfonylchloride and (R)-2-methoxy-alpha-methylbenzylamine.

Example 81

3,4,5-Trifluoro-N-{2-[2-(2-methoxy-phenyl)-ethylamino]-quinolin-5-yl}-benzenesulfonamide The title compound, MS: m/e=488.5 (M+H$^+$), was prepared in accordance with the general method of example 61 from 5-nitro-2-chloroquinoline, 3,4,5-trifluorobenzenesulfonylchloride and 2-(2-methoxyphenyl)ethylamine.

Example 82

4-Fluoro-N-[2-(2-methylsulfanyl-benzylamino)-quinolin-5-yl]-benzenesulfonamide

The title compound, MS: m/e=454.3 (M+H$^+$), was prepared in accordance with the general method of example 61 from 5-nitro-2-chloroquinoline, 4-fluorobenzenesulfonylchloride and 2-(methylthio)benzylamine.

Example 83

[5-(2-Benzenesulfinyl-ethoxy)-quinolin-2-yl]-(2-methoxy-benzyl)-amine

Step A (5-Iodo-quinolin-2-yl)-(2-methoxy-benzyl)-amine, MS: m/e=391.0 (M+H$^+$), was prepared from 5-iodo-2-chloroquinoline (CAS 455955-26-7) and 2-methoxy-benzylamine as described in example 1 step A.

Step B (5-Iodo-quinolin-2-yl)-(2-methoxy-benzyl)-amine (0.4 g, 1 mMol) and 2-hydroxyethyl-phenylsulfide (0.32 g, 2 mMol) were heated in toluene together with CuI (10 Mol-%), phenantroline (20 Mol-%) and CsCO$_3$ (0.67 g, 2 mMol) to 100° C. for 24 h. After cooling to ambient temperature the reaction mixture was extracted twice with toluene, the combined organic phases were extracted with water and subsequently dried with sodium sulfate. After evaporation the residue was subjected to column chromatography (silica gel, heptane/ethyl acetate 100:0->60:40 gradient) to yield (2-methoxy-benzyl)-[5-(2-phenylsulfanyl-ethoxy)-quinolin-2-yl]-amine (0.4 g, 93%) as a yellow oil, MS: m/e=417.0 (M+H$^+$).

Step C (2-Methoxy-benzyl)-[5-(2-phenylsulfanyl-ethoxy)-quinolin-2-yl]-amine (0.29 g, 0.7 mMol) were treated with m-chloroperbenzoic-acid (0.395 g, 1.6 mMol) in methylene chloride at ambient temperature for 1.5 h. The reaction mixture was washed with sodium carbonate (20%), the aqueous phase was extracted with methylene chloride, the combined organic phases were washed with water and tried on sodium sulfate. After evaporation the residue was subjected to column chromatography on silica gel (heptane/ethyl acetate 100:0->10:90 gradient). The second fraction isolated yielded [5-

(2-benzenesulfonyl-ethoxy)-quinolin-2-yl]-(2-methoxy-benzyl)-amine (0,015 g, 6%) as a yellow solid; MS: m/e=449.0 (M+H$^+$).

Example 84

[5-(2-Benzenesulfonyl-ethoxy)-quinolin-2-yl]-(2-methoxy-benzyl)-amine

From step C of the above described procedure (example 83) the title compound [5-(2-Benzenesulfonyl-ethoxy)-quinolin-2-yl]-(2-methoxy-benzyl)-amine was isolated as the second fraction eluting in column chromatography as a white solid (0.032 g, 11%); MS: m/e=433.0 (M+H$^+$).

Example 85

3,5-Difluoro-N-{2-[(5-methyl-thiophen-2-ylmethyl)-amino]-quinolin-5-yl}-benzenesulfonamide The title compound, MS: m/e=446.1 (M+H$^+$), was prepared in accordance with the general method of example 61 from 5-nitro-2-chloroquinoline, 4-3,5-difluorobenzenesulfonylchloride and 5-methylthiophene-2-ylmethylamine.

Example 86

3,5-Difluoro-N-{2-[1-(5-methyl-furan-2-yl)-ethylamino]-quinolin-5-yl}-benzenesulfonamide The title compound, MS: m/e=444.4 (M+H$^+$), was prepared in accordance with the general method of example 61 from 5-nitro-2-chloroquinoline, 3,5-difluorobenzenesulfonylchloride and 1-(5-methyl-2-furyl) ethanamine.

Example 87

N5-(1H-Imidazol-4-ylmethyl)-N2-(5-methyl-furan-2-ylmethyl)-quinoline-2,5-diamine The title compound, MS: m/e=334.5 (M+H$^+$), was prepared from 5-nitro-2-chloroquinoline, 5-methyl-2-furanmethanamine and 4(5)-formylimidazole as described in example 26.

Example 88

N2-(5-Methyl-furan-2-ylmethyl)-N5-(1H-pyrazol-3-ylmethyl)-quinoline-2,5-diamine

The title compound, MS: m/e=334.3 (M+H$^+$), was prepared from 5-nitro-2-chloroquinoline, 5-methyl-2-furanmethanamine and pyrazol-3-carbaldehyde as described in example 26.

Example 89

3,5-Difluoro-N-[2-(2-methyl-benzofuran-7-ylamino)-quinolin-5-yl]-benzenesulfonamide The intermediate N-(2-chloro-quinolin-5-yl)-3,5-difluoro-benzenesulfonamide was prepared in accordance with the general method of example 61, step A and B from 5-nitro-2-chloroquinoline, 3,5-difluorobenzenesulfonylchloride. N-(2-Chloro-quinolin-5-yl)-3,5-difluoro-benzenesulfonamide (150 mg, 0.423 mmol) was dissolved in 3 mL dioxane. Argon was bubbled through the solution for 2 minutes to remove oxygen. (2-Methyl-1-benzofuran-7-yl)amine (245 mg, 1.33 mmol), sodium tert.-butylate (230 mg, 2.40 mmol), 1,1'-bis(diphenylphosphin)ferrocen (36 mg, 0.06 mmol) and 1,1'-bis(diphenylphosphin)ferrocen-palladium(II)chloride (17 mg, 0.02 mmol) were added. The reaction mixture was stirred in a sealed tube at 100° C. for 16 h. The solvent was evaporated and the residue purified by flash chromatography on silica gel (heptane/ethyl acetate 100:0->60:40 gradient). The title compound was obtained as a light brown solid (164 mg, 83%), MS: m/e=466.0 (M+H$^+$).

Example 90

N2-(5-Methyl-furan-2-ylmethyl)-N5-(2-methyl-1H-imidazol-4-ylmethyl)-quinoline-2,5-diamine The title compound, MS: m/e=348.5 (M+H$^+$), was prepared from 5-nitro-2-chloroquinoline, 5-methyl-2-furanmethanamine and 2-methyl-1H-imidazole-carbaldehyde as described in example 26.

Example 91

N5-(1H-Indol-4-ylmethyl)-N2-(5-methyl-furan-2-ylmethyl)-quinoline-2,5-diamine

The title compound, MS: m/e=383.1 (M+H$^+$), was prepared from 5-nitro-2-chloroquinoline, 5-methyl-2-furanmethanamine and 4-formylindole as described in example 26.

Example 92

N2-(5-Methyl-furan-2-ylmethyl)-N5-(5-methyl-1H-imidazol-4-ylmethyl)-quinoline-2,5-diamine The title compound, MS: m/e=348.5 (M+H$^+$), was prepared from 5-nitro-2-chloroquinoline, 5-methyl-2-furanmethanamine and 4-methylimidazole-5-carbaldehyde as described in example 26.

Example 93

N5-(1H-Indol-7-yl)-N2-(5-methyl-furan-2-ylmethyl)-quinoline-2,5-diamine

The title compound, MS: m/e=369.1 (M+H$^+$), was prepared in accordance with the general method of example 1 from 5-iodo-2-chloroquinoline, 5-methyl-2-furanmethanamine and 7-aminoindole.

Example 94

N5-(1H-Indol-4-yl)-N2-(5-methyl-furan-2-ylmethyl)-quinoline-2,5-diamine

The title compound, MS: m/e=369.4 (M+H$^+$), was prepared in accordance with the general method of example 1 from 5-iodo-2-chloroquinoline, 5-methyl-2-furanmethanamine and 4-aminoindole.

Example 95

N2-(5-Methyl-furan-2-ylmethyl)-N5-(1-methyl-1H-pyrrol-2-ylmethyl)-quinoline-2,5-diamine The title compound, MS: m/e=347.3 (M+H$^+$), was prepared from 5-nitro-2-chloroquinoline, 5-methyl-2-furanmethanamine and 1-methylpyrrol-2-carbaldehyde as described in example 26.

Example 96

N2-(2-Methoxy-benzyl)-N5-(5-methyl-3H-imidazol-4-ylmethyl)-quinoline-2,5-diamine The title compound, MS: m/e=374.4 (M+H$^+$), was prepared from 5-nitro-2-chloroquinoline, 2-methoxybenzylamine and 4-methyl-5-imidazole-carboxaldehyde as described in example 26.

Example 97

N2-(2-Methoxy-benzyl)-N5-(2-methyl-3H-imidazol-4-ylmethyl)-quinoline-2,5-diamine The title compound, MS: m/e=374.4 (M+H$^+$), was prepared from 5-nitro-2-chloroquinoline, 2-methoxybenzylamine and 2-methyl-1H-imidazole-4-carbaldehyde as described in example 26.

Example 98

N2-(2-Methoxy-benzyl)-N5-(1H-pyrazol-3-ylmethyl)-quinoline-2,5-diamine

The title compound, MS: m/e=360.4 (M+H$^+$), was prepared from 5-nitro-2-chloroquinoline, 2-methoxybenzylamine and pyrazole-3-carbaldehyde as described in example 26.

Example 99

N2-(2,6-Dimethoxy-benzyl)-N5-pyridin-3-ylmethyl-quinoline-2,5-diamine

The title compound, MS: m/e=401.4 (M+H$^+$), was prepared in accordance with the general method of example 1 from 5-iodo-2-chloroquinoline, 2,6-dimethoxybenzylamine and 3-(aminomethyl)pyridine.

Example 100

N2-(5-Methyl-furan-2-ylmethyl)-N5-thiazol-2-ylmethyl-quinoline-2,5-diamine

The title compound, MS: m/e=351.4 (M+H$^+$), was prepared from 5-nitro-2-chloroquinoline, 5-methyl-2-furanmethanamine and 2-formylthiazole as described in example 26.

Example 101

N5-(3H-Imidazol-4-ylmethyl)-N2-(2-methoxy-benzyl)-quinoline-2,5-diamine

The title compound, MS: m/e=360.4 (M+H$^+$), was prepared from 5-nitro-2-chloroquinoline, 2-methoxybenzylamine and 4(5)-imidazole-carboxaldehyde as described in example 26.

Example 102

N5-(1H-Indol-4-ylmethyl)-N2-(2-methoxy-benzyl)-quinoline-2,5-diamine

The title compound, MS: m/e=409.5 (M+H$^+$), was prepared from 5-nitro-2-chloroquinoline, 2-methoxybenzylamine and 4-indole-carboxaldehyde as described in example 26.

Example 103

N5-Benzo[1,3]dioxol-4-ylmethyl-N2-(5-methyl-furan-2-ylmethyl)-quinoline-2,5-diamine The title compound, MS: m/e=388.4 (M+H$^+$), was prepared from 5-nitro-2-chloroquinoline, 5-methyl-2-furanmethanamine and 2,3-(methylenedioxy)benzaldehyde as described in example 26.

Example 104

N5-(4-Methyl-3,4-dihydro-2H-benzo[1,4]oxazin-7-ylmethyl)-N2-(5-methyl-furan-2-ylmethyl)-quinoline-2,5-diamine The title compound, MS: m/e=388.4 (M+H$^+$), was prepared from 5-nitro-2-chloroquinoline, 5-methyl-2-furanmethanamine and 4-methyl-3,4-dihydro-2H-1,4-benzoxazine-7-carbaldehyde as described in example 26.

Example 105

N2-(5-Methyl-furan-2-ylmethyl)-N5-[2-(4-methyl-piperazin-1-yl)-benzyl]-quinoline-2,5-diamine The title compound, MS: m/e=442.5 (M+H$^+$), was prepared from 5-nitro-2-chloroquinoline, 5-methyl-2-furanmethanamine and 2-(4-methylpiperazino)benzaldehyde as described in example 26.

Example 106

N2-(2-Methoxy-benzyl)-N5-(1H-[1,2,3]triazol-4-ylmethyl)-quinoline-2,5-diamine

The title compound, MS: m/e=361.5 (M+H$^+$), was prepared from 5-nitro-2-chloroquinoline, 2-methoxybenzylamine and 1H-[1,2,3]triazole-4-carbaldehyde as described in example 26.

Example 107

N5-(1H-Benzoimidazol-5-ylmethyl)-N2-(5-methyl-furan-2-ylmethyl)-quinoline-2,5-diamine The title compound, MS: m/e=384.1 (M+H$^+$), was prepared from 5-nitro-2-chloroquinoline, 5-methyl-2-furanmethanamine and 1H-benzimidazole-5-carbaldehyde as described in example 26.

Example 108

4-Fluoro-N-[2-(2-trifluoromethoxy-benzylamino)-quinolin-5-yl]-benzenesulfonamide The title compound, MS: m/e=491.8 (M+H$^+$), was prepared in accordance with the general method of example 89 from 5-nitro-2-chloroquinoline, 4-fluorobenzenesulfonylchloride and 2-(trifluoromethoxy)benzylamine.

Example 109

N2-(2,6-Dimethoxy-benzyl)-N5-(1H-indol-4-ylmethyl)-quinoline-2,5-diamine

The title compound, MS: m/e=439.3 (M+H$^+$), was prepared in accordance with the general method of example 1 from 5-iodo-2-chloroquinoline, 2,6-dimethoxybenzylamine and 4-aminomethylindole.

Example 110

N2-(2-Methoxy-benzyl)-N5-thiazol-2-ylmethyl-quinoline-2,5-diamine

The title compound, MS: m/e=377.4 (M+H$^+$), was prepared from 5-nitro-2-chloroquinoline, 2-methoxybenzylamine and thiazole-2-carbaldehyde as described in example 26.

Example 111

N5-(1H-Indol-4-ylmethyl)-N2-(2-methyl-benzofuran-7-yl)-quinoline-2,5-diamine

The title compound, MS: m/e=419.1 (M+H$^+$), was prepared in accordance with the general method of example 1 from 5-iodo-2-chloroquinoline, (2-methyl-1-benzofuran-7-yl)amine and 4-aminomethylindole.

Example 112

N2-(5-Methyl-furan-2-ylmethyl)-N5-(5-methyl-1H-pyrazol-3-yl)-quinoline-2,5-diamine The title compound, MS: m/e=334.5 (M+H$^+$), was prepared in accordance with the general method of example 1 from 5-iodo-2-chloroquinoline, 5-methyl-2-furanmethanamine and 3-amino-5-methylpyrazole.

Example 113

N5-(1H-Indol-4-yl)-N2-(2-methyl-benzofuran-7-yl)-quinoline-2,5-diamine

The title compound, MS: m/e=405.4 (M+H$^+$), was prepared in accordance with the general method of example 1 from 5-iodo-2-chloroquinoline, (2-methyl-1-benzofuran-7-yl)amine and 4-aminoindole.

Example 114

N5-(3H-Benzoimidazol-5-ylmethyl)-N2-(2-methoxy-benzyl)-quinoline-2,5-diamine

The title compound, MS: m/e=410.1 (M+H$^+$), was prepared from 5-nitro-2-chloroquinoline, 2-methoxybenzylamine and 3H-benzimidazole-5-carbaldehyde as described in example 26.

Example 115

N2-(5-Methyl-furan-2-ylmethyl)-N5-(3H-[1,2,3]triazol-4-ylmethyl)-quinoline-2,5-diamine The title compound, MS: m/e=335.4 (M+H$^+$), was prepared from 5-nitro-2-chloroquinoline, 5-methyl-2-furanmethanamine and 1H-1,2,3-triazole-4-carbaldehyde as described in example 26.

Example 116

N5-(1H-Indol-4-ylmethyl)-N2-(2-trifluoromethoxy-benzyl)-quinoline-2,5-diamine

The title compound, MS: m/e=463.0 (M+H$^+$), was prepared from 5-nitro-2-chloroquinoline, 2-(trifluoromethoxy)benzylamine and 4-formylindole as described in example 26.

Example 117

N5-(1H-Benzoimidazol-5-ylmethyl)-N2-(2-trifluoromethoxy-benzyl)-quinoline-2,5-diamine The title compound, MS: m/e=464.0 (M+H$^+$), was prepared from 5-nitro-2-chloroquinoline, 2-(trifluoromethoxy)benzylamine and 1H-benimidazole-5-carbaldehyde as described in example 26.

Example 118

N2-(2,3-Dihydro-benzo[1,4]dioxin-5-ylmethyl)-N5-(1H-indol-4-ylmethyl)-quinoline-2,5-diamine The title compound, MS: m/e=437.4 (M+H$^+$), was prepared in accordance with the general method of example 1 from 5-iodo-2-chloroquinoline, 2,3-dihydro-1,4-benzodioxin-5-ylmethylamine and 4-aminomethylindole.

Example 119

N5-(7-Fluoro-1H-indol-4-yl)-N2-(5-methyl-furan-2-ylmethyl)-quinoline-2,5-diamine The title compound, MS: m/e=387.1 (M+H$^+$), was prepared in accordance with the general method of example 38 from 5-nitro-2-chloroquinoline, 5-methyl-2-furanmethanamine and 4-bromo-7-fluoroindole.

Example 120

N5-(3,5-Difluoro-benzyl)-N2-(5-methyl-furan-2-ylmethyl)-quinoline-2,5-diamine

The title compound, MS: m/e=380.3 (M+H$^+$), was prepared in accordance with the general method of example 1 from 5-iodo-2-chloroquinoline, 5-methyl-2-furanmethanamine and 3,5-difluorobenzylamine.

Example 121

N-[2-(2,3-Dihydro-benzo[1,4]dioxin-5-ylamino)-quinolin-5-yl]-3,5-difluoro-benzenesulfonamide The title compound, MS: m/e=470.3 (M+H$^+$), was prepared in accordance with the general method of example 89 from 5-nitro-2-chloroquinoline, 3,5-difluorobenzenesulfonylchloride and 5-amino-1,4-benzodioxane.

Example 122

3,5-Difluoro-N-[2-(naphthalen-1-ylamino)-quinolin-5-yl]-benzenesulfonamide

The title compound, MS: m/e=462.3 (M+H$^+$), was prepared in accordance with the general method of example 89 from 5-nitro-2-chloroquinoline, 3,5-difluorobenzenesulfonylchloride and 1-naphthylamine.

Example 123

3,5-Difluoro-N-[2-(indan-4-ylamino)-quinolin-5-yl]-benzene sulfonamide

The title compound, MS: m/e=452.0 (M+H$^+$), was prepared in accordance with the general method of example 89 from 5-nitro-2-chloroquinoline, 3,5-difluorobenzenesulfonylchloride and 4-aminoindane.

Example 124

N5-(1H-Benzoimidazol-5-ylmethyl)-N2-(2-methyl-benzofuran-7-yl)-quinoline-2,5-diamine The title compound, MS: m/e=420.1 (M+H$^+$), was prepared from 5-nitro-2-chloroquinoline, (2-methyl-1-benzofuran-7-yl) amine and 1H-benzimidazole-5-carboxaldehyde as described in example 26.

Example 125

N2-(2-Methyl-benzofuran-7-yl)-N5-(5-methyl-3H-imidazol-4-ylmethyl)-quinoline-2,5-diamine The title compound, MS: m/e=384.1 (M+H$^+$), was prepared from 5-nitro-2-chloroquinoline, (2-methyl-1-benzofuran-7-yl)amine and 4-methyl-1H-imidazole-5-carbaldehyde as described in example 26.

Example 126

4-Fluoro-N-{2-[(5-methyl-furan-2-ylmethyl)-amino]-quinolin-5-ylmethyl}-benzamide Step A A stirred mixture of (5-iodo-quinolin-2-yl)-(5-methyl-furan-2-ylmethyl)-amine (example 50, step A) (500 mg, 1.37 mmol), zinc cyanide (177 mg, 1.5 mmol) and tetrakis-(triphenylphosphine)-palladium (159 mg, 0.14 mmol) in DMF (5 ml) was heated at 160° C. for 15 min in a microwave reactor. The reaction mixture was poured into water (15 ml) and extracted with ethyl acetate (2×10 ml). The combined organic layers were washed with brine (10 ml), dried (MgSO$_4$) and evaporated. The crude product was purified by flash chromatography (ethyl acetate/heptane) on silica gel to yield 2-[(5-methyl-furan-2-ylmethyl)-amino]-quinoline-5-carbonitrile as light brown solid (346 mg, 91%).

M.p. 102° C.; MS: m/e=262.0 (M–H).

Step B

Hydrogenation of 2-[(5-methyl-furan-2-ylmethyl)-amino]-quinoline-5-carbonitrile (200 mg, 0.76 mmol) dissolved in 7N MeOH—NH$_3$ for 23 h at room temperature yielded after removal of the catalyst by filtration and evaporation a yellow oil which was further purified by column chromatography (dichloromethane/MeOH/NH$_4$OH 15:1:0.1) on silica gel to yield (5-aminomethyl-quinolin-2-yl)-(5-methyl-furan-2-ylmethyl)-amine as light yellow oil (198 mg, 98%).

MS: m/e=268.2 (M+H$^+$).

Step C

To a cooled (ice bath) and stirred solution of (5-aminomethyl-quinolin-2-yl)-(5-methyl-furan-2-ylmethyl)-amine (95 mg, 0.355 mmol) and triethyl amine (39.6 mg, 0.39 mmol) in THF (2 ml) was added 4-fluorobenzoyl chloride (62 mg, 0.39 mmol) and the mixture was allowed to stir at room temperature for 16 h. Evaporation and purification by flash chromatography (ethyl acetate/heptane) on silica gel yielded the title compound as off-white solid (67 mg, 48%).

M.p. 173° C.; MS: m/e=390.3 (M+H$^+$).

Example 127

{5-[(4-Fluoro-benzylamino)-methyl]-quinolin-2-yl}-(5-methyl-furan-2-ylmethyl)-amine A solution of (5-aminomethyl-quinolin-2-yl)-(5-methyl-furan-2-ylmethyl)-amine (example 126, step B) (95 mg, 0.355 mmol), 4-fluorobenzaldehyde (97 mg, 0.78 mmol) and acetic acid (85.4 mg, 1.42 mmol) in 1,1-dichloroethane (5 ml) was stirred at room temperature for 30 min. Afterwards sodium triacetoxy-boron hydride (176 mg, 0.75 mmol) was added, the reaction mixture was allowed to stir for 21 h at room temperature, poured into ice/saturated NaHCO$_3$ solution (20 ml) and extracted with ethyl acetate (2×30 ml). The combined organic layers were washed with brine (20 ml), dried (MgSO$_4$) and evaporated. The crude product was purified by flash chromatography (ethyl acetate/heptane) on silica gel to yield beside 5-{[bis-(4-fluoro-benzyl)-amino]-methyl}-quinolin-2-yl)-(5-methyl-furan-2-ylmethyl)-amine (114 mg, 66%) the title compound as light yellow oil (30 mg, 22%).

MS: m/e=376.4 (M+H$^+$).

Example 128

4-Fluoro-N-[2-(2-methyl-benzofuran-7-ylamino)-quinolin-5-yl]-benzenesulfonamide

The title compound, MS: m/e=448.0 (M+H$^+$), was prepared in accordance with the general method of example 58 from 5-nitro-2-chloroquinoline, (2-methyl-1-benzofuran-7-yl)amine and 4-fluorobenzenesulfonylchloride.

Example 129

N2-(2-Methyl-benzofuran-7-yl)-N5-pyridin-3-ylmethyl-quinoline-2,5-diamine

The title compound, MS: m/e=381.0 (M+H$^+$), was prepared from 5-nitro-2-chloroquinoline, (2-methyl-1-benzofuran-7-yl)amine and pyridine-3-carbaldehyde as described in example 26.

Example 130

5-Chloro-thiophene-2-sulfonic acid [2-(2-methyl-benzofuran-7-ylamino)-quinolin-5-yl]-amide The title compound, MS: m/e=470.1 (M+H$^+$), was prepared in accordance with the general method of example 58 from 5-nitro-2-chloroquinoline, (2-methyl-1-benzofuran-7-yl)amine and 4-chlorothiophene-2-sulfonylchloride.

Example 131

N5-(3H-Imidazol-4-ylmethyl)-N2-(2-methyl-benzofuran-7-yl)-quinoline-2,5-diamine The title compound, MS: m/e=370.0 (M+H$^+$), was prepared from 5-nitro-2-chloroquinoline, (2-methyl-1-benzofuran-7-yl)amine and 4(5)-imidazole-carbaldehyde as described in example 26.

Example 132

N5-(3,5-Difluoro-benzyl)-N2-(2-methyl-benzofuran-7-yl)-quinoline-2,5-diamine The title compound, MS: m/e=416.4 (M+H$^+$), was prepared from 5-nitro-2-chloroquinoline, (2-methyl-1-benzofuran-7-yl)amine and 3,5-difluorobenzaldehyde as described in example 26.

Example 133

N5-(4-Fluoro-phenyl)-N2-(2-methyl-benzofuran-7-yl)-quinoline-2,5-diamine

The title compound, MS: m/e=384.1 (M+H$^+$), was prepared in accordance with the general method of example 38 from 5-nitro-2-chloroquinoline, (2-methyl-1-benzofuran-7-yl)amine and 1-bromo-4-fluorobenzene.

Example 134 rac-3,5-Difluoro-N-[2-(2-methyl-2,3-dihydro-benzofuran-7-ylamino)-quinolin-5-yl]-benzenesulfonamide The title compound, MS: m/e=468.3 (M+H$^+$), was prepared in accordance with the general method of example 89 from 5-nitro-2-chloroquinoline, 3,5-difluorobenzenesulfonylchloride and 2,3-dihydro-2-methyl-7-benzofuranamine (CAS 26210-74-2).

Example 135 rac-N2-(5-Methyl-furan-2-ylmethyl)-N5-thiochroman-4-yl-quinoline-2,5-diamine The title compound, MS: m/e=402.5 (M+H$^+$), was prepared from 5-nitro-2-chloroquinoline, 5-methyl-2-furanmethanamine and thiochroman-4-one as described in example 26.

Example 136

{5-[(4-Fluoro-phenyl)-imino-methyl]-quinolin-2-yl}-(2-methoxy-benzyl)-amine

Step A (5-Iodo-quinolin-2-yl)-(2-methoxy-benzyl)-amine, light brown oil; MS: m/e=391.0 (M+H$^+$), was prepared from 5-iodo-2-chloroquinoline (CAS 455955-26-7) and 2-methoxybenzylamine as described in example 1 step A.

Step B 2-(2-Methoxy-benzylamino)-quinoline-5-carbonitrile, light yellow solid; MS: m/e 288.3 (M−H$^−$); m.p. 133° C., was prepared from (5-iodo-quinolin-2-yl)-(2-methoxy-benzyl)-amine as described in example 126, step A.

Step C

To a cooled (ice bath) and stirred suspension of 2-(2-methoxy-benzylamino)-quinoline-5-carbonitrile (289 mg, 1.0 mmol) in diethylether (3 ml) and THF (1 ml) was added drop wise a 1M solution of 4-fluorophenyl-magnesium bromide (4 ml, 4.0 mmol), the reaction mixture was heated under reflux conditions for 24 h and poured into ice-water (15 ml). 2N HCl (5 ml) was added, the mixture was stirred at room temperature for 10 min, 3 N NaOH (5 ml) was added and the mixture was extracted with ethyl acetate (2×40 ml). The combined organic layers were washed with brine (2×20 ml), dried (MgSO$_4$) and evaporated. The crude product was purified by flash chromatography (ethyl acetate/heptane) on silica gel and crystallization (dichloromethane/hexane) to yield the title compound as white solid (159 mg, 41%).

MS: m/e=386.2 (M+H$^+$); m.p. 155° C.

Example 137

(4-Fluoro-phenyl)-[2-(2-methoxy-benzylamino)-quinolin-5-yl]-methanone

A mixture of {5-[(4-fluoro-phenyl)-imino-methyl]-quinolin-2-yl}-(2-methoxy-benzyl)-amine (130 mg, 0.34 mmol), 2N HCl (4 ml) and THF (1 ml) was stirred at room temperature for 23 h, poured into saturated NaHCO$_3$ solution (20 ml) and extracted with ethyl acetate (2×30 ml). The combined organic layers were washed with brine (20 ml), dried (MgSO$_4$) and evaporated. The crude product was purified by flash chromatography (ethyl acetate/heptane) on silica gel to yield the title compound as light yellow gum (115 mg, 88%).

MS: m/e=387.2 (M+H$^+$).

Example 138

N-[2-(2-tert-Butyl-benzofuran-7-ylamino)-quinolin-5-yl]-3,5-difluoro-benzenesulfonamide The title compound, MS: m/e=508.1 (M+H$^+$), was prepared in accordance with the general method of example 89 from 5-nitro-2-chloroquinoline, 3,5-difluorobenzenesulfonylchloride and 2-tert-butyl-benzofuran-7-ylamine.

2-tert-Butyl-benzofuran-7-ylamine was prepared in 2 steps from 2-bromo-6-nitrophenol Step A:

2-Bromo-6-nitrophenol (500 mg, 2.29 mmol), bis(acetonitrile) palladium (II) chloride (12 mg, 0.05 mmol), 2-dicylohexylphosphino-2',4',6'-triisopropylbiphenyl (68 mg, 0.14 mmol), cesium carbonate (1.95 g, 6 mmol) and tert-butylacetylene (577 mg, 7 mmol) were dissolved 5 mL acetonitrile in a sealed tube and heated at 75° C. overnight. The reaction mixture was directly chromatographed (silica gel, heptane/ethyl acetate 9:1/4:1/1:1) to yield 2-tert-butyl-7-nitro-benzofuran as an off-white solid (185 mg, 37%).

Step B:

2-tert-Butyl-7-nitro-benzofuran (180 mg, 0.802 mmol) was dissolved in 2.5 mL methanol and Raney nickel (5 mg, 0.08 mmol) and hydrazine (126 mg, 2.5 mmol) were added. The reaction mixture was refluxed for 2 hours and filtered. The solvent was evaporated off and the crude 2-tert-butyl-benzofuran-7-ylamine (160 mg, 100%) was used for the next step.

Example 139

N-[2-(2,3-Dihydro-benzofuran-7-ylamino)-quinolin-5-yl]-3,5-difluoro-benzenesulfonamide The title compound, MS: m/e=454.3 (M+H$^+$), was prepared in accordance with the general method of example 89 from 5-nitro-2-chloroquinoline, 3,5-difluorobenzenesulfonylchloride and 7-amino-2,3-dihydrobenzofuran (CAS 13414-56-7).

Example 140

N5-(1H-Indol-4-ylmethyl)-N2-(2-methyl-2,3-dihydro-benzofuran-7-yl)-quinoline-2,5-diamine The title compound, MS: m/e=421.4 (M+H$^+$), was prepared from 5-nitro-2-chloroquinoline, 2,3-dihydro-2-methyl-7-benzofuranamine (CAS 26210-74-2) and indole-4-carbaldehyde as described in example 26.

Example 141

N-[2-(2,2-Dimethyl-2,3-dihydro-benzofuran-7-ylamino)-quinolin-5-yl]-3,5-difluoro-benzene-sulfonamide The title compound, MS: m/e=482.1 (M+H$^+$), was prepared in accordance with the general method of example 89 from 5-nitro-2-chloroquinoline, 3,5-difluorobenzenesulfonylchloride and 7-amino-2,3-dihydro-2,2-dimethylbenzofuran (CAS 68298-46-4).

Example 142 rac-N5-Chroman-4-yl-N2-(5-methyl-furan-2-ylmethyl)-quinoline-2,5-diamine

The title compound, MS: m/e=386.3 (M+H$^+$), was prepared in accordance with the general method of example 1 from 5-iodo-2-chloroquinoline, 5-methyl-2-furanmethanamine and 3,4-dihydro-2H-chromen-4-ylamine.

Example 143 rac-5-(1,1-Dioxo-1l6-thiochroman-4-yl)-N2-(5-methyl-furan-2-ylmethyl)-quinoline-2,5-diamine The title compound, MS: m/e=434.4 (M+H$^+$), was prepared in accordance with the general method of example 1 from 5-iodo-2-chloroquinoline, 5-methyl-2-furanmethanamine and 1,1-dioxido-3,4-dihydro-2H-thiochromen-4-ylamine.

Example 144 rac-N2-(2,2-Dimethyl-2,3-dihydro-benzofuran-7-yl)-N5-(1,1-dioxo-1l6-thiochroman-4-yl)-quinoline-2,5-diamine The title compound, MS: m/e=486.0 (M+H$^+$), was prepared in accordance with the general method of example 1 from 5-iodo-2-chloroquinoline, 7-amino-2,3-dihydro-2,2-dimethylbenzofuran (CAS 68298-46-4) and 1,1-dioxido-3,4-dihydro-2H-thiochromen-4-ylamine.

Example 145

N-(2-{[(5-methyl-2-furyl)methyl]amino}quinolin-5-yl)-N'-phenylsulfamide

The title compound, MS: m/e=409.1 (M+H$^+$), was prepared in accordance with the general method of example 58 from 5-nitro-2-chloroquinoline, 5-methyl-2-furanmethanamine and phenylsulfamoyl chloride.

Example 146

{4-Fluoro-N-[2-(2-methoxy-benzylamino)-quinolin-5-ylmethyl]-benzamide

Step A (5-Aminomethyl-quinolin-2-yl)-(2-methoxy-benzyl)-amine, light green oil, MS: m/e=294.2 (M+H$^+$), was prepared by hydrogenation of 2-(2-methoxy-benzylamino)-quinoline-5-carbonitrile (example 136, step B) as described in example 126, step B.

Step B

The title compound, white solid, MS: m/e=416.3 (M+H$^+$); m.p. 162.5° C., was prepared from (5-aminomethyl-quinolin-2-yl)-(2-methoxy-benzyl)-amine and 4-fluorobenzoyl chloride in accordance with the general method of example 126, step C.

Example 147

N2-(2,2-Dimethyl-2,3-dihydro-benzofuran-7-yl)-N5-(1H-indol-4-ylmethyl)-quinoline-2,5-diamine The title compound, MS: m/e=435.3 (M+H$^+$), was prepared from 5-nitro-2-chloroquinoline, 7-amino-2,3-dihydro-2,2-dimethylbenzofuran (CAS 68298-46-4) and indole-4-carboxaldehyde as described in example 26.

Example 148

N5-(1H-Benzoimidazol-5-ylmethyl)-N2-(2,2-dimethyl-2,3-dihydro-benzofuran-7-yl)-quinoline-2,5-diamine The title compound, MS: m/e=436.1 (M+H$^+$), was prepared from 5-nitro-2-chloroquinoline, 7-amino-2,3-dihydro-2,2-dimethylbenzofuran (CAS 68298-46-4) and 1H-benzimidazole-5-carbaldehyde as described in example 26.

Example 149

N2-(2,2-Dimethyl-2,3-dihydro-benzofuran-7-yl)-N5-(5-methyl-3H-imidazol-4-ylmethyl)-quinoline-2,5-diamine The title compound, MS: m/e=400.4 (M+H$^+$), was prepared from 5-nitro-2-chloroquinoline, 7-amino-2,3-dihydro-2,2-dimethylbenzofuran (CAS 68298-46-4) and 4-methyl-1H-imidazole-5-carbaldehyde as described in example 26.

Example 150

(2-Methoxy-benzyl)-[5-(5-methyl-[1,2,4]oxadiazol-3-yl)-quinolin-2-yl]-amine

Step A

A stirred suspension of 2-(2-methoxy-benzylamino)-quinoline-5-carbonitrile (example 136, step B) (289 mg, 1.0 mmol), hydroxylamine hydrochloride (257 mg, 3.7 mmol) and sodium carbonate (212 mg, 2.0 mmol) in EtOH (4 ml) and water (4 ml) was heated under reflux conditions for 17 h, water (5 ml) was added, the precipitate was collected by filtration, washed with water and heptane and dried to yield the crude product as solid which was further purified by crystallization (diethyl ether/MeOH) to yield N-hydroxy-2-(2-methoxy-benzylamino)-quinoline-5-carboxamidine as off-white solid (290 mg, 90%).

MS: m/e=323.2 (M+H$^+$); m.p. 161° C.

Step B

To a stirred solution of acetic acid (48 mg, 0.8 mmol) in THF (7.5 ml) was added at room temperature 1,1'-carbonyldiimidazole (151 mg, 0.93 mmol). The mixture was allowed to stir for 15 min at room temperature and for 90 min at 70° C., cooled to room temperature and N-hydroxy-2-(2-methoxy-benzylamino)-quinoline-5-carboxamidine (200 mg, 0.62 mmol) was added. The reaction mixture was allowed to stir at room temperature for 30 min, evaporated to dryness and diluted with acetic acid (7.5 ml). The reaction mixture was allowed to stir for 2 h at 100° C., evaporated, poured into saturated NaHCO$_3$ solution (20 ml) and extracted with ethyl acetate (2×30 ml). The combined organic layers were washed with brine (20 ml), dried (MgSO$_4$) and evaporated. The crude product was purified by flash chromatography (ethyl acetate/heptane) on silica gel and crystallization (dichloromethane/hexane) to yield the title compound as white solid (108 mg, 50%).

MS: m/e=347.1 (M+H$^+$)+); m.p. 121.5° C.

Example 151 rac-N5-[1-(3,5-Difluoro-phenyl)-ethyl]-N2-(2,2-dimethyl-2,3-dihydro-benzofuran-7-yl)-quinoline-2,5-diamine The title compound, MS: m/e=446.1 (M+H$^+$), was prepared in accordance with the general method of example 1 from 5-iodo-2-chloroquinoline, 7-amino-2,3-dihydro-2,2-dimethylbenzofuran (CAS 68298-46-4) and rac-1-(3,5-difluorophenyl)ethylamine.

Example 152 and 153

(R)— and (S)—N5-((S)-1,1-Dioxo-1l6-thiochroman-4-yl)-N2-(5-methyl-furan-2-ylmethyl)-quinoline-2,5-diamine rac-N2-(2,2-Dimethyl-2,3-dihydro-benzofuran-7-yl)-N5-(1,1-dioxo-1l6-thiochroman-4-yl)-quinoline-2,5-diamine was separated on Chiralcel OD with heptane/ethanol 4:1. The optical rotation of the two enantiomers could not be determined because it was too low.

Example 154

N-(2-{[(5-methyl-2-furyl)methyl]amino}quinolin-5-yl)-N'-(4-fluorophenyl)sulfamide The title compound, MS: m/e=427.3 (M+H$^+$), was prepared in accordance with the general method of example 58 from 5-nitro-2-chloroquinoline, 5-methyl-2-furanmethanamine and 4-fluoro-phenylsulfamoyl chloride.

Example 155

3,5-Difluoro-N-[2-(3-methoxy-phenylamino)-quinolin-5-yl]-benzenesulfonamide

The title compound, MS: m/e=442.0 (M+H$^+$), was prepared in accordance with the general method of example 89 from 5-nitro-2-chloroquinoline, 3,5-difluorobenzenesulfonylchloride and m-anisidine.

Example 156

N-{2-[(2,2-dimethyl-2,3-dihydro-1-benzofuran-7-yl)amino]quinolin-5-yl}-N'-(4-fluorophenyl)sulfamide The title compound, MS: m/e=479.0 (M+H$^+$), was prepared in accordance with the general method of example 58 from 5-nitro-2-chloroquinoline, 7-amino-2,3-dihydro-2,2-dimethylbenzofuran (CAS 68298-46-4) and 4-fluoro-phenylsulfamoyl chloride.

Example 157

3,5-Difluoro-N-(2-m-tolylamino-quinolin-5-yl)-benzenesulfonamide

The title compound, MS: m/e=426.0 (M+H$^+$), was prepared in accordance with the general method of example 89 from 5-nitro-2-chloroquinoline, 3,5-difluorobenzenesulfonylchloride and m-toluidine.

Example 158

(+)-N5-[1-(3,5-Difluoro-phenyl)-ethyl]-N2-(2,2-dimethyl-2,3-dihydro-benzofuran-7-yl)-quinoline-2,5-diamine (rac)-N5-[1-(3,5-Difluoro-phenyl)-ethyl]-N2-(2,2-dimethyl-2,3-dihydro-benzofuran-7-yl)-quinoline-2,5-diamine was separated on Chiralcel OD with heptane/ethanol 4:1. The (+)-enantiomer is more active at the 5-HT$_{5A}$ receptor.

Example 159

N-[2-(3-Cyclopropyl-phenylamino)-quinolin-5-yl]-3,5-difluoro-benzenesulfonamide

The title compound, MS: m/e=452.0 (M+H$^+$), was prepared in accordance with the general method of example 89 from 5-nitro-2-chloroquinoline, 3,5-difluorobenzenesulfonylchloride and 3-cyclopropylaniline.

Example 160 rac-N2-(2,2-Dimethyl-2,3-dihydro-benzofuran-7-yl)-N5-(1-thiazol-2-yl-ethyl)-quinoline-2,5-diamine The title compound, MS: m/e=417.4 (M+H⁺), was prepared from 5-nitro-2-chloroquinoline, 7-amino-2,3-dihydro-2,2-dimethylbenzofuran (CAS 68298-46-4) and 2-acetylthiazole as described in example 26.

Example 161

N-[2-(3-tert-Butyl-phenylamino)-quinolin-5-yl]-3,5-difluoro-benzenesulfonamide

The title compound, MS: m/e=468.3 (M+H⁺), was prepared in accordance with the general method of example 89 from 5-nitro-2-chloroquinoline, 3,5-difluorobenzenesulfonylchloride and 3-tert.butyl-aniline.

Example 162 rac-N2-(2,2-Dimethyl-2,3-dihydro-benzofuran-7-yl)-N5-(1-pyridin-3-yl-ethyl)-quinoline-2,5-diamine The title compound, MS: m/e=411.5 (M+H⁺), was prepared in accordance with the general method of example 1 from 5-iodo-2-chloroquinoline, 7-amino-2,3-dihydro-2,2-dimethylbenzofuran (CAS 68298-46-4) and rac-1-pyridine-3-yl-ethylamine.

Example 163

N2-(2,2-Dimethyl-2,3-dihydro-benzofuran-7-yl)-N5-pyridin-3-ylmethyl-quinoline-2,5-diamine The title compound, MS: m/e=397.3 (M+H⁺), was prepared in accordance with the general method of example 1 from 5-iodo-2-chloroquinoline, 7-amino-2,3-dihydro-2,2-dimethylbenzofuran (CAS 68298-46-4) and 3-picolylamine.

Example 164

N2-(3-Cyclopropyl-phenyl)-N5-(1H-indol-4-ylmethyl)-quinoline-2,5-diamine

The title compound, MS: m/e=405.5 (M+H⁺), was prepared from 5-nitro-2-chloroquinoline, 3-cyclopropylaniline and 4-indolecarbaldehyde as described in example 26.

Example 165

N5-(1H-Benzoimidazol-5-ylmethyl)-N2-(3-cyclopropyl-phenyl)-quinoline-2,5-diamine The title compound, MS: m/e=406.5 (M+H⁺), was prepared from 5-nitro-2-chloroquinoline, 3-cyclopropylaniline and 1H-benzimidazole-5-carbaldehyde as described in example 26.

Example 166

N2-(3-Cyclopropyl-phenyl)-N5-(5-methyl-3H-imidazol-4-ylmethyl)-quinoline-2,5-diamine The title compound, MS: m/e=370.4 (M+H⁺), was prepared from 5-nitro-2-chloroquinoline, 3-cyclopropylaniline and 4-methyl-1H-imidazole-5-carbaldehyde as described in example 26.

Example 167

(4-Fluoro-phenyl)-[2-(2-methoxy-benzylamino)-quinolin-5-yl]-methanone oxime

A stirred suspension of (4-fluoro-phenyl)-[2-(2-methoxy-benzylamino)-quinolin-5-yl]-methanone (example 137) (60 mg, 0.155 mmol), hydroxylamine hydrochloride (32 mg, 0.46 mmol) and sodium carbonate (49 mg, 0.46 mmol) in EtOH (2 ml) was heated under reflux conditions for 28 h, the reaction mixture was poured into water (20 ml) and extracted with ethyl acetate (3×50 ml). The combined organic layers were washed with brine (50 ml), dried (MgSO₄) and evaporated. The crude product was further purified by flash chromatography on silica gel (heptane/ethyl acetate) to yield the title compound as white foam (40 mg, 64%).

MS: m/e=402.4 (M+H⁺).

The invention claimed is:

1. A compound of formula (I)

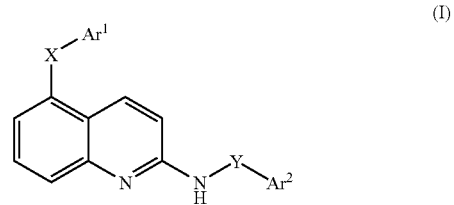

(I)

wherein

X is a bond, —CH₂CH₂—, —CH═CH—, —CH₂O—, —CH₂NR—, —CH₂S(O)—, —CH₂S(O)₂—, —O—, —OCH₂CH₂—, —S—, —SCH₂—, —OCH₂CH₂S(O)—, —OCH₂CH₂S(O)₂—, —CH₂NRCO—, —CH₂NRCH₂—,

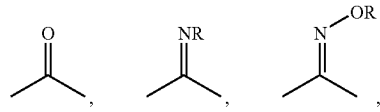

—NRS(O)₂NR—, —NHCHR—, —NR—, or —NRS(O)₂—; and wherein X can be inserted in both directions into formula (I);

Y is a bond, —CHR— or —OCH₂CH₂—;

R is hydrogen or lower alkyl;

Ar¹/Ar² are each independently aryl or 5 to 10 membered heteroaryl, optionally substituted by lower alkyl, lower alkoxy, lower haloalkoxy, halogen, —CF₃, —CH₂OH, —CH₂O-lower alkyl, 3 to 10 membered cycloalkyl, 5 to 10 membered heterocycloalkyl, —CH₂O(CH₂)₂O-lower alkyl, —S(O)₂-lower alkyl or —S(O)₂NHR;

or a pharmaceutically acceptable acid addition salt thereof.

2. A compound according to claim 1, wherein

X is a bond, —CH₂CH₂—, —CH═CH—, —CH₂O—, —CH₂NR—, CH₂S(O)₂—, —O—, —OCH₂—, —OCH₂CH₂—, —S—, —SCH₂—, —NR—, NRCH₂— or —NRS(O)₂—;

Y is a bond, —CHR— or —OCH₂CH₂—;

R is hydrogen or lower alkyl;

Ar¹/Ar² are each independently (i) a monovalent cyclic aromatic hydrocarbon radical consisting of one or more fused rings in which at least one ring is aromatic in nature or (ii) a cyclic aromatic hydrocarbon radical, containing one, two or three heteroatoms, selected from the group consisting of oxygen, sulphur or nitrogen and wherein (i) and (ii) are optionally substituted by lower alkyl, lower alkoxy, halogen, —CF$_3$, —CH$_2$OH, —CH$_2$O-lower lower alkyl, —CH$_2$O(CH$_2$)$_2$O-lower alkyl, —S(O)$_2$-lower alkyl or —S(O)$_2$NHR;

or a pharmaceutically acceptable acid addition salt thereof.

3. A compound according to claim 2, wherein
(i) is selected from the group consisting of phenyl and naphthyl, and
(ii) is selected from the group consisting of pyridyl, pyrazinyl, pyrimidinyl, pyridazinyl, triazinyl, thiazolyl, thienyl, furyl, pyrrolyl, imidazolyl, pyrazolyl, oxazolyl, isothiazolyl and isoxazolyl.

4. A compound according to claim 1, wherein X is —CH$_2$CH$_2$—.

5. A compound according to claim 4, selected from the group consisting of
(2-methoxy-benzyl)-(5-phenethyl-quinolin-2-yl)-amine,
(2-methoxy-benzyl)-[5-(2-pyridin-3-yl-ethyl)-quinolin-2-yl]-amine,
(5-methyl-furan-2-ylmethyl)-(5-phenethyl-quinolin-2-yl)-amine,
(3-{2-[2-(2-methoxy-benzylamino)-quinolin-5-yl]-ethyl}-phenyl)-methanol,
{5-[2-(3-methoxymethyl-phenyl)-ethyl]-quinolin-2-yl}-(5-methyl-furan-2-ylmethyl)-amine,
3-(2-{2-[(5-methyl-furan-2-ylmethyl)-amino]-quinolin-5-yl}-ethyl)-benzenesulfonamide and
(5-methyl-furan-2-ylmethyl)-[5-(2-pyridin-2-yl-ethyl)-quinolin-2-yl]-amine.

6. A compound according to claim 1, wherein X is —CH$_2$NR—.

7. A compound according to claim 6, selected from the group consisting of
(5-methyl-furan-2-ylmethyl)-[5-(pyridin-3-ylaminomethyl)-quinolin-2-yl]-amine,
(5-methyl-furan-2-ylmethyl)-(5-phenylaminomethyl-quinolin-2-yl)-amine and
(5-methyl-furan-2-ylmethyl)-[5-(pyridin-2-ylaminomethyl)-quinolin-2-yl]-amine.

8. A compound according to claim 1, wherein X is SCH$_2$.

9. A compound according to claim 8, which is (5-benzylsulfanyl-quinolin-2-yl)-(5-methyl-furan-2-ylmethyl)-amine.

10. A compound according to claim 1, wherein X is —NR—.

11. A compound according to claim 10, selected from the group consisting of
N5-(4-fluoro-phenyl)-N2-(5-methyl-furan-2-ylmethyl)-quinoline-2,5-diamine,
N5-(4-chloro-phenyl)-N2-(5-methyl-furan-2-ylmethyl)-quinoline-2,5-diamine and
N5-(6-chloro-pyridin-3-yl)-N2-(5-methyl-furan-2-ylmethyl)-quinoline-2,5-diamine.

12. A compound according to claim 1, wherein X is —NRCH$_2$—.

13. A compound according to claim 12, selected from the group consisting of
N2-(2-methoxy-benzyl)-N5-pyridin-3-ylmethyl-quinoline-2,5-diamine,
N5-(3-methoxy-benzyl)-N2-(2-methoxy-benzyl)-quinoline-2,5-diamine,
N2,N5-bis-(2-methoxy-benzyl)-quinoline-2,5-diamine,
N5-benzyl-N2-(2-methoxy-benzyl)-quinoline-2,5-diamine,
N2-(2-methoxy-benzyl)-N5-pyridin-4-ylmethyl-quinoline-2,5-diamine,
N5-(2-methoxy-benzyl)-N2-(5-methyl-furan-2-ylmethyl)-quinoline-2,5-diamine,
N2-(5-methyl-furan-2-ylmethyl)-N5-pyridin-3-ylmethyl-quinoline-2,5-diamine,
N5-(4-fluoro-benzyl)-N2-(5-methyl-furan-2-ylmethyl)-quinoline-2,5-diamine,
N2-(5-methyl-furan-2-ylmethyl)-N5-pyridin-2-ylmethyl-quinoline-2,5-diamine,
N5-(2-methoxy-pyridin-3-ylmethyl)-N2-(5-methyl-furan-2-ylmethyl)-quinoline-2,5-diamine,
N5-[3-(2-methoxy-ethoxy)-benzyl]-N2-(5-methyl-furan-2-ylmethyl)-quinoline-2,5-diamine,
N2-(5-methyl-furan-2-ylmethyl)-N5-(6-methyl-pyridin-2-ylmethyl)-quinoline-2,5-diamine, and
3-({2-[(5-methyl-furan-2-ylmethyl)-amino]-quinolin-5-ylamino}-methyl)-benzenesulfonamide.

14. A compound according to claim 1, wherein X is —NRS(O)$_2$—.

15. A compound according to claim 14, selected form the group consisting of
N-{2-[(5-methyl-furan-2-ylmethyl)-amino]-quinolin-5-yl}-benzenesulfonamide,
N-{2-[(5-methyl-furan-2-ylmethyl)-amino]-quinolin-5-yl}-4-fluoro-benzenesulfonamide,
5-chloro-thiophene-2-sulfonic acid {2-[(5-methyl-furan-2-ylmethyl)-amino]-quinolin-5-yl}-amide,
6-chloro-pyridine-3-sulfonic acid {2-[(5-methyl-furan-2-ylmethyl)-amino]-quinolin-5-yl}-amide,
3,5-difluoro-N-{2-[(5-methyl-furan-2-ylmethyl)-amino]-quinolin-5-yl}-benzenesulfonamide,
4-fluoro-N-[2-(2-methoxy-benzylamino)-quinolin-5-yl]-benzenesulfonamide,
3-fluoro-N-{2-[(5-methyl-furan-2-ylmethyl)-amino]-quinolin-5-yl}-benzenesulfonamide,
3,4-difluoro-N-{2-[(5-methyl-furan-2-ylmethyl)-amino]-quinolin-5-yl}-benzenesulfonamide and
3,5-difluoro-N-[2-(2-phenoxy-ethylamino)-quinolin-5-yl]-benzenesulfonamide.

16. A compound according to claim 1, selected from the group consisting of
4-Fluoro-N-[2-(2-methylsulfanyl-benzylamino)-quinolin-5-yl]-benzenesulfonamide,
[5-(2-Benzenesulfinyl-ethoxy)-quinolin-2-yl]-(2-methoxy-benzyl)-amine,
[5-(2-Benzenesulfonyl-ethoxy)-quinolin-2-yl]-(2-methoxy-benzyl)-amine,
3,5-Difluoro-N-{2-[(5-methyl-thiophen-2-ylmethyl)-amino]-quinolin-5-yl}-benzenesulfonamide,
3,5-Difluoro-N-{2-[1-(5-methyl-furan-2-yl)-ethylamino]-quinolin-5-yl}-benzenesulfonamide,
N5-(1H-Imidazol-4-ylmethyl)-N2-(5-methyl-furan-2-ylmethyl)-quinoline-2,5-diamine,
N2-(5-Methyl-furan-2-ylmethyl)-N5-(1H-pyrazol-3-ylmethyl)-quinoline-2,5-diamine,
N5-(1H-Indol-4-ylmethyl)-N2-(5-methyl-furan-2-ylmethyl)-quinoline-2,5-diamine,
3,5-Difluoro-N-[2-(2-methyl-benzofuran-7-ylamino)-quinolin-5-yl]-benzenesulfonamide,
N2-(5-Methyl-furan-2-ylmethyl)-N5-(2-methyl-1H-imidazol-4-ylmethyl)-quinoline-2,5-diamine,
N2-(5-Methyl-furan-2-ylmethyl)-N5-(1-methyl-1H-pyrrol-2-ylmethyl)-quinoline-2,5-diamine,
N5-(1H-Indol-4-yl)-N2-(5-methyl-furan-2-ylmethyl)-quinoline-2,5-diamine, N5-(1H-Indol-7-yl)-N2-(5-methyl-furan-2-ylmethyl)-quinoline-2,5-diamine,
N2-(5-Methyl-furan-2-ylmethyl)-N5-(5-methyl-1H-imidazol-4-ylmethyl)-quinoline-2,5-diamine,
N2-(2-Methoxy-benzyl)-N5-(1H-pyrazol-3-ylmethyl)-quinoline-2,5-diamine,
N2-(2-Methoxy-benzyl)-N5-(2-methyl-3H-imidazol-4-ylmethyl)-quinoline-2,5-diamine,
N2-(2-Methoxy-benzyl)-N5-(5-methyl-3H-imidazol-4-ylmethyl)-quinoline-2,5-diamine,
N5-(3H-Imidazol-4-ylmethyl)-N2-(2-methoxy-benzyl)-quinoline-2,5-diamine,
N2-(5-Methyl-furan-2-ylmethyl)-N5-thiazol-2-ylmethyl-quinoline-2,5-diamine,
N2-(2,6-Dimethoxy-benzyl)-N5-pyridin-3-ylmethyl-quinoline-2,5-diamine,
N5-(1H-Indol-4-ylmethyl)-N2-(2-methoxy-benzyl)-quinoline-2,5-diamine,
N5-Benzo[1,3]dioxol-4-ylmethyl-N2-(5-methyl-furan-2-ylmethyl)-quinoline-2,5-diamine,
N5-(4-Methyl-3,4-dihydro-2H-benzo[1,4]oxazin-7-ylmethyl)-N2-(5-methyl-furan-2-ylmethyl)-quinoline-2,5-diamine,
N2-(5-Methyl-furan-2-ylmethyl)-N5-[2-(4-methyl-piperazin-1-yl)-benzyl]-quinoline-2,5-diamine,
N2-(2-Methoxy-benzyl)-N5-(1H-[1,2,3]triazol-4-ylmethyl)-quinoline-2,5-diamine,
N5-(1H-Benzoimidazol-5-ylmethyl)-N2-(5-methyl-furan-2-ylmethyl)-quinoline-2,5-diamine,
4-Fluoro-N-[2-(2-trifluoromethoxy-benzylamino)-quinolin-5-yl]-benzenesulfonamide,
N2-(2,6-Dimethoxy-benzyl)-N5-(1H-indol-4-ylmethyl)-quinoline-2,5-diamine,
N2-(2-Methoxy-benzyl)-N5-thiazol-2-ylmethyl-quinoline-2,5-diamine,
N5-(1H-Indol-4-ylmethyl)-N2-(2-methyl-benzofuran-7-yl)-quinoline-2,5-diamine,
N2-(5-Methyl-furan-2-ylmethyl)-N5-(5-methyl-1H-pyrazol-3-yl)-quinoline-2,5-diamine,
N5-(1H-Indol-4-yl)-N2-(2-methyl-benzofuran-7-yl)-quinoline-2,5-diamine,
N5-(3H-Benzoimidazol-5-ylmethyl)-N2-(2-methoxy-benzyl)-quinoline-2,5-diamine,
N2-(5-Methyl-furan-2-ylmethyl)-N5-(3H-[1,2,3]triazol-4-ylmethyl)-quinoline-2,5-diamine,
N5-(1H-Indol-4-ylmethyl)-N2-(2-trifluoromethoxy-benzyl)-quinoline-2,5-diamine,
N5-(1H-Benzoimidazol-5-ylmethyl)-N2-(2-trifluoromethoxy-benzyl)-quinoline-2,5-diamine,
N2-(2,3-Dihydro-benzo[1,4]dioxin-5-ylmethyl)-N5-(1H-indol-4-ylmethyl)-quinoline-2,5-diamine,
N5-(7-Fluoro-1H-indol-4-yl)-N2-(5-methyl-furan-2-ylmethyl)-quinoline-2,5-diamine,
N5-(3,5-Difluoro-benzyl)-N2-(5-methyl-furan-2-ylmethyl)-quinoline-2,5-diamine,
N-[2-(2,3-Dihydro-benzo[1,4]dioxin-5-ylamino)-quinolin-5-yl]-3,5-difluoro-benzenesulfonamide,
3,5-Difluoro-N-[2-(naphthalen-1-ylamino)-quinolin-5-yl]-benzenesulfonamide,
3,5-Difluoro-N-[2-(indan-4-ylamino)-quinolin-5-yl]-benzenesulfonamide,
N5-(1H-Benzoimidazol-5-ylmethyl)-N2-(2-methyl-benzofuran-7-yl)-quinoline-2,5-diamine,
N2-(2-Methyl-benzofuran-7-yl)-N5-(5-methyl-3H-imidazol-4-ylmethyl)-quinoline-2,5-diamine,
4-Fluoro-N-{2-[(5-methyl-furan-2-ylmethyl)-amino]-quinolin-5-ylmethyl}-benzamide,
{5-[(4-Fluoro-benzylamino)-methyl]-quinolin-2-yl}-(5-methyl-furan-2-ylmethyl)-amine,
4-Fluoro-N-[2-(2-methyl-benzofuran-7-ylamino)-quinolin-5-yl]-benzenesulfonamide,
N2-(2-Methyl-benzofuran-7-yl)-N5-pyridin-3-ylmethyl-quinoline-2,5-diamine,
5-Chloro-thiophene-2-sulfonic acid [2-(2-methyl-benzofuran-7-ylamino)-quinolin-5-yl]-amide,
N5-(3H-Imidazol-4-ylmethyl)-N2-(2-methyl-benzofuran-7-yl)-quinoline-2,5-diamine,
N5-(3,5-Difluoro-benzyl)-N2-(2-methyl-benzofuran-7-yl)-quinoline-2,5-diamine,
N5-(4-Fluoro-phenyl)-N2-(2-methyl-benzofuran-7-yl)-quinoline-2,5-diamine,
rac-3,5-Difluoro-N-[2-(2-methyl-2,3-dihydro-benzofuran-7-ylamino)-quinolin-5-yl]-benzenesulfonamide,
rac-N2-(5-Methyl-furan-2-ylmethyl)-N5-thiochroman-4-yl-quinoline-2,5-diamine,
{5-[(4-Fluoro-phenyl)-imino-methyl]-quinolin-2-yl}-(2-methoxy-benzyl)-amine,
(4-Fluoro-phenyl)-[2-(2-methoxy-benzylamino)-quinolin-5-yl]-methanone,
N-[2-(2-tert-Butyl-benzofuran-7-ylamino)-quinolin-5-yl]-3,5-difluoro-benzenesulfonamide,
N-[2-(2,3-Dihydro-benzofuran-7-ylamino)-quinolin-5-yl]-3,5-difluoro-benzenesulfonamide,
N5-(1H-Indol-4-ylmethyl)-N2-(2-methyl-2,3-dihydro-benzofuran-7-yl)-quinoline-2,5-diamine,
N-[2-(2,2-Dimethyl-2,3-dihydro-benzofuran-7-ylamino)-quinolin-5-yl]-3,5-difluoro-benzenesulfonamide,
rac-N5-Chroman-4-yl-N2-(5-methyl-furan-2-ylmethyl)-quinoline-2,5-diamine,
rac-5-(1,1-Dioxo-1l6-thiochroman-4-yl)-N2-(5-methyl-furan-2-ylmethyl)-quinoline-2,5-diamine,
rac-N2-(2,2-Dimethyl-2,3-dihydro-benzofuran-7-yl)-N5-(1,1-dioxo-1l6-thiochroman-4-yl)-quinoline-2,5-diamine,
N-(2-{[(5-methyl-2-furyl)methyl]amino}quinolin-5-yl)-N'-phenylsulfamide,
4-Fluoro-N-[2-(2-methoxy-benzylamino)-quinolin-5-ylmethyl]-benzamide,
N2-(2,2-Dimethyl-2,3-dihydro-benzofuran-7-yl)-N5-(1H-indol-4-ylmethyl)-quinoline-2,5-diamine,
N5-(1H-Benzoimidazol-5-ylmethyl)-N2-(2,2-dimethyl-2,3-dihydro-benzofuran-7-yl)-quinoline-2,5-diamine,
N2-(2,2-Dimethyl-2,3-dihydro-benzofuran-7-yl)-N5-(5-methyl-3H-imidazol-4-ylmethyl)-quinoline-2,5-diamine,
(2-Methoxy-benzyl)-[5-(5-methyl-[1,2,4]oxadiazol-3-yl)-quinolin-2-yl]-amine,
rac-N5-[1-(3,5-Difluoro-phenyl)-ethyl]-N2-(2,2-dimethyl-2,3-dihydro-benzofuran-7-yl)-quinoline-2,5-diamine,
(R)— or (S)—N5-((S)-1,1-Dioxo-1l6-thiochroman-4-yl)-N2-(5-methyl-furan-2-ylmethyl)-quinoline-2,5-diamine,
(R)— or (S)—N5-((S)-1,1-Dioxo-1l6-thiochroman-4-yl)-N2-(5-methyl-furan-2-ylmethyl)-quinoline-2,5-diamine,
N-(2-{[(5-methyl-2-furyl)methyl]amino}quinolin-5-yl)-N'-(4-fluorophenyl)sulfamide,
3,5-Difluoro-N-[2-(3-methoxy-phenylamino)-quinolin-5-yl]-benzenesulfonamide,
N-{2-[(2,2-dimethyl-2,3-dihydro-1-benzofuran-7-yl)amino]quinolin-5-yl}-N'-(4-fluorophenyl)sulfamide,
3,5-Difluoro-N-(2-m-tolylamino-quinolin-5-yl)-benzenesulfonamide, (+)-N5-[1-(3,5-Difluoro-phenyl)-ethyl]-N2-(2,2-dimethyl-2,3-dihydro-benzofuran-7-yl)-quinoline-2,5-diamine, N-[2-(3-Cyclopropyl-phenylamino)-quinolin-5-yl]-3,5-difluoro-benzenesulfonamide, rac-N2-(2,2-Dimethyl-2,3-dihydro-benzofuran-7-yl)-N5-(1-thiazol-2-yl-ethyl)-quinoline-2,5-diamine, N-[2-(3-tert-Butyl-phenylamino)-quinolin-5-yl]-3,5-difluoro-benzenesulfonamide, rac-N2-(2,2-Dimethyl-2,3-dihydro-benzofuran-7-yl)-N5-(1-pyridin-3-yl-ethyl)-quinoline-2,5-diamine, N2-(2,2-Dimethyl-2,3-dihydro-benzofuran-7-yl)-N5-pyridin-3-ylmethyl-quinoline-2,5-diamine, N2-(3-Cyclopropyl-phenyl)-N5-(1H-indol-4-ylmethyl)-quinoline-2,5-diamine, N5-(1H-Benzoimidazol-5-ylmethyl)-N2-(3-cyclopropyl-phenyl)-quinoline-2,5-diamine, N2-(3-Cyclopropyl-phenyl)-N5-(5-methyl-3H-imidazol-4-ylmethyl)-quinoline-2,5-diamine, and (4-Fluoro-phenyl)-[2-(2-methoxy-benzylamino)-quinolin-5-yl]-methanone oxime.

17. A compound according to claim 1, having formula (Ia)

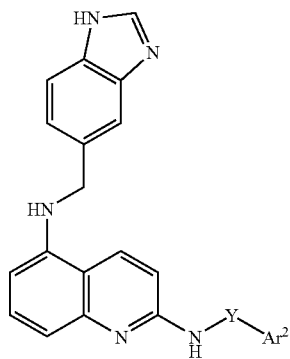

(Ia)

wherein

Y is a bond, —CHR— or —OCH$_2$CH$_2$—; and wherein X can be inserted in both directions into formula (I); and Ar$^2$ is aryl or 5 to 10 membered heteroaryl, optionally substituted by lower alkyl, lower alkoxy, lower haloalkoxy, halogen, —CF$_3$, —CH$_2$OH, —CH$_2$O-lower alkyl, 3 to 10 membered cycloalkyl, 5 to 10 membered heterocycloalkyl, —CH$_2$O(CH$_2$)$_2$O-lower alkyl, —S(O)$_2$-lower alkyl or —S(O)$_2$NHR.

18. A compound according to claim 17, selected from the group consisting of

N5-(1H-Benzoimidazol-5-ylmethyl)-N2-(5-methyl-furan-2-ylmethyl)-quinoline-2,5-diamine, N5-(3H-Benzoimidazol-5-ylmethyl)-N2-(2-methoxy-benzyl)-quinoline-2,5-diamine, N5-(1H-Benzoimidazol-5-ylmethyl)-N2-(2-trifluoromethoxy-benzyl)-quinoline-2,5-diamine, N5-(1H-Benzoimidazol-5-ylmethyl)-N2-(2-methyl-benzofuran-7-yl)-quinoline-2,5-diamine, N5-(1H-Benzoimidazol-5-ylmethyl)-N2-(2,2-dimethyl-2,3-dihydro-benzofuran-7-yl)-quinoline-2,5-diamine, and N5-(1H-Benzoimidazol-5-ylmethyl)-N2-(3-cyclopropyl-phenyl)-quinoline-2,5-diamine.

19. A compound according to claim 1, having formula (Ib)

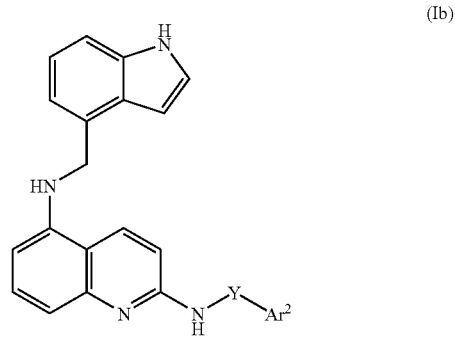

(Ib)

wherein

Y is a bond, —CHR— or —OCH$_2$CH$_2$—; and wherein X can be inserted in both directions into formula (I); and Ar$^2$ is aryl or 5 to 10 membered heteroaryl, optionally substituted by lower alkyl, lower alkoxy, lower haloalkoxy, halogen, —CF$_3$, —CH$_2$OH, —CH$_2$O-lower alkyl, 3 to 10 membered cycloalkyl, 5 to 10 membered heterocycloalkyl, —CH$_2$O(CH$_2$)$_2$O-lower alkyl, —S(O)$_2$-lower alkyl or —S(O)$_2$NHR.

20. A compound according to claim 17, selected from the group consisting of

N5-(1H-Indol-4-ylmethyl)-N2-(5-methyl-furan-2-ylmethyl)-quinoline-2,5-diamine,

N5-(1H-Indol-4-ylmethyl)-N2-(2-methoxy-benzyl)-quinoline-2,5-diamine,

N2-(2,6-Dimethoxy-benzyl)-N5-(1H-indol-4-ylmethyl)-quinoline-2,5-diamine,

N5-(1H-Indol-4-ylmethyl)-N2-(2-methyl-benzofuran-7-yl)-quinoline-2,5-diamine,

N5-(1H-Indol-4-ylmethyl)-N2-(2-trifluoromethoxy-benzyl)-quinoline-2,5-diamine,

N2-(2,3-Dihydro-benzo[1,4]dioxin-5-ylmethyl)-N5-(1H-indol-4-ylmethyl)-quinoline-2,5-diamine, N5-(1H-Indol-4-ylmethyl)-N2-(2-methyl-2,3-dihydro-benzofuran-7-yl)-quinoline-2,5-diamine, N2-(2,2-Dimethyl-2,3-dihydro-benzofuran-7-yl)-N5-(1H-indol-4-ylmethyl)-quinoline-2,5-diamine, and N2-(3-Cyclopropyl-phenyl)-N5-(1H-indol-4-ylmethyl)-quinoline-2,5-diamine.

21. A compound according to claim 1, selected from the group consisting of (2-Methoxy-benzyl)-(5-phenyl-quinolin-2-yl)-amine;

N2-(2-Methoxy-benzyl)-N5-(3-methyl-3H-imidazol-4-ylmethyl)-quinoline-2,5-diamine;

(2-Methoxy-benzyl)-[5-((E)-2-pyridin-3-yl-vinyl)-quinolin-2-yl]-amine;

(2-Methoxy-benzyl)-[5-((E)-2-pyrimidin-5-yl-vinyl)-quinolin-2-yl]-amine;

N5-(2-Methoxy-benzyl)-N2-(5-methyl-furan-2-ylmethyl)-quinoline-2,5-diamine;

(5-Methyl-furan-2-ylmethyl)-[5-((E)-styryl)-quinolin-2-yl]-amine;

N2-(5-Methyl-furan-2-ylmethyl)-N5-pyridin-3-ylmethyl-quinoline-2,5-diamine;

(2-Methoxy-benzyl)-[5-(2-pyridin-3-yl-ethyl)-quinolin-2-yl]-amine;

(2-Methoxy-benzyl)-[5-(2-pyrimidin-5-yl-ethyl)-quinolin-2-yl]-amine;

N5-(4-Fluoro-benzyl)-N2-(5-methyl-furan-2-ylmethyl)-quinoline-2,5-diamine;
(3-{2-[2-(2-Methoxy-benzylamino)-quinolin-5-yl]-ethyl}-phenyl)-methanol;
N5-(3-Methoxymethyl-benzyl)-N2-(5-methyl-furan-2-ylmethyl)-quinoline-2,5-diamine;
N5-[3-(2-Methoxy-ethoxymethyl)-benzyl]-N2-(5-methyl-furan-2-ylmethyl)-quinoline-2,5-diamine;
N2-(5-Methyl-furan-2-ylmethyl)-N5-pyridin-2-ylmethyl-quinoline-2,5-diamine;
N5-(2-Methoxy-pyridin-3-ylmethyl)-N2-(5-methyl-furan-2-ylmethyl)-quinoline-2,5-diamine;
N5-[3-(2-Methoxy-ethoxy)-benzyl]-N2-(5-methyl-furan-2-ylmethyl)-quinoline-2,5-diamine;
N2-(5-Methyl-furan-2-ylmethyl)-N5-(6-methyl-pyridin-2-ylmethyl)-quinoline-2,5-diamine;
{5-[(E)-2-(3-Methoxymethyl-phenyl)-vinyl]-quinolin-2-yl}-(5-methyl-furan-2-ylmethyl)-amine;
3-({2-[(5-Methyl-furan-2-ylmethyl)-amino]-quinolin-5-ylamino}-methyl)-benzenesulfonamide;
(5-Methyl-furan-2-ylmethyl)-[5-(pyrimidin-2-ylaminomethyl)-quinolin-2-yl]-amine;
N2-(5-Methyl-furan-2-ylmethyl)-N5-pyridin-2-yl-quinoline-2,5-diamine;
(5-Methyl-furan-2-ylmethyl)-(5-phenoxymethyl-quinolin-2-yl)-amine;
(5-Methyl-furan-2-ylmethyl)-[5-((E)-2-pyridin-2-yl-vinyl)-quinolin-2-yl]-amine;
{5-[(E)-2-(4-Fluoro-phenyl)-vinyl]-quinolin-2-yl}-(5-methyl-furan-2-ylmethyl)-amine;
N5-(4-Fluoro-phenyl)-N2-(5-methyl-furan-2-ylmethyl)-quinoline-2,5-diamine;
4-Fluoro-N-methyl-N-{2-[(5-methyl-furan-2-ylmethyl)-amino]-quinolin-5-yl}-benzenesulfonamide;
N5-(4-Chloro-phenyl)-N2-(5-methyl-furan-2-ylmethyl)-quinoline-2,5-diamine;
N5-(3,5-Difluoro-phenyl)-N2-(5-methyl-furan-2-ylmethyl)-quinoline-2,5-diamine;
[5-(4-Fluoro-benzylsulfanyl)-quinolin-2-yl]-(5-methyl-furan-2-ylmethyl)-amine;
(5-Methyl-furan-2-ylmethyl)-[5-(2-pyridin-2-yl-ethyl)-quinolin-2-yl]-amine;
N5-(6-Chloro-pyridin-3-yl)-N2-(5-methyl-furan-2-ylmethyl)-quinoline-2,5-diamine;
-Chloro-thiophene-2-sulfonic acid {2-[(5-methyl-furan-2-ylmethyl)-amino]-quinolin-5-yl}-amide;
6-Chloro-pyridine-3-sulfonic acid {2-[(5-methyl-furan-2-ylmethyl)-amino]-quinolin-5-yl}-amide;
3,5-Difluoro-N-{2-[(5-methyl-furan-2-ylmethyl)-amino]-quinolin-5-yl}-benzenesulfonamide; and
4-Fluoro-N-[2-(2-methoxy-benzylamino)-quinolin-5-yl]-benzenesulfonamide.

* * * * *